US008206965B2

(12) United States Patent
Arnould et al.

(10) Patent No.: US 8,206,965 B2
(45) Date of Patent: Jun. 26, 2012

(54) HYBRID AND SINGLE CHAIN MEGANUCLEASES AND USE THEREOF

(75) Inventors: Sylvain Arnould, Paris (FR); Patrick Chames, Paris (FR); Andre Choulika, Paris (FR); Jean-Charles Epinat, Paris (FR); Emmanuel Lacroix, Paris (FR)

(73) Assignee: Cellectis S.A., Paris (FR)

( * ) Notice: Subject to any disclaimer, the term of this patent is extended or adjusted under 35 U.S.C. 154(b) by 529 days.

(21) Appl. No.: 10/388,230

(22) Filed: Mar. 14, 2003

(65) Prior Publication Data

US 2004/0002092 A1 Jan. 1, 2004

Related U.S. Application Data

(60) Provisional application No. 60/364,113, filed on Mar. 15, 2002.

(51) Int. Cl.
*C12N 9/22* (2006.01)
*C12N 15/55* (2006.01)
(52) U.S. Cl. ......... 435/199; 435/183; 435/196; 530/350
(58) Field of Classification Search .................. 435/194; 530/350
See application file for complete search history.

(56) References Cited

U.S. PATENT DOCUMENTS

| | | | |
|---|---|---|---|
| 5,474,896 A | 12/1995 | Dujon et al. | |
| 5,792,632 A | 8/1998 | Dujon et al. | |
| 5,801,030 A | 9/1998 | McVey et al. | |
| 5,830,729 A | 11/1998 | Jaisser et al. | |
| 5,866,361 A | 2/1999 | Dujon et al. | |
| 5,948,678 A | 9/1999 | Dujon et al. | |
| 5,962,327 A | 10/1999 | Dujon et al. | |
| 6,238,924 B1 | 5/2001 | Dujon et al. | |
| 6,395,959 B1 | 5/2002 | Dujon et al. | |
| 6,566,579 B1 | 5/2003 | Jaisser et al. | |
| 6,610,545 B2 | 8/2003 | Dujon et al. | |
| 6,822,137 B1 | 11/2004 | Dujon et al. | |
| 6,833,252 B1 | 12/2004 | Dujon et al. | |

FOREIGN PATENT DOCUMENTS

| | | |
|---|---|---|
| WO | WO 94/18313 | 8/1994 |
| WO | WO 95/09233 | 4/1995 |
| WO | WO 96/14408 | 5/1996 |
| WO | WO 98/36079 | 8/1998 |
| WO | WO 00/46385 | 8/2000 |
| WO | WO 00/46386 | 8/2000 |
| WO | 2005/105989 | 10/2005 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Nahon and Raveh, Nuc. Acids. Res. vol. 26, No. 5, pp. 1233-1239, 1998.*
Xu et al, PNAS, Nov. 6, 2001, vol. 98, No. 23, pp. 12990-12995.
Bibikova et al, Molecular and Cellular Biology, Jan. 2001, vol. 21, No. 1, pp. 289-297.
Epinat et al, Nucleic Acids Research, 2003, vol. 31, No. 11, pp. 2952-2962.
Chames et al, Nucleic Acids Research, 2005, vol. 33, No. 20, e178, 1-10.
Arnould et al, J. Mol. Biol. (2006), vol. 355, No. 3, pp. 443-458.
Silva et al, "Crystal Structure of the Thermostable Archaeal Intron-encoded Endonuclease I-*DmoI*", J. Mol. Biol. (1999) 286, 1123-1136.
Jurica et al, "DNA Recognition and Cleavage by the LAGLIDADG Homing Endonuclease I-CreI", Molecular Cell, Oct. 1998, vol. 2, 469-476.
Heath et al, "The structure of I-CreI, a Group intron-encoded homing endonuclease", Nature Structural Biology, Jun. 1997, vol. 4, No. 6, 468-476.
Chevalier et al, "Design, Activity, and Structure of a Highly Specific Artificial Endonuclease", Molecular Cell, Oct. 2002, vol. 10, 895-905.
U.S. Appl. No. 12/482,124, filed Jun. 10, 2009, Arnould et al.
Belfort et al., "Homing Endonucleases Keeping the House in Order," Nucleic Acids Research, 25:3379-3388 (1997).
Chevalier et al, "The Homing Endonuclease I-CreI Uses Three Metals, One of Which is Shared Between the Two Active Sites," Nat Struct Biol, 8:312-316 (2001).
Chevalier et al, "Homing Endonucleases: Structural and Functional Insight Into Catalysts of Intron/Intein Mobility," Nucleic Acids Research, 29: 3757-3774 (2001).
Choulika et al., "Induction of Homologous Recombination if Mammalian Chromosomes by Using the I-SceI System of Saccharomyces Cerevisiae," Mol Cell Biol, 15: 1968-1973 (1995).
Coffin, "Chapter 26, Retroviridae: The Viruses and their Replication," Fundamental Virology, $3^{rd}$ ed., B.N. Fields, Lippincott-Raven Publishers, Philadelphia, 1996.
Dalgaard et al., "A Site-Specific Endonuclease Encoded by a Typical Archaeal Intron," Proc Natl Acad Sci USA, 90: 5414-5417 (1993).
Dalgaard et al., "Statistical Modeling and Analysis of the LAGLIDADG Family of Site-Specific Endonuclease and Identification of an Intein that Encodes a Site-Specific Endonuclease of the HNH Family," Nucleic Acids Research, 25: 4626-4638 (1997).
Donoho et al., "Analysis of Gene Targeting and Intrachromosomal Homologous Recombination Stimulated by Genomic Double-Strand Breaks in Mouse Embryonic Stem Cells," Mol Cell Biol, 18: 4070-4078 (1998).
Duan et al., "Crystal Structure of PI-SceI, a Homing Endonuclease with Protein Splicing Activity," Cell, 89: 555-564 (1997).
Durrenberger et al., "Chloroplast Ribosomal Intron of Chlamydomonas Reinhardtil: In Vitro Self-Splicing, DNA Endonuclease Activity and in Vivo Mobility," the EMBO J, 10:3495-3501 (1991).

(Continued)

Primary Examiner — Richard Hutson
(74) Attorney, Agent, or Firm — Kenyon & Kenyon LLP

(57) ABSTRACT

This patent application relates to hybrid and/or single-chain rare-cutting endonucleases, called meganucleases, which recognize and cleave a specific nucleotide sequence, to polynucleotide sequences encoding for said rare-cutting endonucleases, to a vector comprising one of said polynucleotide sequences, to a cell or animal comprising one of said polynucleotide sequences or said rare-cutting endonucleases, to a process for producing one of said rare-cutting endonucleases and any use of the disclosed products and methods. More particularly, this invention contemplates any use of such rare-cutting endonuclease for genetic engineering and gene therapy.

15 Claims, 12 Drawing Sheets

OTHER PUBLICATIONS

Fishman-Lobell et al., "Removal of Nonhomologous DNA Ends in Double-Strand Break Recombination: The Role of the Yeast Ultra-violet Repair Gene RAD 1," Science, 258: 480-484 (1992).

Gimble et al., "Substrate Recognition and Induced DNA Distortion by the PI-SceI Endonuclease, an Enzyme Generated by Protein Splicing", J. Mol. Biol., 263:163-180 (1996).

Gimble et al., "Substitutions in Conserved Dodecapeptide motifs that Uncouple the DNA Binding and DNA Cleavage Activities of PI-SceI Endonuclease," J. Biol. Chem., 270:5849-5856 (1995).

Goguel et al., "Connections Between RNA Splicing and DNA Intron Mobility in Yeast Mitochondria: RNA Maturase and DNA Endonuclease Switching Experiments," Mol. Cell. Biol., 12: 696-705 (1992).

Haines et al., Table of Content, Current Protocol in Human Genetics, John Wiley and Sons.

Hu et al., "Probing the Structure of the PI-SceI-DNA Complex by Affinity Cleavage and Affinity Photocross-linking," J Biol Chem, 275: 2705-2712 (2000).

Iciiiyanagi et al., "Crystal Structure of an Archaeal Intein-encoded Iloming Enconuclease PI-PfuI," J Mol Biol, 300: 889-901 (2000).

Jacquier et al., "An Intron-Encoded Protein Is Active in a Gene Conversion Process That Spread an Intron into a Mitochondrial Gene," Cell, 41: 383-394 (1985).

Jurica et al., "Homing Endonucleases: Structure, Function and Evolution," Mol Cell Life Sci., 55: 1304-1326 (1999).

Kim et al., "Iiybrid Restriction Enzymes: Zinc Finger Fusions to Fok I Cleavage Domain," PNAS, 93:1156-1160 (1996).

Kim et al., "Chimeric Restriction Endonuclease," PNAS, 91: 883-887 (1994).

Lin et al., "Model for Homologous Recombination During Transfer of DNA into Mouse L Cells: Role for DNA Ends in the Recombination Process," Mol. Cell. Biol., 4: 1020-1034 (1984).

Lucas et al., "Rapid Evolution of the DNA-binding site in LAGLIDADG Homing Endonucleases," Nucleic Acids Research, 29(4): 960-969 (2001).

Lykke-Anderson et al., Mapping Metal Ions at the Catalytic Centres of Two Intron-Encoded Endonucleases, Embo J, 16: 3272-3281 (1997).

Paques et al., "Two Pathways for Removal of Nonhomologous DNA Ends During Double-Strand Break Repair in Saccharomyces Cerevisiae," Mol. Cell. Boil, 17: 6765-6771 (1997).

Poland et al., "Structural Insights into the Protein Splicing Mechanism of PI-SCcI," J Biol Chem, 275: 16408-16413 (2000).

Rouet et al., "Introduction of Double-Strand Breaks into the Genome of Mouse Cells by Expression of a Rare-Cutting Endonuclease," Mol Cell Biol, 14: 8096-8106 (1994).

Rouet et al., "Expression of a Site-Specific Endonuclease Stimulates Homologous Recombination in Mammalian Cells," Proc. Natl. Acad. Sci. USA 91: 6064-6068 (1994).

Rudin et al., "Genetic and Physical Analysis of Double-Stranded Break Repair and Recombination in Saccharomyces Cerevisiae," Genetics, 122: 519-534 (1989).

Silva et al., "Crystal Structure of the Thermostable Archael Intron-encoded Endonuclease I-Dmol," J Mol Biol, 286:1123-1136 (1999).

Smith et al., "Requirements for Double-Strand Cleavage by Chimeric Restriction Enzymes with Zinc Finger DNA-recognition Domains," Nucleic Acid Research, 28:3361-3369 (2000).

Turmel et al., "Evolutionary Conserved and Functionally Important Residues in the I-Ceul Homing Endonuclease," Nucleic Acid Research, 25: 2610-2619 (1997).

Wang et al., "Purfication, Biochemical Characterization and Protein-DNA-Interactions of the I-CreI Endonuclease Produced in Escherichia coli," Nucleic Acid Research, 25: 3767-3776 (1997).

Wenz et al., "Protein engineering of the restriction endonuclease EcoRV: replacement of an amino acid residue in the DNA binding site leads to an altered selectivity towards unmodified and modified substrates", Biochim Biophys Acta, 1219: 73-80 (1994).

Nakagawa et al., "A Maturase-like Subunit of the Sequence-specific Endanuleae SceI from Yeast Mitochonria", J. Biol. Chem, 266:1977-1984 (1991).

Kostriken et al., "A Site-Specific Endonuclease Essential for Mating-Type Switching in Saccharomyces Cerevisiae," Cell, 35: 167-174 (1983).

Lonergan et al., "The Ribosomal RNA Gene Region in Acanthamoeba castellanii Mitochondrial DNA: A Case of Evolutionary Transfer of Introns between Mitochondria and Plastids", J. Mol. Biol. 239 (4) 476-499 (1994).

Gauthier et al., "A group I intron in the chloroplast large submit rRNA gene of Chlamydomonas eugametos encodes a double- strand endonuclease that cleaves the homing site of this intron", Curr. Genet 19: 43-7 (1991).

Denovan-Wright et al., "Complete sequence of the mitochondrial DNA of Chlamydomonas eugametos", Plant Mol. Biol. 36: 285-295 (1998).

Cote, et al., "The single-group-1 intron in the chloroplast rrnL gene of Chlamydomonas humicola encodes a site-sepecific DNA endonuclease (I-ChuI)", Gene 129: 69-76 (1993).

Turmel et al., "Evolutionary Transfer of ORF-containing Group I Introns between Different Subcellular Compartments (Chloroplast and Mitocondrion)," Mol. Biol. Evol. 12: 533-545 (1995).

Rochaix et al., "The cloroplast ribosomal intron of Chalamydomonas reinhardii codes for a polypeptide related to mitochondrial maturases," NAR 13: 975-984 (1985).

Colleaux et al., "The apocytochrome b gene of Chlamydomonas smithii contains a mobile intron related to both Saccaromyces and Neurospora introns", Mol Gen Genet 223: 288-296 (1990).

Watanabe et al., "Distinctive origin of group I introns found in the COXI genes of three green algae", Gene 213:1-7 (1998).

Kjems et al., "An intron in the 23S ribosomal RNA gene of the archaebacterim Desulfurococcus mobilis", Nature, 318: 675-677 (1985).

Monteilhet et al., "Purification and characterization of the DNA cleavage and recognition site of I-ScaI mitochondrial group I Escherichia coli," Nucleic Acids Res. 28: 1245-1251 (2000).

Bonitz et al., "Assembly of the Mitochondrial Membrane System: Structure and Nucleotide Sequence of the Gene Coding for Subunit 1 of Yeast Cytochrome Oxidase*, " J. Biol. Chem. 255: 11927-11941 (1980).

Seraphin et al., "The yeast mitochondrail intron a15α: associated endonuclease activity and in vivo mobility", Gene 113: 1-8 (1992).

Everette, et al., "The Ribosomal Intergenic Spacer and Domain I of the 23S rRNA gene Are Phylogenetic Markers for Chlamydia spp.," Int. J. Syst. Bacteriol. 47 (2) 461-473 (1997).

Deckert, G. et al., "The complete genome of the hyperthermophilic bacterium Aquifex aeolicus", Nature 392 (6674) 353-358 (1998).

Kawarabayasi, Y. et al., "Complete Genome Sequence of an Aerobic Hyper-thermophilic Crenarchaeon, Aeropyrum perinix K1," DNA Res. 6 (2), 83-101 (1999).

http://bioinformatics.weizmann.ac.il/~pietro/inteins (2001).

Gu et al., "Peptide Splicing in the Vacular ATPase Subunit a from Candida tropicalis", J. Biol. Chem. 268: 7372-7381 (1993).

Davis et al., "Evidence of selection for protein introns in the RecAs of pathogenic mycobacteria," EMBO J., 13(3):699-703 (1994).

Davis et al., "Protein Splicing in the Mauration of M. tuberculosis RecA Protein : A Mechanism for Tolerating a Novel Class of Intervening Sequence", Cell, 71(2):201-210 (1992).

Komori et al., "PI-PfuI and PI-PfuII, intein-coded homing endonucleases from Pyrococcus furiosus. I. Purification and identification of the homing-type endonuclease activities," Nucleic Acid Research, 27: 4167-4174 (1999).

Takagi et al., "Characterization of DNA Polymerase from Pyrococcus sp. Strain KOD1 and Its Application to PCR," Appl. Environ. Microbiol. 63: 4504-4510 (1997).

Xu, et al., "In Vitro Protein Splicing of Purified Precursor and the Identification of Branched intermediate", Cell 75: 1371-1377 (1993).

Liu et al., "A DnaB intein in Rhodothermus marinus: Indication of recent intein homing across remotely related organisms," PNAS 94: 7851-7856 (1997).

Hirata, R. et al., "Molecular Structure of a Gene, VMA1, Encoding the Catalytic Subunit of II$^+$-Translocating Adenosine Triphosphatase from Vacuolar Membranes of Saccharomyces cerevisiae*" J. Biol. Chem. 265: 6726-6733 (1990).

Lazarevic, et al., "Introns and intein coding sequence in the ribonucleotide reductase genes of *Bacillus subtilis* temperate bacteriophage SPβ", PNAS 95: 1692-1697 (1998).

Saves et al., "Inteins of *Thermococcus fumicolans* DNA Polymerse Are Endonucleases with Distinct Enzymatic Behaviors", J. Biol. Chem., 275: 2335-2341 (2000).

Perler et al., "Intervening sequences in an Archaea DNA polymerase gene", PNAS 89:5577-5581 (1992).

Lambowitz et al., "Introns as Mobile Genetic Elements" Annu Rev Biochem 62: 587-622 (1993).

* cited by examiner

*Figure 3*A
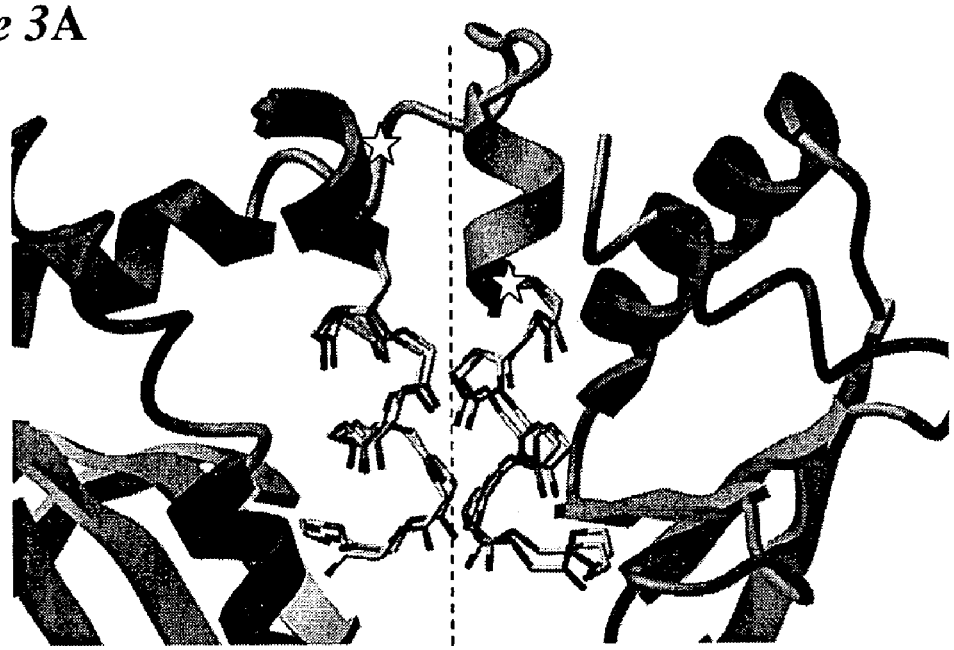
Figure 3B
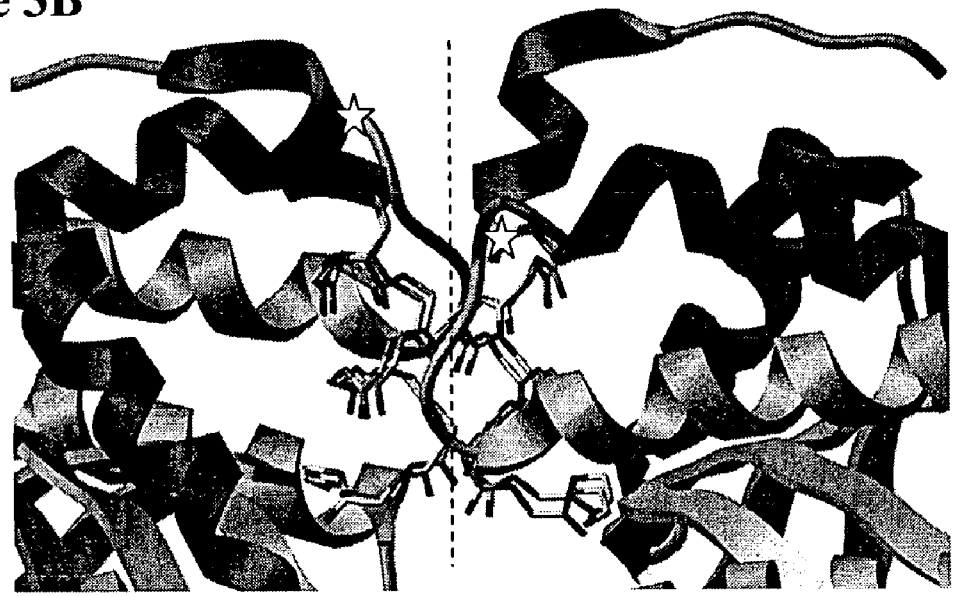

Amino acid Sequence of a hybrid I-Dom I/ I-Cre I A

```
  1 MAHNNENVSG ISAYLLGLII GDGGLYKLKY KGNRSEYRVV ITQKSENLIK
 51 QHIAPLMQFL IDELNVKSKI QIVKGDTRYE LRVSSKKLYY YFANMLERIR
101 LFNMREQLAFHLAGFVDGDGS IIAQIKPNQS YKFKHQLSLT FQVTQKTQRR
151 WFLDKLVDEI GVGYVRDRGS VSDYILSEIK PLHNFLTQLQ PFLKLKQKQA
201 NLVLKIIEQL PSAKESPDKF LEVCTWVDQI AALNDSKTRK TTSETVRAVL
251 DSLSEKKKSS PAAD
```

Polynucleotide sequence encoding the hybrid I-Dom I/ I-Cre I A

```
  1 ATGGCCCATA ACAATGAGAA CGTTTCTGGT ATCTCCGCTT ACCTGCTGGG
 51 CCTGATTATC GGTGATGGTG GCCTGTACAA GCTGAAATAT AAAGGTAACC
101 GTAGCGAATA TCGTGTTGTG ATCACCCAGA AGTCTGAAAA CCTGATTAAA
151 CAACACATCG CACCGCTGAT GCAGTTTCTG ATTGATGAAC TGAATGTGAA
201 ATCTAAAATC CAGATCGTTA AGGGTGATAC CCGCTATGAG CTGCGTGTGA
251 GCTCTAAGAA ACTGTACTAT TACTTCGCTA ACATGCTGGA GCGTATCCGC
301 CTGTTCAACA TGCGTGAGCA GCTGGCGTTC CTGGCCGGCT TTGTGGACGG
351 TGACGGTAGC ATCATCGCTC AGATTAAACC AAACCAGTCT TATAAATTCA
401 AGCATCAGCT GTCCCTGACC TTTCAGGTGA CTCAAAAGAC CCAGCGCCGT
451 TGGTTTCTGG ACAAACTGGT GGATGAAATT GGCGTTGGTT ACGTACGTGA
501 TCGCGGTAGC GTTTCCGATT ACATTCTGAG CGAAATCAAG CCGCTGCACA
551 ACTTCCTGAC TCAACTGCAA CCGTTTCTGA AACTGAAACA GAAACAGGCA
601 AACCTGGTTC TGAAAATTAT CGAACAGCTG CCGTCTGCAA AAGAATCCCC
651 GGACAAATTC CTGGAAGTTT GTACCTGGGT GGATCAGATT GCAGCTCTGA
701 ACGATTCTAA GACGCGTAAA ACCACTTCTG AAACCGTTCG TGCTGTGCTG
751 GACAGCCTGA GCGAGAAGAA GAAATCCTCC CCGGCGGCCG ACTAG
```

Figure 6A

Amino acid Sequence of a hybrid I-Dom I/ I-Cre I B

```
  1 MAHNNENVSG ISAYLLGLII GDGGLYKLKY KGNRSEYRVV ITQKSENAIK
 51 QAIAPDMQFL IDELNVKSKI QIVKGDTRYE LRVSSKKLYY YFANMLERIR
101 LFNMREQLAFHLAGFVDGDGS IIAQIKPNQS YKFKHQLSLT FQVTQKTQRR
151 WFLDKLVDEI GVGYVRDRGS VSDYILSEIK PLHNFLTQLQ PFLKLKQKQA
201 NLVLKIIEQL PSAKESPDKF LEVCTWVDQI AALNDSKTRK TTSETVRAVL
251 DSLSEKKKSS PAAD
```

Polynucleotide sequence encoding the hybrid I-Dom I/ I-Cre I B

```
  1 ATGGCCCACA ACAATGAGAA TGTGTCTGGC ATCTCTGCCT ACCTGCTGGG
 51 CCTCATCATT GGAGATGGAG GTCTGTACAA ACTTAAGTAC AAAGGCAACA
101 GGTCTGAGTA CAGAGTGGTC ATCACCCAGA AGTCTGAAAA TgctATCAAG
151 CAAgctATTG CTCCAgatAT GCAGTTCCTG ATTGATGAAC TCAATGTCAA
201 GAGCAAGATC CAGATTGTCA AAGGTGACAC TAGATATGAG CTGAGAGTTT
251 CCTCCAAGAA ACTTTACTAT TACTTTGCCA ACATGTTGGA GAGGATCAGG
301 CTGTTCAATA TGAGGGAGCA ActgGCCTTC CTTGCTGGAT TTGTGGATGG
351 TGATGGCTCC ATCATTGCTC AGATAAAACC AAATCAATCT TACAAGTTCA
401 AACACCAGCT CTCCTTGACC TTTCAAGTCA CTCAGAAGAC ACAAAGAAGG
451 TGGTTCTTGG ACAAATTGGT TGATGAGATT GGTGTGGGCT ATGTCAGAGA
501 CAGAGGCTCT GTGTCAGACT ACATCCTGTC TGAAATTAAG CCTCTTCATA
551 ACTTTCTCAC CCAACTGCAA CCCTTCTTGA AGCTCAAACA GAAGCAAGCA
601 AATCTGGTTT TGAAAATCAT TGAACAGCTG CCATCTGCCA AGGAGTCCCC
651 TGACAAGTTT CTTGAAGTGT GTACTTGGGT GGATCAGATT GCTGCCTTGA
701 ATGACTCCAA GACCAGAAAA ACCACCTCTG AGACTGTGAG GGCAGTTCTG
751 GATAGCCTCT CTGAGAAGAA AAAGTCCTCT CCTGCGGCCG ACTAG
```

Figure 6B

Amino acid sequence of a Single chain I-Cre I

```
  1 MANTKYNKEF LLYLAGFVDG DGSIIAQIKP NQSYKFKHQL SLTFQVTQKT
 51 QRRWFLDKLV DEIGVGYVRD RGSVSDYILS EIKPLHNFLT QLQAMLERIR
101 LFNMREFLLY LAGFVDGDGS IIAQIKPNQS YKFKHQLSLT FQVTQKTQRR
151 WFLDKLVDEI GVGYVRDRGS VSDYILSEIK PLHNFLTQLQ PFLKLKQKQA
201 NLVLKIIEQL PSAKESPDKF LEVCTWVDQI AALNDSKTRK TTSETVRAVL
251 DSLSEKKKSS PAAD
```

Polynucleotide sequence ecoding the Single chain I-Cre I

```
  1 ATGGCCAACA CTAAGTACAA TAAAGAATTT CTCCTGTATC TGGCAGGTTT
 51 CGTCGACGGC GATGGCTCCA TTATCGCACA GATCAAGCCG AATCAGAGCT
101 ACAAGTTTAA ACACCAACTG TCTCTCACTT TCCAGGTTAC CCAGAAAACT
151 CAACGTCGCT GGTTCCTGGA TAAGCTGGTA GATGAGATCG GTGTGGGCTA
201 TGTACGCGAC CGTGGCTCTG TGAGCGACTA TATCCTGTCT GAGATTAAAC
251 CACTGCATAA TTTTCTGACC CAGCTGCAGG CTATGCTGGA GCGTATCCGT
301 CTGTTCAACA TGCGTGAGTT CCTGCTGTAC CTGGCCGGCT TTGTGGACGG
351 TGACGGTAGC ATCATCGCTC AGATTAAACC AAACCAGTCT TATAAATTCA
401 AGCATCAGCT GTCCCTGACC TTTCAGGTGA CTCAAAAGAC CCAGCGCCGT
451 TGGTTTCTGG ACAAACTGGT GGATGAAATT GGCGTTGGTT ACGTACGTGA
501 TCGCGGTAGC GTTTCCGATT ACATTCTGAG CGAAATCAAG CCGCTGCACA
551 ACTTCCTGAC TCAACTGCAA CCGTTTCTGA AACTGAAACA GAAACAGGCA
601 AACCTGGTTC TGAAAATTAT CGAACAGCTG CCGTCTGCAA AGAATCCCC
651 GGACAAATTC CTGGAAGTTT GTACCTGGGT GGATCAGATT GCAGCTCTGA
701 ACGATTCTAA GACGCGTAAA ACCACTTCTG AAACCGTTCG TGCTGTGCTG
751 GACAGCCTGA GCGAGAAGAA GAAATCCTCC CCGGCGGCCG ACTAG
```

Figure 7 hybrid I-*Dmo*I/I-*Cre*I
I-*Dmo*I

Trp1, cen

Leu2, 2μ

HYBRID AND SINGLE CHAIN MEGANUCLEASES AND USE THEREOF

The present application is based on and claims benefit of U.S. application Ser. No. 60/364,113, filed Mar. 15, 2002, the entire contents of which is incorporated herein by reference.

BACKGROUND

1. Field of the Invention

This patent application relates to hybrid and/or single-chain rare-cutting endonucleases, called meganucleases, which recognize and cleave a specific nucleotide sequence, to polynucleotide sequences encoding for said rare-cutting endonucleases, to a vector comprising one of said polynucleotide sequences, to a cell or animal comprising one of said polynucleotide sequences or said rare-cutting endonucleases, to a process for producing one of said rare-cutting endonucleases and any use of the disclosed products and methods. More particularly, this invention contemplates any use of such rare-cutting endonuclease for genetic engineering and gene therapy.

2. Brief Description of the Prior Art

Meganucleases constitute a family of very rare-cutting endonucleases. It was first characterised at the beginning of the Nineties by the use (in vivo) of the protein I-Sce I (Omega nuclease, originally encoded by a mitochondrial group I intron of the yeast *Saccharomyces cerevisice*). Homing endonucleases encoded by introns ORF, independent genes or intervening sequences (inteins) are defined now as "meganucleases", with striking structural and functional properties that distinguish them from "classical" restriction enzymes (generally from bacterial system R/MII). They have recognition sequences that span 12-40 bp of DNA, whereas "classical" restriction enzymes recognise much shorter stretches of DNA, in the 3-8 bp range (up to 12 bp for rare-cutter). Therefore, the meganucleases present a very low frequency of cleavage, even in the human genome.

Furthermore, general asymmetry of Meganucleases target sequences contrasts with the characteristic dyad symmetry of most restriction enzyme recognition sites. Several Meganucleases encoded by introns ORF or inteins have been shown to promote the homing of their respective genetic elements into allelic intronless or inteinless sites. By making a site-specific double-strand break in the intronless or inteinless alleles, these nucleases create recombinogenic ends, which engage in a gene conversion process that duplicates the coding sequence and leads to the insertion of an intron or an intervening sequence at the DNA level.

Meganucleases fall into 4 separated families on the basis of pretty well conserved amino acids motifs. One of them is the dodecapeptide family (dodecamer, DOD, D1-D2, LAGLIDADG, P1-P2). This is the largest family of proteins clustered by their most general conserved sequence motif: one or two copies (vast majority) of a twelve-residue sequence: the di-dodecapeptide. Meganucleases with one dodecapetide (D) are around 20 kDa in molecular mass and act as homodimer. Those with two copies (DD) range from 25 kDa (230 AA) to 50 kDa (HO, 545 AA) with 70 to 150 residues between each motif and act as monomer. Cleavage is inside the recognition site, leaving 4 nt staggered cut with 3'OH overhangs. I-Ceu I, and I-Cre I illustrate the meganucleases with one Dodecapeptide motif (mono-dodecapeptide). I-Dmo I, I-Sce I, PI-Pfu I and PI-Sce I illustrate meganucleases with two Dodecapeptide motifs.

Goguel et al (*Mol. Cell. Biol.*, 1992, 12, 696-705) shows by switching experiments of RNA maturase and meganuclease of yeast mitochondria that the meganuclease badly tolerates sequence switching and loses its endonuclease activity.

Endonucleases are requisite enzymes for today's advanced gene engineering techniques, notably for cloning and analyzing genes. Meganucleases are very interesting as rare-cutter endonucleases because they have a very low recognition and cleavage frequency in large genome due to the size of their recognition site. Therefore, the meganucleases are used for molecular biology and for genetic engineering, more particularly according to the methods described in WO 96/14408, U.S. Pat. No. 5,830,729, WO 00/46385, and WO 00/46386.

Up to now, in a first approach for generating new endonuclease, some chimeric restriction enzymes have been prepared through hybrids between a zinc finger DNA-binding domain and the non-specific DNA-cleavage domain from the natural restriction enzyme Fok I (Smith et al, 2000, Nucleic Acids Res, 28, 3361-9; Kim et al, 1996, Proc Natl Acad Sci USA, 93, 1156-60; Kim & Chandrasegaran, 1994, Proc Natl Acad Sci USA, 91, 883-7; WO 95/09233; WO 94/18313).

An additional approach consisted of an alteration of the recognition domain of EcoRV restriction enzyme in order to change its specificity by site-specific mutagenesis (Wenz et al, 1994, Biochim Biophys Acta, 1219, 73-80).

Despite these efforts, there is still a strong need for new rare-cutting endonucleases with new sequence specificity for the recognition and cleavage.

SUMMARY

The invention concerns a hybrid meganuclease comprising a first domain and a second domain, said first and second domains being derived from two different initial LAGLIDADG (SEQ ID NO:17) meganucleases, said initial meganucleases being either mono- or di-LAGLIDADG (SEQ ID NO:17) meganucleases. The invention also contemplates a hybrid meganuclease comprising two domains, each domain being derived from the same meganuclease and said two domains having a different arrangement than the initial meganuclease (i.e. the second domain is derived from the N-terminal domain of the initial meganuclease and/or the first domain is derived from the C-terminal of the initial meganuclease).

The invention also concerns a single-chain meganuclease comprising a first domain and a second domain, said first and second domains being derived from an initial mono-LAGLIDADG (SEQ ID NO:17) meganuclease.

The invention further concerns any polynucleotide encoding a hybrid or single-chain meganuclease according to the present invention and vectors, cells or non-human animals comprising such a polynucleotide.

The invention concerns any use of a hybrid or single-chain meganuclease according to the present invention or a polynucleotide encoding it for molecular biology, genetic engineering and gene therapy.

BRIEF DESCRIPTION OF THE DRAWINGS

FIGS. 3A and 3B respectively are ribbon representations of I-DmoI and I-CreI in the region of the dodecapeptide motifs. For both proteins, the main chain atoms of residues corresponding to the dodecapeptide motifs are shown in stick representation, together with the superimposed atoms from the other protein. The discontinuous line represents the two-fold symmetry axis between the two protein domains. Stars represent, in FIG. 3A, the limits of the linkers between the I-DmoI domains and in FIG. 3B the corresponding positions in I-CreI where that linker is to be engineered. Orientations of the proteins are as in FIGS. 1 and 2.

(FIG. 5A) The stars indicate where the linker is to be introduced; three α-helices in the first monomer (following the left-most star) are removed in the single chain, together with the N-terminal residues of the second monomer (prior to the other star). (FIG. 5B) The loop joining both domains, comprised between the two stars, is taken from I-DmoI (structure 1b24). The grey disk represent the symmetry axis (orientation is from the top of the structures, e.g.cpmpared to the previous figures, it was rotated by 90° around an horizontal axis).

FIGS. 6A and 6B disclose the amino acid sequence of two alternatives of hybrid meganuclease I-Dmo I/I-Cre I and a polynucleotide sequence encoding each alternative. Underlined residues are the LAGLI-DADG motifs. In bold, residues within the I-DmoI domain that are mutated are shown. The "H" indicates the swap point, at the boundary between the I-DmoI and I-CreI domains. In all protein sequences, the two first N-terminal residues are methionine and alanine (MA), and the three C-terminal residues alanine, alanine and aspartic acid (AAD). These sequences allow having DNA coding sequences comprising the NcoI (CCATGG) and EagI (CG-GCCG) restriction sites, which are used for cloning into various vectors. The alternative A just presents a swapping point whereas the alternative B has three additional mutations avoiding potential hindrance.

FIG. 7 discloses the amino acid sequence of an alternative of a single chain I-Cre I and one polynucleotide encoding said single chain meganuclease. In the protein sequence, the two first N-terminal residues are methionine and alanine (MA), and the three C-terminal residues alanine, alanine and aspartic acid (AAD). These sequences allow having DNA coding sequences comprising the NcoI (CCATGG) and EagI (CG-GCCG) restriction sites, which are used for cloning into various vectors.

FIG. 8 shows the In vitro cleavage assay for the hybrid meganuclease I-Dmo I/I-Cre I (FIG. 8B) and the SDS-PAGE gel with such hybrid (FIG. 8A).

FIG. 9 shows the In vitro cleavage assay for the single chain meganuclease I-Cre I (FIG. 9B) and the SDS-PAGE gel of the gel filtration with such single chain meganuclease (FIG. 9A).

DETAILED DESCRIPTION

Definitions

Figure 1:
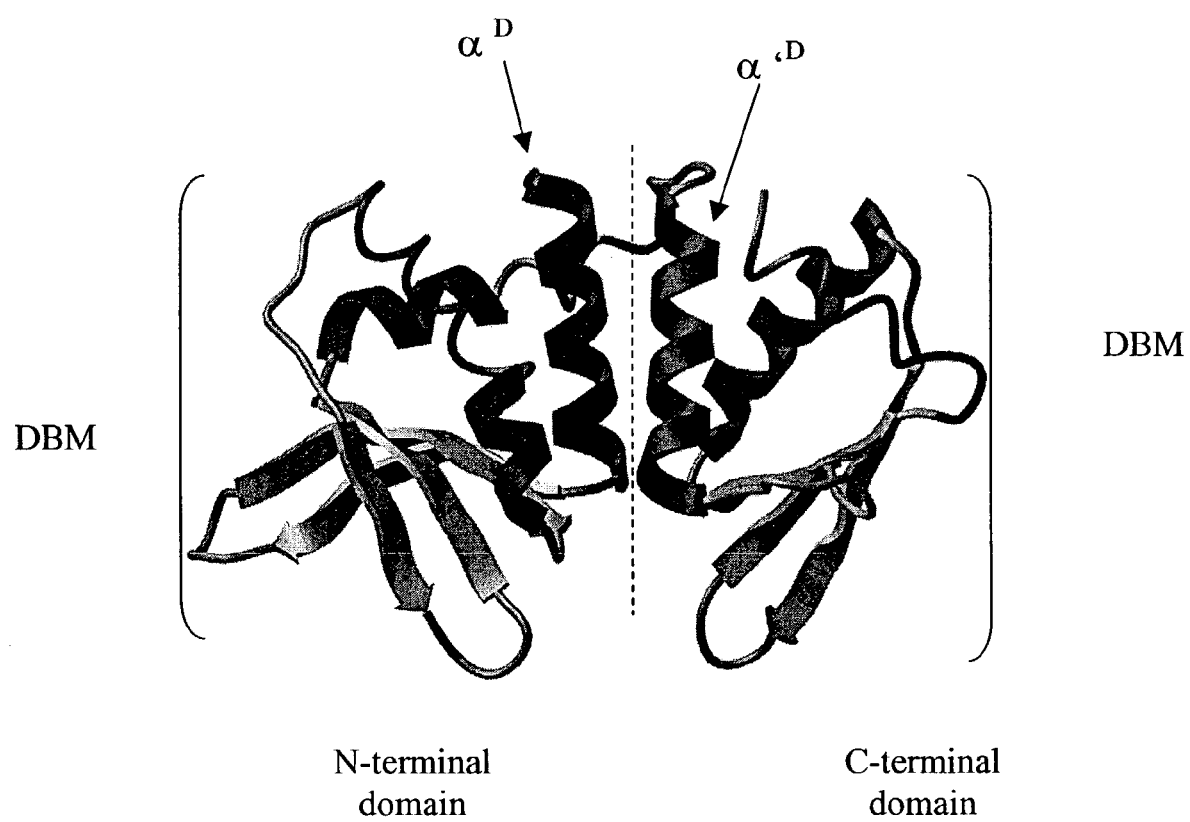
FIG. 1 is a ribbon representation of I-DmoI (pdb code 1b24). The discontinuous line represents the two-fold pseudo-symmetry axis between the two domains. The N-terminal domain of I-DmoI is left of that axis, and the C-terminal domain is on the right side. DNA (not present in structure 1b24) should bind perpendicular to the symmetry axis below the two β-sheets (arrows). $\alpha^D$ and $\alpha'^D$ refer to helices comprising the dodecapeptide motif, DBM to DNA binding moiety, and V to variable sequence.

In the present application, by "meganuclease" is intended a rare-cutting endonuclease, typically having a polynucleotide recognition site of about 12-40 bp in length, more preferably of 14-40 bp. Typical meganucleases cause cleavage inside their recognition site, leaving 4 nt staggered cut with 3'OH overhangs. The meganuclease are also commonly called homing endonuclease. Preferably, "meganucleases" according to the present invention belong to the dodecapeptide family (LAGLIDADG). For more information on meganucleases, see Dalgaard et al (1997, *Nucleic Acids Resarch*, 25, 4626-4638) and Chevalier and Stoddard (2001, *Nucleic Acids Resarch*, 29, 3757-3774). Specific examples of LAGL-IDADG meganucleases are listed in Table 1.

By "helix" or "helices" is intended in the present invention α-helix or α-helices. $\alpha^D$ and $\alpha^{LAGLIDADG}$ in the present invention refers to the helix comprising the LAGLIDADG, DOD or dodecapeptide motif.

By "derived" is intended that the domain comprises the sequence of a domain of the meganuclease from which the domain is derived. Said sequence of a domain can comprise some modifications or substitutions.

A "target site" or recognition and/or cleavage site as used herein, refers to a polynucleotide sequence bound and cleaved by a meganuclease.

The term "recombinant polypeptide" is used herein to refer to polypeptides that have been artificially designed and which comprise at least two polypeptide sequences that are not found as contiguous polypeptide sequences in their initial natural environment, or to polypeptides which have been expressed from a recombinant polynucleotide.

As used herein, the term "individual" includes mammals, as well as other animals (e. g., birds, fish, reptiles, insects). The terms "mammal" and "mammalian", as used herein, refer to any vertebrate animal, including monotremes, marsupials and placental, that suckle their young and either give birth to living young (eutharian or placental mammals) or are egg-laying (metatharian or nonplacental mammals).

Examples of mammalian species include humans and other primates (e. g., monkeys, chimpanzees), rodents (e. g., rats, mice, guinea pigs) and ruminents (e. g., cows, pigs, horses).

The term "reporter gene", as used herein, refers to a nucleic acid sequence whose product can be easily assayed, for example, colorimetrically as an enzymatic reaction product, such as the lacZ gene which encodes for—galactosidase. Examples of widely-used reporter molecules include enzymes such as β-galactosidase, β-glucoronidase, β-glucosidase; luminescent molecules such as green fluorescent protein and firefly luciferase; and auxotrophic markers such as His3p and Ura3p. (See, e. g., Chapter 9 in Ausubel, F. M., et al. Current Protocols in Molecular Biology, John Wiley & Sons, Inc. (1998)).

As used interchangeably herein, the terms "nucleic acid" "oligonucleotide", and "polynucleotide" include RNA, DNA, or RNA/DNA hybrid sequences of more than one nucleotide in either single chain or duplex form. The term "polynucleotide" refers to a polymer of units comprising a purine or pyrimidine, a ribose or deoxyribose sugar moiety, and a phosphate group, or phosphodiester linkage. "polynucleotides" also refers to polynucleotide comprising "modified nucleotides" which comprise at least one of the following modifications (a) an alternative linking group, (b) an analogous form of purine, (c) an analogous form of pyrimidine, or (d) an analogous sugar.

Endonuclease: By "endonuclease" is intended an enzyme capable of causing a double-stranded break in a DNA molecule at highly specific locations.

"Cells," or "host cells", are terms used interchangeably herein. It is understood that such terms refer not only to the particular subject cell but to the progeny or potential progeny of such a cell. Because certain modifications may occur in succeeding generations due to either mutation or environmental influences, such progeny may not be identical to the parent cell, but are still included within the scope of the term as used herein.

"Identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default settings.

The "non-human animals" of the invention include mammalians such as rodents, non-human primates, sheep, dog, cow, chickens, amphibians, reptiles, etc. Preferred non-human animals are selected from the rodent family including rat and mouse, most preferably mouse, though transgenic amphibians, such as members of the Xenopus genus, and transgenic chickens, cow, sheep can also provide important tools.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". A vector according to the present invention comprises, but is not limited to, a YAC (yeast artificial chromosome), a BAC (bacterial artificial), a baculovirus vector, a phage, a phagemid, a cosmid, a viral vector, a plasmid, a RNA vector or a linear or circular DNA or RNA molecule which may consist of a chromosomal, non chromosomal, semi-synthetic or synthetic DNA. In general, expression vectors of utility in recombinant DNA techniques are often in the form of "plasmids" which refer generally to circular double stranded DNA loops which, in their vector form are not bound to the chromosome. Large numbers of suitable vectors are known to those of skill in the art and commercially available, such as the following bacterial vectors: pQE70, pQE60. pQE-9 (Qiagen), pbs, pDlO, phagescript, psiXl74. pbluescript SK. pbsks. pNH8A. pNH16A, pNH18A, pNH46A (Stratagene); ptrc99a, pKK223-3, pKK233-3, pDR540, pRIT5 (Pharmacia); pWLNEO. pSV2CAT, pOG44, pXT1, pSG (Stratagene); pSVK3, pBPV, pMSG, pSVL (Pharmacia); pQE-30 (QIAexpress).

Viral vectors include retrovirus, adenovirus, parvovirus (e. g., adenoassociated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double stranded DNA viruses including adenovirus, herpesvirus (e. g., Herpes Simplex virus types 1 and 2, Epstein-Barr virus, cytomegalovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, Dtype viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in McVey et al., U.S. Pat. No. 5,801,030, the teachings of which are incorporated herein by reference.

Vectors can comprise selectable markers (for example, neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase for eukaryotic cell culture; TRP1 for *S. cerevisiae*; tetracycline, rifampicin or ampicillin resistance in *E. coli*; etc . . . ). However, the invention is intended to include such other forms of expression vectors which serve equivalent functions and which become known in the art subsequently hereto.

Flanked: A polynucleotide to be linearized or excised is flanked by a cleavage site if such a site is present at or near either or both ends of the polynucleotide. There can be one cleavage site present or near one end of the polynucleotide to be linearized or excised or there can be two cleavage sites, one at or near each end of the polynucleotide to be linearized or excised. By "near" is preferably intended in the present invention that the cleavage site is located at less than 1 kb, preferably less than 500 bp, more preferably less than 200, or 100 bp, of the end of the polynucleotide to be integrated.

The present invention relates to new designed rare-cutting endonucleases and use thereof. These new designed rare-cutting endonucleases are preferably derived from the meganuclease family of "dodecapeptide" LAGLIDADG.

Hybrid Meganucleases

Meganucleases form a class of over 200 rare-cutting double-stranded DNA endonucleases (group I intron homing endonucleases and inteins) (Belfort and Roberts, 1997, *Nucleic Acids Res*, 25, 3379-3388; Jurica and Stoddard, 1999, *Cell Mol Life Sci*, 55, 1304-1326). They recognize asymmetrical DNA sequences that are between 14 and 40 base pairs in length, producing double-strand breaks at about the center of their target sequence. Said target site is defined herein as the sum of two different half-sites. In complex DNA, 16 (and over) nucleotides-long DNA sequences can be expected to be unique, even in a genome the size of the human genome ($3 \times 10^9$ base pairs). Meganucleases will thus cut cellular genomes only once, at the target locus.

The LAGLIDADG protein family is characterized by the presence of one or two copies of a well-conserved sequence motif, termed dodecapeptide, or P1 and P2, LAGLI and DADG or LAGLIDADG. Outside of those motifs, there is no relevant sequence homology (overall pairwise sequence homologies are below 25%). The smaller examples, i.e. I-CreI (Durrenberger and Rochaix, 1991, *Embo J*, 10, 3495-3501), have only one dodecapeptide motif and function as homodimers of two 15-20 kDa subunits or domains. These proteins having only one dodecapeptide motif are called in the present application as "mono-dodecapeptide" proteins. Larger proteins, i.e. I-DmoI (Dalgaard et al., 1993, *Proc Natl Acad Sci USA*, 90, 5414-5417), I-SceI (Jacquier et Dujon, 1985, *Cell*, 41, 383-394) and PI-SceI (Gimble and Wang, 1996, *J Mol Biol*, 263, 163-180), on the other hand, are single-chain proteins (20-30 kDa) bearing two (non-identical) dodecapeptide motifs. These proteins having two dodecapeptide motifs are called in the present application as "di-dodecapeptide" proteins.

Detailed three-dimensional structures (Chevalier et al., 2001, *Nat Struct Biol*, 8, 312-316; Duan et al., 1997, *Cell*, 89, 555-564; Heath et al., 1997, *Nat Struct Biol*, 4, 468-476; Hu et al., 2000, *J Biol Chem*, 275, 2705-2712; Ichiyanagi et al., 2000, *J Mol Biol*, 300, 889-901; Jurica et al., 1998, *Mol Cell*, 2, 469-476; Poland et al., 2000, *J Biol Chem*, 275, 16408-16413; Silva et al., 1999, *J Mol Biol*, 286, 1123-1136), have been solved for four LAGLIDADG proteins: I-CreI (FIG. 1), I-DmoI (FIG. 2), PI-SceI and PI-PfuI. These structures illustrate that the dodecapeptide motifs are part of a two-helix bundle. The two α-helices form most of the central interface, where a two-fold (pseudo-) symmetry axis separates two structural domains. In addition to the dodecapeptide motif, each domain presents a DNA binding interface that drives the protein towards interacting with one of the two half sites of the target DNA sequence.

A unique catalytic, active site comprises amino acid residues from both structural domains, whose specific nature and spatial distribution is required for DNA cleavage. In the LAGLIDADG protein family, the residues in the active sites are divergent. The only residues that display persistent conservation are the last acidic amino acids (D or E) from both LAGLIDADG motifs (underlined residue). Therefore, it is difficult to assign functional roles to residues in the active site, except for those acidic amino acids. Mutations of those residues abolish catalysis, but not DNA binding (Lykke-Andersen et al., 1997, *Embo J*, 16, 3272-3281; Gimble & Stephens, 1995, *J. Biol. Chem.*, 270, 5849-5856). Besides, a hydration shell, consisting of several water molecules structurally organized by the amino acid side chains of acidic and basic residues, together with divalent cations, has probably an essential role in conducting the cleavage of DNA phosphodiester bonds (Chevalier et al., 2001, *Nat Struct Biol*, 8, 312-316).

Engineering known meganucleases, in order to modify their specificity towards DNA sequences could allow targeting of new DNA sequences, and to produce double-strand breaks in chosen genes.

However, residues related to the inter-domain packing interface and the catalytic site are very constrained. It is known that the catalytic domains of enzymes are often complex and highly reactive to modifications. In the case of the meganucleases, this sensibility to modification is increased, as the catalytic site is constituted by the interface of two domains. Consequently, it is not known whether domain swapping of meganucleases, which have distinct catalytic site residues, would restore functional, active proteins. Moreover, despite the domain structure of known meganucleases, particularly those of the LAGLIDADG protein family, nothing is known about the modular behaviour of such domain structure.

For the first time, the present invention shows that LAGLIDADG endonucleases are modular and that domain swapping of natural homing endonucleases or meganucleases is both possible and fruitful: novel, artificial combinations of two domains taken from different LAGLIDADG meganucleases recognize, bind and cut DNA sequences made of the corresponding two half-sites. Engineering such artificial combinations (hybrid or chimerical homing endonucleases or meganucleases) is primarily useful in order to generate meganucleases with new specificity.

The LAGLIDADG protein family essentially shows a sequence conservation in the dodecapeptide motifs. The 3D structure are similar: they have the same set of secondary structure elements organized with a unique topology. Conservation of the dodecapeptide motif and protein size (in particular, the separation distance in sequence length between two dodecapeptide motifs in di-dodecameganuclease together with the biological relationships, i.e. same "function" and conserved 3D architecture) are thought sufficient to propose that the secondary structure is conserved.

The present invention concerns the novel endonucleases, more particularly hybrid meganucleases, preferably derived from at least two different LAGLIDADG meganucleases. The initial meganucleases can be "mono-dodecapeptide" or "mono-LAGLIDADG", such as I-Cre I meganuclease, or "di-dodecapeptide" or "di-LAGLIDADG" meganucleases such as I-Dmo I. These new designed endonucleases or meganucleases are hybrid of LAGLIDADG meganucleases. The invention concerns a hybrid meganuclease comprising two domains, each domain being derived from a different LAGLIDADG meganuclease. See Table 1 (Motif "D" refers to mono-dodecapeptide meganucleases and motif "dd" or "DD" to di-dodecapeptide meganucleases). The invention also contemplates a hybrid meganuclease comprising two domains, each domain being derived from the same meganuclease but in a different arrangement (e.g., location, organization, position, etc.) as compared to the initial meganuclease (e.g., the second domain is derived from the N-terminal domain of the initial meganuclease and/or the first domain is derived from the C-terminal of the initial meganuclease).

By "domain" of LAGLIDADG meganucleases is intended in the present invention a polypeptide fragment comprising or consisting of a dodecapeptide motif and a DNA binding moiety. Optionally, the domain can also comprise additional polypeptide sequences not involved in the DNA binding nor in the domain interface. However, those additional sequences have variable size and are generally not critical for the DNA recognition and binding nor the endonuclease activity. The dodecapeptide motif is involved in an α-helix, herein schematically called $\alpha^{LAGLIDADG}$ or $\alpha^D$. In more detail, the last D(E) residue is generally capping the α-helix and the following Gly residue initiates a main chain redirection into a β-strand perpendicular to the α-helix. The DNA binding moiety, herein schematically called DBM, generally comprises α-helices and β-strands. The minimal DNA binding moiety in a meganuclease is a β-hairpin (2 β-strands connected by a loop or turn). Natural meganucleases comprise two such β-hairpins in each DNA binding moiety, connecting into a 4-stranded β-sheet. The connecting between the two β-hairpins comprises an α-helix. The DNA binding moiety generally comprises a further α-helix dowstream of the 4-stranded β-sheet. The additional polypeptide sequences could be found at each side of the group consisting of the dodecapeptide motif and the DNA binding moiety. Therefore, a meganuclease domain according to the present invention comprises the helix comprising the dodecapeptide motif, $\alpha^D$, and a DNA binding moiety, DBM. Optionally, an additional sequence can be further comprised in said domain. Said additional sequence is possible at the N-terminal side of a first domain of the hybrid meganuclease or at the C-terminal side of a second domain of the hybrid meganuclease.

The LAGLIDADG meganucleases comprising two dodecapeptide motifs, herein called di-LAGLIDADG meganuclease, comprise two domains, one domain called N-terminal domain and the other C-terminal domain. The N-terminal domain consecutively comprises an additional optional sequence, the dodecapeptide motif and the DNA binding moiety. The C-terminal domain consecutively comprises the dodecapeptide motif, the DNA binding moiety and an additional optional sequence. The two dodecapeptide α-helices of each domain form a tightly packed domain interface. The loop connecting the two domains is between the DNA binding moiety of the N-terminal domain and the helix comprising the second dodecapeptide motif of the C-terminal domain. The di-dodecapeptide meganucleases could schematically be represented by the following structure from the N-terminal end to the C-terminal end: V $\alpha^D$ DBM (L) $\alpha^{D}$ DBM' V' (V refering to additional optional sequence, $\alpha^D$ to the helix comprising the dodecapeptide motif, DBM to the DNA binding moiety, L to the connecting loop; the ' refers to the elements of the C-terminal domain). The helices $\alpha^D$ and $\alpha^{D}$ correspond to the helices comprising the dodecapeptide motifs. The domains of a meganuclease comprising two dodecapeptide motifs are asymmetric (similar but generally not identical). Number of di-dodecapeptide meganucleases are known. See Table 1, Motif "dd" or "DD". (Also see, Dalgaard et al., 1993, *Proc Natl Acad Sci USA*, 90, 5414-5417, Table 1 and FIG. 1)

The dimeric LAGLIDADG meganucleases comprising one dodecapeptide motif, herein called mono-dodecapeptide meganucleases, consecutively comprises an additional optional polypeptide sequence, the dodecapeptide motif, the DNA binding moiety, and an additional optional polypeptide sequence. The two dodecapeptide helices (one in each monomer) form a tightly packed dimer interface. The mono-dodecapeptide meganucleases could schematically be represented by the following structure comprising from the N-terminal end to the C-terminal end: V $\alpha^D$ DBM V' (V and V' refering to additional optional sequences, $\alpha^D$ to the helix comprising the dodecapeptide motif, DBM to the DNA binding moiety). Number of mono-dodecapeptide meganucleases are known. See Table 1, Motif D (Also see Lucas et al., 2001, *Nucleic Acids Res.*, 29, 960-9, Table 1 and FIG. 1).

Therefore, the invention concerns a hybrid meganuclease comprising or consisting of a first domain and a second domain in the orientation N-terminal toward C-terminal, said first and second domains being derived from two different initial LAGLIDADG meganucleases, said initial meganucleases being either mono- or di-dodecapeptide meganucleases and said first and second domains being bound by a convenient linker and wherein said hybrid meganuclease is capable of causing DNA cleavage. The invention also contemplates a hybrid meganuclease comprising or consisting of two domains, each domain being derived from the same meganuclease, said two domains having a different arrangement than the initial meganuclease (i.e. the second domain is derived from the N-terminal domain of the initial meganuclease and/or the first domain is derived from the C-terminal of the initial meganuclease) and said first and second domains being bound by a convenient linker.

The initial mono- and di-dodecapeptide meganucleases according to the present invention for the generation of hybrid meganucleases are preferably selected from the group consisting of the meganucleases listed in the Table 1, notably I-Sce I, I-Chu I, I-Dmo I, I-Cre I, I-Csm I, PI-Sce I, PI-Tli I, PI-Mtu I, I-Ceu I, I-Sce II, I-Sce III, HO, PI-Civ I, PI-Ctr I, PI-Aae I, PI-Bsu I, PI-Dha I, PI-Dra I, PI-Mav I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, and PI-Tsp I; preferably, I-Sce I, I-Chu I, I-Dmo I, I-Cre I, I-Csm I, PI-Pfu I, PI-Sce I, PI-Tli I, PI-Mtu I, I-Ceu I, I-Sce II, I-Sce III, and HO; more preferably, I-Sce I, I-Chu I, I-Dmo I, I-Cre I, I-Csm I, PI-Sce I, PI-Pfu I, PI-Tli I, PI-Mtu I, and I-Ceu I; still more preferably I-Dmo I, I-Cre I, I-Sce I, and I-Chu I; or, even more preferably I-Dmo I, and I-Cre I.

The initial di-dodecapeptide meganucleases according to the present invention for the generation of hybrid meganuclease are preferably selected from the group consisting of the meganucleases comprising a "DD" or "dd" motif listed in the Table 1, notably: I-Sce I, I-Chu I, I-Dmo I, I-Csm I, PI-Sce I, PI-Tli I, PI-Mtu I, I-Sce II, I-Sce III, HO, PI-Civ I, PI-Ctr I, PI-Aae I, PI-Bsu I, PI-Dha I, PI-Dra I, PI-Mav I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, and PI-Tsp I; preferably, I-Sce I, I-Chu I, I-Dmo I, I-Csm I, PI-Pfu I, PI-Sce I, PI-Tli I, PI-Mtu I, I-Sce II, I-Sce III, and HO; more preferably, I-Sce I, I-Chu I, I-Dmo I, I-Csm I, PI-Sce I, PI-Tli I, and PI-Mtu I; still more preferably I-Dmo I, I-Sce I, and I-Chu I; or even more preferably I-Dmo I.

The initial mono-dodecapeptide meganucleases according to the present invention for the generation of hybrid meganucleases are preferably selected from the group consisting of the meganucleases comprising a "D" motif listed in the Table 1, notably: I-Cre I, I-Ceu I; preferably, I-Cre I.

More particularly, the present invention concerns the hybrid meganuclease comprising or consisting of a first domain from a mono- or di-dodecapeptide meganuclease and a second domain from another mono- or di-dodecapeptide meganuclease, said first and second domains being bound by a convenient linker. In a preferred embodiment, the invention concerns a hybrid meganuclease selected from the group consisting of the following hybrid meganucleases:

I-Sce I/I-Chu I, I-Sce I/PI-Pfu I, I-Chu I/I-Sce I, I-Chu I/PI-Pfu I, I-Sce I/I-Dmo I, I-Dmo I/I-Sce I, I-Dmo I/PI-Pfu I, I-Dmo I/I-Cre I, I-Cre I/I-Dmo I, I-Cre I/PI-Pfu I, I-Sce I/I-Csm I, I-Sce I/I-Cre I, I-Sce I/PI-Sce I, I-Sce I/PI-Tli I, I-Sce I/PI-Mtu I, I-Sce I/I-Ceu I, I-Cre I/I-Ceu I, I-Chu I/I-Cre I, I-Chu I/I-Dmo I, I-Chu I/I-Csm I, I-Chu I/PI-Sce I, I-Chu I/PI-Tli I, I-Chu I/PI-Mtu I, I-Cre I/I-Chu I, I-Cre I/I-Csm I, I-Cre I/PI-Sce I, I-Cre I/PI-Tli I, I-Cre I/PI-Mtu I, I-Cre I/I-SceI, I-Dmo I/I-Chu I, I-Dmo I/I-Csm I, I-Dmo I/PI-Sce I, I-Dmo I/PI-Tli I, I-Dmo I/PI-Mtu I, I-Csm I/I-Chu I, I-Csm I/PI-Pfu I, I-Csm I/I-Cre I, I-Csm I/I-Dmo I, I-Csm I/PI-Sce I, I-Csm I/PI-Tli I, I-Csm I/PI-Mtu I, I-Csm I/I-Sce I, PI-Sce I/I-Chu I, PI-Sce I/I-Pfu I, PI-Sce I/I-Cre I, PI-Sce I/I-Dmo I, PI-Sce I/I-Csm I, PI-Sce I/PI-Tli I, PI-Sce I/PI-Mtu I, PI-Sce I/I-Sce I, PI-Tli I/I-Chu I, PI-Tli I/PI-Pfu I, PI-Tli I/I-Cre I, PI-Tli I/I-Dmo I, PI-Tli I/I-Csm I, PI-Tli I/PI-Sce I, PI-Tli I PI-Mtu I, PI-Tli I/I-Sce I, PI-Mtu I/I-Chu I, PI-Mtu I/PI-Pfu I, PI-Mtu I/I-Cre I, PI-Mtu I/I-Dmo I, PI-Mtu I/I-Csm I, PI-Mtu I/PI-Sce I, PI-Mtu I/PI-Tli I, and PI-Mtu I/I-SceI;

Preferably, I-Sce I/I-Chu I, I-Sce I/PI-Pfu I, I-Chu I/I-Sce I, I-Chu I/PI-Pfu I, I-Sce I/I-Dmo I, I-Dmo I/I-Sce I, I-Dmo I/PI-Pfu I, I-Dmo I/I-Cre I, I-Cre I/I-Dmo I, I-Cre I/PI-Pfu I, I-Sce I/I-Csm I, I-Sce I/I-Cre I, I-Sce I/PI-Sce I, I-Sce I/PI-Tli I, I-Sce I/PI-Mtu I, I-Sce I/I-Ceu I, I-Chu I/I-Cre I, I-Chu I/I-Dmo I, I-Chu I/I-Csm I, I-Chu I/PI-Sce I, I-Chu I/PI-Tli I, I-Chu I/PI-Mtu I, I-Cre I/I-Chu I, I-Cre I/I-Csm I, I-Cre I/PI-Sce I, I-Cre I/PI-Tli I, I-Cre I/PI-Mtu I, I-Cre I/I-SceI, I-Dmo I/I-Chu I, I-Dmo I/I-Csm I, I-Dmo I/PI-Sce I, I-Dmo I/PI-Tli I, I-Dmo I/PI-Mtu I, I-Csm I/I-Chu I, I-Csm I/PI-Pfu I, I-Csm I/I-Cre I, I-Csm I/I-Dmo I, I-Csm I/PI-Sce I, I-Csm I/PI-Tli I, I-Csm I/PI-Mtu I, I-Csm I/I-Sce I, PI-Sce I/I-Chu I, PI-Sce I/I-Pfu I, PI-Sce I/I-Cre I, PI-Sce I/I-Dmo I, PI-Sce I/I-Csm I, PI-Sce I/PI-Tli I, PI-Sce I/PI-Mtu I, PI-Sce I/I-Sce I, PI-Tli I/I-Chu I, PI-Tli I/PI-Pfu I, PI-Tli I/I-Cre I, PI-Tli I/I-Dmo I, PI-Tli I/I-Csm I, PI-Tli I/PI-Sce I, PI-Tli I/PI-Mtu I, PI-Tli I/I-Sce I, PI-Mtu I/I-Chu I, PI-Mtu I/PI-Pfu I, PI-Mtu I/I-Cre I, PI-Mtu I/I-Dmo I, PI-Mtu I/I-Csm I, PI-Mtu I/PI-Sce I, PI-Mtu I/PI-Tli I, and PI-Mtu I/I-SceI;

More preferably I-Sce I/I-Chu I, I-Chu I/I-Sce I, I-Sce I/I-Dmo I, I-Dmo I/I-Sce I, I-Dmo I/I-Cre I, and I-Cre I/I-Dmo I;

Still more preferably I-Dmo I/I-Cre I, and I-Cre I/I-Dmo I; or,

Even more preferably I-Dmo I/I-Cre I; more particularly the hybrid meganuclease of SEQ ID No 2 or 4.

For example, for "I-Sce I/I-Ceu I", the first indicated meganuclease corresponds to the origin of the first domain of the hybrid meganuclease and the second indicated meganuclease to the origin of the second domain of the hybrid meganuclease.

Optionally, said hybrid meganuclease comprises or consists of:

1) a first domain from a di-dodecapeptide meganuclease and a second domain from another di-dodecapeptide meganuclease, said first and second domains being bound by a convenient linker;

2) a first domain from a mono-dodecapeptide meganuclease and a second domain from another di-dodecapeptide meganuclease, said first and second domains being bound by a convenient linker;

3) a first domain from a di-dodecapeptide meganuclease and a second domain from another mono-dodecapeptide meganuclease, said first and second domains being bound by a convenient linker; or 4) a first domain from a mono-dodecapeptide meganuclease and a second domain from the same or another mono-dodecapeptide meganuclease, preferably from another mono-dodecapeptide meganuclease, said first and second domains being bound by a convenient linker.

Preferably, said hybrid meganuclease comprises or consists of:

1) a first domain from a di-dodecapeptide meganuclease and a second domain from another di-dodecapeptide meganuclease, said first and second domains being bound by a convenient linker; or, 2) a first domain from a di-dodecapeptide meganuclease and a second domain from another mono-dodecapeptide meganuclease, said first and second domains being bound by a convenient linker.

More preferably, said hybrid meganucleases comprise or consists of a first domain from a di-dodecapeptide meganuclease and a second domain from another di-dodecapeptide meganuclease, said first and second domains being bound by a convenient linker.

Optionally, said hybrid meganuclease comprises or consists of:

1) a first domain derived from the N-terminal domain of a di-dodecapeptide meganuclease and a second domain derived from the C-terminal domain of another di-dodecapeptide meganuclease, said first and second domains being bound by a convenient linker;

2) a first domain derived from the N-terminal domain of a di-dodecapeptide meganuclease and a second domain derived from the N-terminal domain of the same or another di-dodecapeptide meganuclease, said first and second domains being bound by a convenient linker;

3) a first domain derived from the N-terminal domain of a di-dodecapeptide meganuclease and a second domain derived from another mono-dodecapeptide meganuclease, said first and second domains being bound by a convenient linker;

4) a first domain derived from the C-terminal domain of a di-dodecapeptide meganuclease and a second domain derived from the C-terminal domain of the same or another di-dodecapeptide meganuclease, said first and second domains being bound by a convenient linker;

5) a first domain derived from a mono-dodecapeptide meganuclease and a second domain derived from the C-terminal domain of another di-dodecapeptide meganuclease, said first and second domains being bound by a convenient linker;

6) a first domain derived from the C-terminal domain of a di-dodecapeptide meganuclease and a second domain derived from the N-terminal domain of the same or another di-dodecapeptide meganuclease, said first and second domains being bound by a convenient linker;

7) a first domain derived from a mono-dodecapeptide meganuclease and a second domain derived from the N-terminal domain of another di-dodecapeptide meganuclease, said first and second domains being bound by a convenient linker;

8) a first domain derived from the C-terminal domain of a di-dodecapeptide meganuclease and a second domain derived from another mono-dodecapeptide meganuclease, said first and second domains being bound by a convenient linker; or, 9) a first domain derived from a mono-dodecapeptide meganuclease and a second domain derived from the same or another mono-dodecapeptide meganuclease, said first and second domains being bound by a convenient linker.

Preferably, said hybrid meganuclease comprises or consists of:

1) a first domain derived from the N-terminal domain of a di-dodecapeptide meganuclease and a second domain derived from the C-terminal domain of another di-dodecapeptide meganuclease, said first and second domains being bound by a convenient linker;

2) a first domain derived from the N-terminal domain of a di-dodecapeptide meganuclease and a second domain derived from the N-terminal domain of the same or another di-dodecapeptide meganuclease, said first and second domains being bound by a convenient linker;

3) a first domain derived from the N-terminal domain of a di-dodecapeptide meganuclease and a second domain derived from another mono-dodecapeptide meganuclease;

4) a first domain derived from the C-terminal domain of a di-dodecapeptide meganuclease and a second domain derived from the C-terminal domain of the same or another di-dodecapeptide meganuclease, said first and second domains being bound by a convenient linker; or, 5) a first domain derived from a mono-dodecapeptide meganuclease and a second domain derived from the C-terminal domain of another di-dodecapeptide meganuclease, said first and second domains being bound by a convenient linker.

More preferably, said hybrid meganuclease comprises or consists of:

1) a first domain derived from the N-terminal domain of a di-dodecapeptide meganuclease and a second domain derived from the C-terminal domain of another di-dodecapeptide meganuclease, said first and second domains being bound by a convenient linker;

2) a first domain derived from the N-terminal domain of a di-dodecapeptide meganuclease and a second domain derived from the N-terminal domain of the same or another di-dodecapeptide meganuclease, said first and second domains being bound by a convenient linker; or, 3) a first domain derived from the N-terminal domain of a di-dodecapeptide meganuclease and a second domain derived from another mono-dodecapeptide meganuclease, said first and second domains being bound by a convenient linker.

Are also contemplated in the present invention the hybrid meganucleases comprising or consisting of a first domain and a second domain from the same di-dodecapeptide meganuclease, said first and second domains being bound by a convenient linker, if the ordering of the domain is not the same of the initial meganuclease. More particularly, are contemplated in the present invention the hybrid meganuclease comprising a first and a second domains in the orientation N-terminal toward C-terminal, wherein each domain are derived from the same di-dodecapeptide meganuclease and said first domain is derived from the C-terminal domain and said second domain is derived from the N-terminal domain.

The means for introducing a link between the two domains of the hybrid meganuclease is well known by one man skilled in the art. In the present invention, the preferred means are either the use of a flexible polypeptide linker or the use of a loop from a di-dodecapeptide meganuclease. In the present invention, the loop is an embodiment of the linker. The flexible polypeptide linker essentially comprises glycine, serine and threonine residues. The loop can be either a loop present in one of the 2 initial di-dodecapeptide meganucleases used for design the hybrid meganuclease or a loop from any other di-dodecapeptide meganuclease, preferably the I-Dmo I loop, which is introduced between the two domains.

Our preferred approach for generating hybrid meganuclease is a domain swapping consistent with the various LAGLIDADG meganucleases.

N-terminal Domain of di-dodecapeptide Meganuclease/C-terminal Domain of di-dodecapeptide Meganuclease A first preferred embodiment concerns a hybrid meganuclease comprising or consisting of a first domain derived from the N-terminal domain of a di-dodecapeptide meganuclease (A) and a second domain derived from the C-terminal domain of another di-dodecapeptide meganuclease (B), said first and second domains being bound by a convenient linker. The swapping point is positioned at any convenient place. The swapping point is the point at which the sequence of the first meganuclease (A) is substantially replaced by the sequence of the second meganuclease (B). This swapping point can be positioned from the last helix of the DNA binding moiety DBM to the end of the helix comprising the second dodecapeptide motif, $\alpha'^D$. It is preferably positioned within the loop (L) preceding the second dodecapeptide motif ($\alpha'^D$) or in the helix ($\alpha'^D$) comprising the dodecapeptide motif. Generally, few amino acids, about 4 to 10 amino acids, upstream the dodecapeptide motif, also participate to the formation of the helix ($\alpha'^D$). In one preferred embodiment, the swapping point is positioned within the helix ($\alpha'^D$). In a particularly preferred embodiment, the swapping point is positioned in the helix ($\alpha'^D$) before the dodecapeptide motif itself. The resulting hybrid meganuclease comprises the N-terminal domain of the meganuclease A and the C-terminal domain of the meganuclease B. Such hybrid meganuclease schematically comprises:

| Type | V optional | $\alpha^D$ | DBM | L | $\alpha'^D$ | DBM' | V' optional |
|---|---|---|---|---|---|---|---|
| 1 | A | αA | A(N) | A | α'A | B(C) | B |
| 2 | A | αA | A(N) | A | α'A/α'B | B(C) | B |
| 3 | A | αA | A(N) | A | α'B | B(C) | B |
| 4 | A | αA | A(N) | A/B | α'B | B(C) | B |
| 5 | A | αA | A(N) | B | α'B | B(C) | B |
| 6 | A | αA | A(N)/B(N) | B | α'B | B(C) | B |

A and B indicating the meganuclease at the origin of the segment V, $\alpha^D$, DBM, L, $\alpha'^D$, DBM', V'. A/B indicates that the swapping point is into the segment, the origin of the first part of the element is A and that of the second part is B. αA and αB refer to the $\alpha^D$ of the N-terminal domain and α'A and α'B refer to the $\alpha'^D$ of the C-terminal domain. For "DBM" column, the letter (N) and (C), respectively, indicate the origin from the N-terminal domain and the C-terminal domain.

In an alternative embodiment, the swapping point is replaced by a "swapping domain". Indeed, instead of abruptly changing the sequence, the helices $\alpha^D$ and $\alpha'^D$ of the hybrid meganuclease can be a mixture of the two initial meganucleases. The amino acid residues from the helices $\alpha^D$ and $\alpha'^D$ which are directed towards the helices interface are those of one meganuclease for both helices $\alpha^D$ and $\alpha'^D$ (either those of $\alpha^D$ and $\alpha'^D$ from the meganuclease A or those of $\alpha^D$ and $\alpha'^D$ from the meganuclease B). Optionally, the residues at the interface could be derived from another pair of dodecapeptide helices from a mono- or di-dodecapeptide meganuclease X. Within each domain, the amino acid residues from the helix comprising $\alpha^D$ and $\alpha'^D$ which are directed towards the inside of the domain are those corresponding to the residues found at that position in that domain of the meganuclease it comes from (those of $\alpha^D$ from the meganuclease A and those of $\alpha'^D$ from the meganuclease B). Such hybrid meganuclease schematically comprises:

| Type | V op- tional | $\alpha^D$ intra | $\alpha^D$ inter | DBM | L | $\alpha'^D$ inter | $\alpha'^D$ intra | DBM' | V' op- tional |
|---|---|---|---|---|---|---|---|---|---|
| 1 | A | αA | αA | A(N) | A | α'A | α'B | B(C) | B |
| 2 | A | αA | αB | A(N) | A | α'B | α'B | B(C) | B |
| 3 | A | αA | αX | A(N) | A | α'X | α'B | B(C) | B |
| 4 | A | αA | αX | A(N) | A | αX | α'B | B(C) | B |
| 5 | A | αA | αA | A(N) | A/B | α'B | α'B | B(C) | B |
| 6 | A | αA | αB | A(N) | A/B | α'B | α'B | B(C) | B |
| 7 | A | αA | αX | A(N) | A/B | α'X | α'B | B(C) | B |
| 8 | A | αA | αX | A(N) | A/B | αX | α'B | B(C) | B |
| 9 | A | αA | αA | A(N) | B | α'A | α'B | B(C) | B |
| 10 | A | αA | αB | A(N) | B | α'B | α'B | B(C) | B |
| 11 | A | αA | αX | A(N) | B | α'X | α'B | B(C) | B |
| 12 | A | αA | αX | A(N) | B | αX | α'B | B(C) | B |
| 13 | A | αA | αA | A(N)/B(N) | B | α'A | α'B | B(C) | B |
| 14 | A | αA | αB | A(N)/B(N) | B | α'B | α'B | B(C) | B |
| 15 | A | αA | αX | A(N)/B(N) | B | α'X | α'B | B(C) | B |
| 16 | A | αA | αX | A(N)/B(N) | B | αX | α'B | B(C) | B |

A, B, and X indicating the meganuclease at the origin of the segment V, $\alpha^D$, DBM, L, $\alpha'^D$, DBM', V'. A/B indicates that the swapping point is into the segment, the origin of the first part of the element is A and that of the second part is B. "inter" refers to the residues of $\alpha^D$ and $\alpha'^D$ towards the interface between the domains, and "intra" refers to the residues of $\alpha^D$ and $\alpha'^D$ towards the inside of each domain. αA and αB refer to the $\alpha^D$ of the N-terminal domain and α'A and α'B refer to the $\alpha'^D$ of the C-terminal domain. For "DBM" column, the letter (N) and (C), respectively, indicate the origin from the N-terminal domain and the C-terminal domain.

Optionally, some amino acid modifications can be further introduced in order to avoid the steric hindrance between amino acid side chains and/or to increase the stability. Optionally, some amino acid modifications can be further introduced in order to enhance the production and/or the solubility and to decrease the toxicity (Turmel et al, 1997, *Nucleic Acid Research*, 25, 2610-2619). Optionally, the loop can be completely or partially replaced by a convenient linker. A convenient linker is preferably flexible. Said flexible linker preferably comprises glycine, serine and threonine residues. Short flexible linker can also be introduced between the loop and the domains. Optionally, the loop can also be replaced by a loop from any other di-dodecapeptide meganuclease, preferably the I-Dmo I loop.

Optionally, such hybrid meganuclease comprising or consisting of a first domain from the N-terminal domain of a di-dodecapeptide meganuclease (A) and a second domain from the C-terminal domain of another di-dodecapeptide meganuclease (B), said first and second domains being bound by a convenient linker, can further comprise, at its N and/or C-terminal end, a loop or linker and any additional domain.

Preferably, said additional domain is a DNA binding domain, a transcription activator or repressor domain, a nuclear localization signal, or a DNA cleavage domain. Optionally, the endonuclease activity of such hybrid can be abolished. Thus, the main function of hybrid is a specific DNA binding.

N-terminal Domain of di-dodecapeptide Meganuclease/N-terminal Domain of di-dodecapeptide Meganuclease A second embodiment concerns a hybrid meganuclease comprising or consisting of a first domain derived from the N-terminal domain of a di-dodecapeptide meganuclease (A) and a second domain derived from the N-terminal domain of another di-dodecapeptide meganuclease (B), said first and second domains being bound by a convenient linker. The swapping point is positioned at any convenient place. It is preferably positioned at the end of the loop (LA) preceding the second dodecapeptide motif ($\alpha'^D$) or in the helix ($\alpha'^D$). In one preferred embodiment, the swapping point is positioned within the helix ($\alpha'^D$). In a particularly preferred embodiment, the swapping point is positioned in the helix ($\alpha'^D$) before the dodecapeptide motif itself. The resulting hybrid meganuclease comprises, from the N-terminal end to C-terminal end, the N-terminal domain of the meganuclease A and the N-terminal domain of the meganuclease B. Preferably, the resulting hybrid meganuclease does not comprise the DBM of the C-terminal domain of the meganuclease B, more preferably its C-terminal domain. Such hybrid meganuclease schematically comprises:

| Type | V optional | $\alpha^D$ | DBM | L | $\alpha'^D$ | DBM' | V' optional |
|---|---|---|---|---|---|---|---|
| 1 | A | αA | A(N) | A | α'A | B(N) | B |
| 2 | A | αA | A(N) | A | α'A/αB | B(N) | B |
| 3 | A | αA | A(N) | A | αB | B(N) | B |

A and B indicating the meganuclease at the origin of the segment V, $\alpha^D$, DBM, L, $\alpha'^D$, DBM', V'. A/B indicates that the swapping point is into the segment, the origin of the first part of the element is A and that of the second part is B. αA and αB refer to the $\alpha^D$ of the N-terminal domain and α'A and α'B refer to the $\alpha'^D$ of the C-terminal domain. For "DBM" column, the letter (N) and (C), respectively, indicate the origin from the N-terminal domain and the C-terminal domain.

In an alternative embodiment, the swapping point is replaced by a swapping domain. Indeed, instead of abruptly change the sequence, the helices $\alpha^D$ and $\alpha'^D$ of the hybrid meganuclease can be a mixture of the two initial meganucleases. The amino acid residues from the helices $\alpha^D$ and $\alpha'^D$ which are directed towards the helix interface are those of one meganuclease for both helices $\alpha^D$ and $\alpha'^D$ (those of $\alpha^D$ and $\alpha'^D$ from either the meganuclease A or B). Optionally, the residues at the interface could be derived from another pair of dodecapeptide helices from a mono- or di-dodecapeptide meganuclease X. Within each domain, the amino acid residues from the helices $\alpha^D$ and $\alpha'^D$ which are directed towards the inside of the domain are those corresponding to the residues found at that position in that domain of the meganuclease it comes from (those of $\alpha^D$ from the meganuclease A and those of $\alpha'^D$ from the meganuclease B). Such hybrid meganuclease schematically comprises:

| Type | V op- tional | $\alpha^D$ intra | $\alpha^D$ inter | DBM | L | $\alpha'^D$ inter | $\alpha'^D$ intra | DBM' | V' op- tional |
|------|------|------|------|------|---|------|------|------|------|
| 1 | A | αA | αA | A(N) | A | α'B | αB | B(N) | B |
| 2 | A | αA | αB | A(N) | A | α'B | αB | B(N) | B |
| 3 | A | αA | αX | A(N) | A | α'X | αB | B(N) | B |
| 4 | A | αA | αX | A(N) | A | αX | αB | B(N) | B |

A, B, and X indicating the meganuclease at the origin of the segment V, $\alpha^D$, DBM, L, $\alpha'^D$, DBM', V'. "inter" refers to the residues of $\alpha^D$ and $\alpha'^D$ towards the interface between the domains, and "intra" refers to the residues of $\alpha^D$ and $\alpha'^D$ towards the inside of each domain. αA and αB refer to the $\alpha^D$ of the N-terminal domain and α'A and α'B refer to the $\alpha'^D$ of the C-terminal domain. For "DBM" column, the letter (N) and (C), respectively, indicate the origin from the N-terminal domain and the C-terminal domain.

Optionally, some amino acid modifications can be further introduced in order to avoid the steric hindrance between amino acid side chains and/or to increase the stability. Optionally, some amino acid modifications can be further introduced in order to enhance the production and/or the solubility and to decrease the toxicity (Turmel et al, 1997, *Nucleic Acod Research*, 25, 2610-2619). Optionally, the loop can be completely or partially replaced by a convenient linker. A convenient linker is preferably flexible. Said flexible linker essentially comprises glycine, serine and threonine residues. Short flexible linker can also be introduced between the loop and the domains. Optionally, the loop can also be replaced by a loop from any other di-dodecapeptide meganuclease, preferably the I-Dmo I loop.

Optionally, such hybrid meganuclease comprising a first domain from the N-terminal domain of a di-dodecapeptide meganuclease (A) and a second domain from the N-terminal domain of another di-dodecapeptide meganuclease (B) can further comprise, at its N and/or C-terminal end, a loop or linker and any additional domain. Preferably, said additional domain is a DNA binding domain, a transcription activator or repressor domain, a nuclear localization signal, or a DNA cleavage domain. Optionally, the endonuclease activity of such hybrid can be abolished.

A hybrid meganuclease comprising or consisting of a first domain derived from the N-terminal domain of a di-dodecapeptide meganuclease (A) and a second domain derived from the N-terminal domain of the same di-dodecapeptide meganuclease (A), said first and second domains being bound by a convenient linker, is also contemplated in the present invention. The same rules of design are applied to this kind of meganuclease.

N-terminal Domain of di-dodecapeptide Meganuclease/ Domain of Mono-dodecapeptide Meganuclease A third embodiment concerns a hybrid meganuclease comprising or consisting of a first domain from the N-terminal domain of a di-dodecapeptide meganuclease (A) and a second domain from another mono-dodecapeptide meganuclease (B), said first and second domains being bound by a convenient linker. The swapping point is positioned at any convenient place. It is preferably positioned at the end of the loop (LA) preceding the second dodecapeptide motif ($\alpha'^D$) of the meganuclease (A) or in the helix $\alpha^D$. In one preferred embodiment, the swapping point is positioned within the helix $\alpha'^D$. In a particularly preferred embodiment, the swapping point is positioned in the helix $\alpha'^D$ before the dodecapeptide motif itself. The resulting hybrid meganuclease comprises, from the N-terminal end to C-terminal end, the N-terminal domain of the meganuclease A and the domain of the meganuclease B. Such hybrid meganuclease schematically comprises:

| Type | V optional | $\alpha^D$ | DBM | L | $\alpha'^D$ | DBM' | V' optional |
|------|------|------|------|---|------|------|------|
| 1 | A | αA | A(N) | A | α'B | B | B |
| 2 | A | αA | A(N) | A | α'B/αB | B | B |
| 3 | A | αA | A(N) | A | αB | B | B |

A and B indicating the meganuclease at the origin of the segment V, $\alpha^D$, DBM, L, $\alpha'^D$, DBM', V'. A/B indicates that the swapping point is into the segment, the origin of the first part of the element is A and that of the second part is B. αA and αB refer to the $\alpha^D$ of the N-terminal domain and α'A and α'B refer to the $\alpha'^D$ of the C-terminal domain. For "DBM" column, the letter (N) and (C), respectively, indicate the origin from the N-terminal domain and the C-terminal domain.

The invention concerns more particularly a hybrid meganuclease I-Dmo I/I-Cre I comprising or consisting of a first domain from the N-terminal domain of I-Dmo I meganuclease and a second domain from I-Cre I meganuclease, said first and second domains being bound by a convenient linker. Preferably, said convenient linker is the I-Dmo I meganuclease loop. Preferably, the swapping point is positioned in the helix $\alpha'^D$ before the dodecapeptide motif itself. In one embodiment, the invention concerns the hybrid meganucleases I-Dmo I/I-Cre I disclosed in example 1 and in FIG. 6 or a variant thereof.

In an alternative embodiment, the swapping point is replaced by a swapping domain. Indeed, instead of abruptly change the sequence, the helices $\alpha^D$ and $\alpha'^D$ of the hybrid meganuclease can be a mixture of the two initial meganucleases. The amino acid residues from the helices $\alpha^D$ and $\alpha'^D$ which are directed towards the helix interface are those of one meganuclease for both helices (those of $\alpha^D$ and $\alpha'^D$ from the meganuclease A, or those of $\alpha^D$ from the meganuclease B). Optionally, the residues at the interface could be derived from another pair of dodecapeptide helices from a mono- or di-dodecapeptide meganuclease X. Within each domain, the amino acid residues from the helices $\alpha^D$ and $\alpha'^D$ which are directed towards the inside of the domain are those corresponding to the residues found at that position in that domain of the meganuclease it comes from (those of $\alpha^D$ from the meganuclease A and those of $\alpha^D$ from the meganuclease B). Such hybrid meganuclease schematically comprises:

| Type | V op- tional | $\alpha^D$ intra | $\alpha^D$ inter | DBM | L | $\alpha'^D$ inter | $\alpha'^D$ intra | DBM' | V' op- tional |
|------|------|------|------|------|---|------|------|------|------|
| 1 | A | αA | αA | A(N) | A | α'A | αB | B | B |
| 2 | A | αA | αB | A(N) | A | αB | αB | B | B |
| 3 | A | αA | αX | A(N) | A | α'X | αB | B | B |
| 4 | A | αA | αX | A(N) | A | αX | αB | B | B |

A, B, and X indicating the meganuclease at the origin of the segment V, $\alpha^D$, DBM, L, $\alpha'^D$, DBM', V'. A/B indicates that the swapping point is into the segment, the origin of the first part of the element is A and that of the second part is B. "inter" refers to the residues of $\alpha^D$ and $\alpha'^D$ towards the interface between the domains, and "intra" refers to the residues of $\alpha^D$ and $\alpha'^D$ towards the inside of each domain. αA and αB refer to the $\alpha^D$ of the N-terminal domain and α'A and α'B refer to the $\alpha'^D$ of the C-terminal domain. For "DBM" column, the letter (N) and (C), respectively, indicate the origin from the N-terminal domain and the C-terminal domain.

Optionally, some amino acid modifications can be further introduced in order to avoid the steric hindrance between amino acid side chains and/or to increase the stability. Optionally, some amino acid modifications can be further introduced in order to enhance the production and/or the solubility and to decrease the toxicity (Turmel et al, 1997, *Nucleic Acod Research*, 25, 2610-2619). Optionally, the loop can be completely or partially replaced by a convenient linker. A convenient linker is preferably flexible. Said flexible linker preferably comprises glycine, serine and threonine residues. Short flexible linker can also be introduced between the loop and the domains. Optionally, the loop can also be replaced by a loop from any other di-dodecapeptide meganuclease, preferably the I-Dmo I loop.

Optionally, such hybrid meganuclease comprising a first domain from the N-terminal domain of a di-dodecapeptide meganuclease (A) and a second domain from the domain of another mono-dodecapeptide meganuclease (B) can further comprise, at its N-terminal and/or C-terminal end, a loop or linker and any additional domain. Preferably, said additional domain is a DNA binding domain, a transcription activator or repressor domain, a nuclear localization signal or a DNA cleavage domain. Optionally, the endonuclease activity of such hybrid can be abolished.

C-terminal Domain of di-dodecapeptide Meganuclease/C-terminal Domain of di-dodecapeptide Meganuclease A forth preferred embodiment concerns a hybrid meganuclease comprising or consisting of a first domain derived from the C-terminal domain of a di-dodecapeptide meganuclease (A) and a second domain derived from the C-terminal domain of another di-dodecapeptide meganuclease (B), said first and second domains being bound by a convenient linker. The swapping point is positioned at any convenient place. This swapping point can be positioned from the last helix of the DNA binding moiety DBM to the beginning of the loop (LB) preceding the helix $\alpha'^D$. It is preferably positioned at the beginning of the loop (LB) preceding the helix $\alpha'^D$. The resulting hybrid meganuclease comprises the C-terminal domain of the meganucleases A and B. Preferably, the resulting hybrid meganuclease does not comprise the DBM of the N-terminal domain of the meganuclease A, more preferably its N-terminal domain. Such hybrid meganuclease schematically comprises:

| Type | V optional | $\alpha^D$ | DBM | L | $\alpha'^D$ | DBM' | optional |
|---|---|---|---|---|---|---|---|
| 1 | A | α'B | A(C) | B | α'B | B(C) | B |
| 2 | A | α'B | A(C)/B(N) | B | α'B | B(C) | B |

A and B indicating the meganuclease at the origin of the segment V, $\alpha^D$, DBM, L, $\alpha'^D$, DBM', V'. A/B indicates that the swapping point is into the segment, the origin of the first part of the element is A and that of the second part is B. αA and αB refer to the $\alpha^D$ of the N-terminal domain and α'A and α'B refer to the $\alpha'^D$ of the C-terminal domain. For "DBM" column, the letter (N) and (C), respectively, indicate the origin from the N-terminal domain and the C-terminal domain.

In an alternative embodiment, the swapping point is replaced by a "swapping domain". Indeed, instead of abruptly change the sequence, the helices $\alpha^D$ and $\alpha'^D$ of the hybrid meganuclease can be a mixture of the two initial meganucleases. The amino acid residues from the helices $\alpha^D$ and $\alpha'^D$ which are directed towards the helices interface are those of one meganuclease for both helices $\alpha^D$ and $\alpha'^D$ (those of $\alpha^D$ and $\alpha'^D$ from the meganuclease A or those of $\alpha^D$ and $\alpha'^D$ from the meganuclease B). Optionally, the residues at the interface could be derived from another pair of dodecapeptide helices from a mono- or di-dodecapeptide meganuclease X. Within each domain, the amino acid residues from the helices $\alpha^D$ and $\alpha'^D$ which are directed towards the inside of the domain are those corresponding to the residues found at that position in that domain of the meganuclease it comes from (those of $\alpha'^D$ from the meganuclease A and those of $\alpha'^D$ from the meganuclease B). Such hybrid meganuclease schematically comprises:

| Type | V optional | $\alpha^D$ intra | $\alpha^D$ inter | DBM' | L | $\alpha'^D$ inter | $\alpha'^D$ intra | DBM' | V' optional |
|---|---|---|---|---|---|---|---|---|---|
| 1 | A | α'A | αA | A(C) | B | α'A | α'B | B(C) | B |
| 2 | A | α'A | αB | A(C) | B | α'B | α'B | B(C) | B |
| 3 | A | α'A | αX | A(C) | B | α'X | α'B | B(C) | B |
| 4 | A | α'A | αX | A(C) | B | αX | α'B | B(C) | B |
| 5 | A | α'A | αA | A(C)/B(N) | B | α'A | α'B | B(C) | B |
| 6 | A | α'A | αB | A(C)/B(N) | B | α'B | α'B | B(C) | B |
| 7 | A | α'A | αX | A(C)/B(N) | B | α'X | α'B | B(C) | B |
| 8 | A | α'A | αX | A(C)/B(N) | B | αX | α'B | B(C) | B |

A, B, and X indicating the meganuclease at the origin of the segment V, $\alpha^D$, DBM, L, $\alpha'^D$, DBM', V'. A/B indicates that the swapping point is into the segment, the origin of the first part of the element is A and that of the second part is B. "inter" refers to the residues of $\alpha^D$ and $\alpha'^D$ towards the interface between the domains, and "intra" refers to the residues of $\alpha^D$ and $\alpha'^D$ towards the inside of each domain. αA and αB refer to the $\alpha^D$ of the N-terminal domain and α'A and α'B refer to the $\alpha'^D$ of the C-terminal domain. For "DBM" column, the letter (N) and (C), respectively, indicate the origin from the N-terminal domain and the C-terminal domain.

Optionally, some amino acid modifications can be further introduced in order to avoid the steric hindrance between amino acid side chains and/or to increase the stability. Optionally, some amino acid modifications can be further introduced in order to enhance the production and/or the solubility and to decrease the toxicity (Turmel et al, 1997, *Nucleic Acod Research*, 25, 2610-2619). Optionally, the loop can be completely or partially replaced by a convenient linker. A convenient linker is preferably flexible. Said flexible linker preferably comprises glycine, serine and threonine residues. Short flexible linker can also be introduced between the loop and the domains. Optionally, the loop can also be replaced by a loop from any other di-dodecapeptide meganuclease, preferably the I-Dmo I loop.

Optionally, such hybrid meganuclease comprising a first domain from the C-terminal domain of a di-dodecapeptide meganuclease (A) and a second domain from the C-terminal domain of another di-dodecapeptide meganuclease (B) can further comprise, at its N-terminal and/or C-terminal end, a loop or linker and any additional domain. Preferably, said additional domain is a DNA binding domain, a transcription activator or repressor domain, a nuclear localization signal or a DNA cleavage domain. Optionally, the endonuclease activity of such hybrid can be abolished.

A hybrid meganuclease comprising or consisting of a first domain derived from the C-terminal domain of a di-dodecapeptide meganuclease (A) and a second domain derived from the C-terminal domain of the same di-dodecapeptide meganuclease (A), said first and second domains being bound by a convenient linker, is also contemplated in the present invention. The same rules of design are applied to this kind of meganuclease.

Domain of Mono-dodecapeptide Meganuclease/C-terminal Domain of di-dodecapeptide Meganuclease A fifth embodiment concerns a hybrid meganuclease comprising or consisting of a first domain from the domain of a mono-dodecapeptide meganuclease (A) and a second domain from the C-terminal domain of another di-dodecapeptide meganuclease (B), said first and second domains being bound by a convenient linker. The swapping point can be positioned from the last helix of the DNA binding moiety DBM to the beginning of the loop (LB) preceding the helix $\alpha^{\prime D}$. It is preferably positioned at the beginning of the loop (LB) preceding the helix ($\alpha^{\prime D}$) The resulting hybrid meganuclease comprises, from the N-terminal end to C-terminal end, the domain of the meganuclease A and the C-terminal domain of the meganuclease B. Such hybrid meganuclease schematically comprises:

| Type | V optional | $\alpha^D$ | DBM | L | $\alpha^{\prime D}$ | DBM' | V' optional |
|---|---|---|---|---|---|---|---|
| 1 | A | αA | A | B | α'B | B(C) | B |
| 2 | A | αA | A/B(N) | B | α'B | B(C) | B |

A and B indicating the meganuclease at the origin of the segment V, $\alpha^D$, DBM, L, $\alpha^{\prime D}$, DBM', V'. A/B indicates that the swapping point is into the segment, the origin of the first part of the element is A and that of the second part is B. αA and αB refer to the $\alpha^D$ of the N-terminal domain and α'A and α'B refer to the $\alpha^{\prime D}$ of the C-terminal domain. For "DBM" column, the letter (N) and (C), respectively, indicate the origin from the N-terminal domain and the C-terminal domain.

In an alternative embodiment, the swapping point is replaced by a "swapping domain". Indeed, instead of abruptly change the sequence, the helices $\alpha^D$ and $\alpha^{\prime D}$ of the hybrid meganuclease can be a mixture of the two initial meganucleases. The amino acid residues from the helices $\alpha^D$ and $\alpha^{\prime D}$ which are directed towards the helices interface are those of one meganuclease for both helices $\alpha^D$ and $\alpha^{\prime D}$ (those of $\alpha^D$ from the meganuclease A or those of $\alpha^D$ and $\alpha^{\prime D}$ from the meganuclease B). Optionally, the residues at the interface could be derived from another pair of dodecapeptide helices from a mono- or di-dodecapeptide meganuclease X. Within each domain, the amino acid residues from the helices $\alpha^D$ and $\alpha^{\prime D}$ which are directed towards the inside of the domain are those corresponding to the residues found at that position in that domain of the meganuclease it comes from (those of $\alpha^D$ from the meganuclease A and those of $\alpha^{\prime D}$ from the meganuclease B). Such hybrid meganuclease schematically comprises:

| Type | V op-tional | $\alpha^D$ intra | $\alpha^D$ inter | DBM | L | $\alpha^{\prime D}$ inter | $\alpha^{\prime D}$ intra | DBM' | V' op-tional |
|---|---|---|---|---|---|---|---|---|---|
| 1 | A | αA | αA | A | B | αA | α'B | B(C) | B |
| 2 | A | αA | αB | A | B | α'B | α'B | B(C) | B |
| 3 | A | αA | αX | A | B | αX | α'B | B(C) | B |
| 4 | A | αA | αX | A | B | αX | α'B | B(C) | B |
| 5 | A | αA | αA | A/B(N) | B | αA | α'B | B(C) | B |
| 6 | A | αA | αB | A/B(N) | B | α'B | α'B | B(C) | B |
| 7 | A | αA | αX | A/B(N) | B | α'X | α'B | B(C) | B |
| 8 | A | αA | αX | A/B(N) | B | αX | α'B | B(C) | B |

A, B, and X indicating the meganuclease at the origin of the segment V, $\alpha^D$, DBM, L, $\alpha^{\prime D}$, DBM', V'. A/B indicates that the swapping point is into the segment, the origin of the first part of the element is A and that of the second part is B. "inter" refers to the residues of $\alpha^D$ and $\alpha^{\prime D}$ towards the interface between the domains, and "intra" refers to the residues of $\alpha^D$ and $\alpha^{\prime D}$ towards the inside of each domain. αA and αB refer to the $\alpha^D$ of the N-terminal domain and α'A and α'B refer to the $\alpha^{\prime D}$ of the C-terminal domain. For "DBM" column, the letter (N) and (C), respectively, indicate the origin from the N-terminal domain and the C-terminal domain.

Optionally, some amino acid modifications can be further introduced in order to avoid the steric hindrance between amino acid side chains and/or to increase the stability. Optionally, some amino acid modifications can be further introduced in order to enhance the production and/or the solubility and to decrease the toxicity (Turmel et al, 1997, *Nucleic Acod Research,* 25, 2610-2619). Optionally, the loop can be completely or partially replaced by a convenient linker. A convenient linker is preferably flexible. Said flexible linker essentially comprises glycine, serine and threonine residues. Short flexible linker can also be introduced between the loop and the domains. Optionally, the loop can also be replaced by a loop from any other di-dodecapeptide meganuclease, preferably the I-Dmo I loop.

Optionally, such hybrid meganuclease comprising a first domain from the domain of a mono-dodecapeptide meganuclease (A) and a second domain from the C-terminal domain of another di-dodecapeptide meganuclease (B) can further comprise, at its N-terminal and/or C-terminal end, a loop or linker and any additional domain. Preferably, said additional domain is a DNA binding domain, a transcription activator or repressor domain, a nuclear localization signal or a DNA cleavage domain. Optionally, the endonuclease activity of such hybrid can be abolished.

C-terminal Domain of di-dodecapeptide Meganuclease/N-terminal Domain of di-dodecapeptide Meganuclease A sixth embodiment concerns a hybrid meganuclease comprising or consisting of a first domain derived from the C-terminal domain of a di-dodecapeptide meganuclease (A) and a second domain derived from the N-terminal domain of another di-dodecapeptide meganuclease (B), said first and second domains being bound by a convenient linker. The first and the second domains are linked by either a convenient linker or a connecting loop from any di-dodecapeptide meganuclease Y, for example the loop of I-Dmo I meganuclease. A convenient linker is preferably flexible. Said flexible linker essentially comprises glycine, serine and threonine residues. Short flexible linkers can also be introduced between the loop and the domains. The linker is preferably attached at one end to the helix following the 4-stranded β-sheet of the DBM of the C-terminal domain of the meganuclease A and at the other end at the helix $\alpha^D$ of the N-terminal domain of the meganuclease B. The resulting hybrid meganuclease comprises, from the N-terminal end to C-terminal end, the C-terminal domain of the meganuclease A, a linker or a connecting loop and the N-terminal domain of the meganuclease B. Preferably, the resulting hybrid meganuclease does not comprise the DBM of the N-terminal domain of the meganuclease A, more preferably its N-terminal domain. Preferably, the resulting hybrid meganuclease does not comprise the DBM of the C-terminal domain of the meganuclease B, more preferably its C-terminal domain. Such hybrid meganuclease schematically comprises:

| V, optional | $\alpha^D$ | DBM | L | $\alpha^{\prime D}$ | DBM' | V', optional |
|---|---|---|---|---|---|---|
| A | α'A | A(C) | Y | αB | B(N) | B |

A, B and Y indicating the meganuclease at the origin of the segment V, $\alpha^D$, DBM, L, $\alpha^{\prime D}$, DBM', V'. αA and αB refer to the $\alpha^D$ of the N-terminal domain and α'A and α'B refer to the $\alpha^{\prime D}$ of the C-terminal domain. For "DBM" column, the letter (N) and (C), respectively, indicate the origin from the N-terminal domain and the C-terminal domain.

In an alternative embodiment, the helices $\alpha^D$ and $\alpha^{\prime D}$ of the hybrid meganuclease can be a mixture of the two initial meganucleases. The amino acid residues from the helices $\alpha^D$ and $\alpha^{\prime D}$ which are directed towards the helix interface are those of one meganuclease for both helices $\alpha^D$ and $\alpha^{\prime D}$ (those of $\alpha^D$ and $\alpha^{\prime D}$ from the meganuclease A or B). ). Optionally, the residues at the interface could be derived from another pair of dodecapeptide helices from a mono- or di-dodecapeptide meganuclease X. Within each domain, the amino acid residues from the helices $\alpha^D$ and $\alpha^{\prime D}$ which are directed towards the inside of the domain are those corresponding to the residues found at that position in that domain of the meganuclease it comes from (those of $\alpha^{\prime D}$ from the meganuclease A and those of $\alpha^D$ from the meganuclease B). Such hybrid meganuclease schematically comprises:

| Type | V, op- tional | $\alpha^D$ intra | $\alpha^D$ inter | DBM | L | $\alpha^{\prime D}$ inter | $\alpha^{\prime D}$ intra | DBM' | V', optional |
|---|---|---|---|---|---|---|---|---|---|
| 1 | A | α'A | αA | A(C) | Y | α'A | αB | B(N) | B |
| 2 | A | α'A | αB | A(C) | Y | α'B | αB | B(N) | B |
| 3 | A | α'A | αX | A(C) | Y | α'X | αB | B(N) | B |
| 4 | A | α'A | αX | A(C) | Y | αX | αB | B(N) | B |

A, B, X and Y indicating the meganuclease at the origin of the segment V, $\alpha^D$, DBM, L, $\alpha^{\prime D}$, DBM', V'. "inter" refers to the residues of $\alpha^D$ and $\alpha^{\prime D}$ towards the interface between the domains, and "intra" refers to the residues of $\alpha^D$ and $\alpha^{\prime D}$ towards the inside of each domain. αA and αB refer to the $\alpha^D$ of the N-terminal domain and α'A and α'B refer to the $\alpha^{\prime D}$ of the C-terminal domain. For "DBM" column, the letter (N) and (C), respectively, indicate the origin from the N-terminal domain and the C-terminal domain.

Optionally, some amino acid modifications can be further introduced in order to avoid the steric hindrance between amino acid side chains and/or to increase the stability. Optionally, some amino acid modifications can be further introduced in order to enhance the production and/or the solubility and to decrease the toxicity (Turmel et al, 1997, *Nucleic Acod Research*, 25, 2610-2619).

Optionally, such hybrid meganuclease comprising a first domain from the C-terminal domain of a di-dodecapeptide meganuclease (A) and a second domain from the N-terminal domain of another di-dodecapeptide meganuclease (B) can further comprise, at its N-terminal and/or C-terminal end, a loop or linker and any additional domain. Preferably, said additional domain is a DNA binding domain, a transcription activator or repressor domain, a nuclear localization signal or a DNA cleavage domain. Optionally, the endonuclease activity of such hybrid can be abolished.

A hybrid meganuclease comprising or consisting of a first domain derived from the C-terminal domain of a di-dodecapeptide meganuclease (A) and a second domain derived from the N-terminal domain of the same di-dodecapeptide meganuclease (A), said first and second domains being bound by a convenient linker, is also contemplated in the present invention. The same rules of design are applied to this kind of meganuclease.

Domain of Mono-dodecapeptide Meganuclease/N-terminal Domain of di-dodecapeptide Meganuclease A seventh embodiment concerns a hybrid meganuclease comprising or consisting of a first domain derived from the domain of a mono-dodecapeptide meganuclease (A) and a second domain derived from the N-terminal domain of another di-dodecapeptide meganuclease (B), said first and second domains being bound by a convenient linker. The first and the second domains are linked by either a convenient linker or a connecting loop from any di-dodecapeptide meganuclease Y, for example the loop of I-Dmo I meganuclease. A convenient linker is preferably flexible. Said flexible linker essentially comprises glycine, serine and threonine residues. Short flexible linker can also be introduced between the loop and the domains. The linker is preferably attached at one end to the helix following the 4-stranded β-sheet of the DBM of the domain of the meganuclease A and at the other end at the helix $\alpha^D$ of the N-terminal domain of the meganuclease B. The resulting hybrid meganuclease comprises, from the N-terminal end to C-terminal end, the domain of the meganuclease A, a linker or a connecting loop and the N-terminal domain of the meganuclease B. Preferably, the resulting hybrid meganuclease does not comprise the DBM of the C-terminal domain of the meganuclease B, more preferably its C-terminal domain.

Such hybrid meganuclease schematically comprises:

| V, optional | $\alpha^D$ | DBM | L | $\alpha^{\prime D}$ | DBM' | V', optional |
|---|---|---|---|---|---|---|
| A | αA | A | Y | αB | B(N) | B |

A, B and Y indicating the meganuclease at the origin of the segment V, $\alpha^D$, DBM, L, $\alpha^{\prime D}$, DBM', V'. αA and αB refer to the $\alpha^D$ of the N-terminal domain and α'A and α'B refer to the $\alpha^{\prime D}$ of the C-terminal domain. For "DBM" column, the letter (N) and (C), respectively, indicate the origin from the N-terminal domain and the C-terminal domain.

In an alternative embodiment, the helices $\alpha^D$ and $\alpha^{\prime D}$ of the hybrid meganuclease can be a mixture of the two initial meganucleases. The amino acid residues from the helices $\alpha^D$ and $\alpha^{\prime D}$ which are directed towards the helix interface are those of one meganuclease for both helices (those of $\alpha^D$ from the meganuclease A, or those of $\alpha^D$ and $\alpha^{\prime D}$ from the meganuclease B). Optionally, the residues at the interface could be derived from another pair of dodecapeptide helices from a mono- or di-dodecapeptide meganuclease X. Within each domain, the amino acid residues from the helices $\alpha^D$ and $\alpha^{\prime D}$ which are directed towards the inside of the domain are those corresponding to the residues found at that position in that domain of the meganuclease it comes from (those of $\alpha^D$ from the meganuclease A and those of $\alpha'^D$ from the meganuclease B). Such hybrid meganuclease schematically comprises:

| Type | V, optional | $\alpha^D$ intra | $\alpha^D$ inter | DBM | L | $\alpha'^D$ inter | $\alpha'^D$ intra | DBM' | V', optional |
|---|---|---|---|---|---|---|---|---|---|
| 1 | A | αA | αA | A | Y | αA | αB | B(N) | B |
| 2 | A | αA | αB | A | Y | αB | αB | B(N) | B |
| 3 | A | αA | αX | A | Y | α'X | αB | B(N) | B |
| 4 | A | αA | αX | A | Y | αX | αB | B(N) | B |

A, B, X and Y indicating the meganuclease at the origin of the segment V, $\alpha^D$, DBM, L, $\alpha'^D$, DBM', V'. "inter" refers to the residues of $\alpha^D$ and $\alpha'^D$ towards the interface between the domains, and "intra" refers to the residues of $\alpha^D$ and $\alpha'^D$ towards the inside of each domain. αA and αB refer to the $\alpha^D$ of the N-terminal domain and α'A and α'B refer to the $\alpha'^D$ of the C-terminal domain. For "DBM" column, the letter (N) and (C), respectively, indicate the origin from the N-terminal domain and the C-terminal domain.

Optionally, some amino acid modifications can be further introduced in order to avoid the steric hindrance between amino acid side chains and/or to increase the stability. Optionally, some amino acid modifications can be further introduced in order to enhance the production and/or the solubility and to decrease the toxicity (Turmel et al, 1997, *Nucleic Acod Research*, 25, 2610-2619).

Optionally, such hybrid meganuclease comprising a first domain from the domain of a mono-dodecapeptide meganuclease (A) and a second domain from the N-terminal domain of another di-dodecapeptide meganuclease (B) can further comprise, at its N-terminal and/or C-terminal end, a loop or linker and any additional domain. Preferably, said additional domain is a DNA binding domain, a transcription activator or repressor domain, a nuclear localization signal or a DNA cleavage domain. Optionally, the endonuclease activity of such hybrid can be abolished.

C-terminal Domain of di-dodecapeptide Meganuclease/Domain of Mono-dodecapeptide Meganuclease A eighth embodiment concerns a hybrid meganuclease comprising or consisting of a first domain derived from the C-terminal domain of a di-dodecapeptide meganuclease (A) and a second domain derived from the domain of another mono-dodecapeptide meganuclease (B), said first and second domains being bound by a convenient linker. The first and the second domains are linked by either a convenient linker or a connecting loop from any di-dodecapeptide meganuclease Y, for example the loop of I-Dmo I meganuclease. A convenient linker is preferably flexible. Said flexible linker essentially comprises glycine, serine and threonine residues. Short flexible linker can also be introduced between the loop and the domains. The linker is preferably attached at one end to the helix following the 4-stranded β-sheet of the DBM of the C-terminal domain of the meganuclease A and at the other end at the helix $\alpha^D$ of the domain of the meganuclease B. The resulting hybrid meganuclease comprises, from the N-terminal end to C-terminal end, the C-terminal domain of the meganuclease A, a linker or a connecting loop and the domain of the meganuclease B. Preferably, the resulting hybrid meganuclease does not comprise the DBM of the N-terminal domain of the meganuclease A, more preferably its N-terminal domain. Such hybrid meganuclease schematically comprises:

| V, optional | $\alpha^D$ | DBM | L | $\alpha'^D$ | DBM' | V', optional |
|---|---|---|---|---|---|---|
| A | α'A | A(C) | Y | αB | B | B |

A, B, and Y indicating the meganuclease at the origin of the segment V, $\alpha^D$, DBM, L, $\alpha'^D$, DBM', V'. αA and αB refer to the a D of the N-terminal domain and α'A and α'B refer to the $\alpha'^D$ of the C-terminal domain. For "DBM" column, the letter (N) and (C), respectively, indicate the origin from the N-terminal domain and the C-terminal domain.

In an alternative embodiment, the helices $\alpha^D$ and $\alpha'^D$ of the hybrid meganuclease can be a mixture of the two initial meganucleases. The amino acid residues from the helices $\alpha^D$ and $\alpha'^D$ which are directed towards the helix interface are those of one meganuclease for both helices (those of $\alpha^D$ and $\alpha'^D$ from the meganuclease A, or those of $\alpha^D$ from the meganuclease B). Optionally, the residues at the interface could be derived from another pair of dodecapeptide helices from a mono- or di-dodecapeptide meganuclease X. Within each domain, the amino acid residues from the helices $\alpha^D$ and $\alpha'^D$ which are directed towards the inside of the domain are those corresponding to the residues found at that position in that domain of the meganuclease it comes from (those of $\alpha'^D$ from the meganuclease A and those of $\alpha^D$ from the meganuclease B). Such hybrid meganuclease schematically comprises:

| Type | V, optional | $\alpha^D$ intra | $\alpha^D$ inter | DBM | L | $\alpha'^D$ inter | $\alpha'^D$ intra | DBM' | V', optional |
|---|---|---|---|---|---|---|---|---|---|
| 1 | A | α'A | αA | A(C) | Y | α'A | αB | B | B |
| 2 | A | α'A | αB | A(C) | Y | αB | αB | B | B |
| 3 | A | α'A | αX | A(C) | Y | αX | αB | B | B |
| 4 | A | α'A | αX | A(C) | Y | α'X | αB | B | B |

A, B, X and Y indicating the meganuclease at the origin of the segment V, $\alpha^D$, DBM, L, $\alpha'^D$, DBM', V'. "inter" refers to the residues of $\alpha^D$ and $\alpha'^D$ towards the interface between the domains, and "intra" refers to the residues of $\alpha^D$ and $\alpha'^D$ towards the inside of each domain. αA and αB refer to the $\alpha^D$ of the N-terminal domain and α'A and α'B refer to the $\alpha'^D$ of the C-terminal domain. For "DBM" column, the letter (N) and (C), respectively, indicate the origin from the N-terminal domain and the C-terminal domain.

Optionally, some amino acid modifications can be further introduced in order to avoid the steric hindrance between amino acid side chains and/or to increase the stability. Optionally, some amino acid modifications can be further introduced in order to enhance the production and/or the solubility and to decrease the toxicity (Turmel et al, 1997, *Nucleic Acod Research*, 25, 2610-2619).

Optionally, such hybrid meganuclease comprising a first domain from the C-terminal domain of a di-dodecapeptide meganuclease (A) and a second domain from the domain of another mono-dodecapeptide meganuclease (B) can further comprise, at its N-terminal and/or C-terminal end, a loop or linker and any additional domain. Preferably, said additional domain is a DNA binding domain, a transcription activator or repressor domain, a nuclear localization signal or a DNA cleavage domain. Optionally, the endonuclease activity of such hybrid can be abolished.

Domain of Mono-dodecapeptide Meganuclease/Domain of Mono-dodecapeptide Meganuclease A ninth embodiment concerns a hybrid meganuclease comprising or consisting of a first domain derived from the domain of a mono-dodecapeptide meganuclease (A) and a second domain derived from the domain of the same or another mono-dodecapeptide meganuclease (B), said first and second domains being bound by a convenient linker. The first and the second domains are linked by either a convenient linker or a connecting loop from any di-dodecapeptide meganuclease Y, for example the loop of I-Dmo I meganuclease. A convenient linker is preferably flexible. Said flexible linker essentially comprises glycine, serine and threonine residues. Short flexible linker can also be introduced between the loop and the domains. The linker is preferably attached at one end to the helix following the 4-stranded β-sheet of the DBM of the domain of the meganuclease A and at the other end at the helix $\alpha^D$ of the domain of the meganuclease B. The resulting hybrid meganuclease comprises, from the N-terminal end to C-terminal end, the domain of the meganuclease A deleted from the variable sequence VA located downstream of the DBM of B, a linker or a connecting loop and the domain of the meganuclease B. Such hybrid meganuclease schematically comprises:

| V, optional | $\alpha^D$ | DBM | L | $\alpha^{'D}$ | DBM' | V', optional |
|---|---|---|---|---|---|---|
| A | αA | A | Y | αB | B | B |

A, B and Y indicating the meganuclease at the origin of the segment V, $\alpha^D$, DBM, L, $\alpha^{'D}$, DBM', V'. αA and αB refer to the $\alpha^D$ of the N-terminal domain and α'A and α'B refer to the $\alpha^{'D}$ of the C-terminal domain. For "DBM" column, the letter (N) and (C), respectively, indicate the origin from the N-terminal domain and the C-terminal domain.

In an alternative embodiment, the helices $\alpha^D$ and $\alpha^{'D}$ of the hybrid meganuclease can be a mixture of the two initial meganucleases. The amino acid residues from the helices $\alpha^D$ and $\alpha^{'D}$ which are directed towards the helix interface are those of one meganuclease for both helices (those of $\alpha^D$ from the meganuclease A or B). Optionally, the residues at the interface could be derived from another pair of dodecapeptide helices from a mono- or di-dodecapeptide meganuclease X. Within each domain, the amino acid residues from the helices $\alpha^D$ and $\alpha^{'D}$ which are directed towards the inside of the domain are those corresponding to the residues found at that position in that domain of the meganuclease it comes from (those of $\alpha^D$ from the meganuclease A and B). Such hybrid meganuclease schematically comprises:

| Type | V, optional | $\alpha^D$ intra | $\alpha^D$ inter | DBM | L | $\alpha^{'D}$ inter | $\alpha^{'D}$ intra | DBM' | V', optional |
|---|---|---|---|---|---|---|---|---|---|
| 1 | A | αA | αA | A | Y | αA | αB | B | B |
| 2 | A | αA | αB | A | Y | αB | αB | B | B |
| 3 | A | αA | αX | A | Y | α'X | αB | B | B |
| 4 | A | αA | αX | A | Y | αX | αB | B | B |

A, B, Y and X indicating the meganuclease at the origin of the segment V, $\alpha^D$, DBM, L, $\alpha^{'D}$, DBM', V'. "inter" refers to the residues of $\alpha^D$ and $\alpha^{'D}$ towards the interface between the domains, and "intra" refers to the residues of $\alpha^D$ and $\alpha^{'D}$ towards the inside of each domain. αA and αB refer to the $\alpha^D$ of the N-terminal domain and α'A and α'B refer to the $\alpha^{'D}$ of the C-terminal domain. For "DBM" column, the letter (N) and (C), respectively, indicate the origin from the N-terminal domain and the C-terminal domain.

Optionally, some amino acid modifications can be further introduced in order to avoid the steric hindrance between amino acid side chains and/or to increase the stability. Optionally, some amino acid modifications can be further introduced in order to enhance the production and/or the solubility and to decrease the toxicity (Turmel et al, 1997, *Nucleic Acod Research*, 25, 2610-2619).

Optionally, such hybrid meganuclease comprising a first domain from the domain of a mono-dodecapeptide meganuclease (A) and a second domain from the domain of another mono-dodecapeptide meganuclease (B) can further comprise, at its N-terminal and/or C-terminal end, a loop or linker and any additional domain. Preferably, said additional domain is a DNA binding domain, a transcription activator or repressor domain, a nuclear localization domain or a DNA cleavage domain. Optionally, the endonuclease activity of such hybrid can be abolished.

An example of hybrid meganuclease, more particularly a hybrid meganuclease comprising a first domain derived from the N-terminal domain of a di-dodecapeptide meganuclease (A) and a second domain derived from the C-terminal domain of another di-dodecapeptide meganuclease (B), is disclosed in example 1 for the I-Dmo I/I-Cre I hybrid meganuclease. An example of one way for introducing said linker between two domains is disclosed in example 2 for the single chain I-Cre I meganuclease.

Alternative engineering strategies are possible. For example, a flexible linker could be a sequence comprising a number of glycine, serine and threonine amino acids. A disadvantage, not present in our method, could be the need, in this case, to determine and eventually optimize for each domain combination the precise linker sequence and length, together with the connections to the protein domains.

Our preferred strategy is based on structural analyses and comparison of the parent proteins that are "domain swapped". Another approach requires aligning the sequences of two proteins in the regions that most certainly correspond to motifs of conserved structures. For instance, sequence conservation of the dodecapeptide motifs is related to the persistent presence of an inter-domain two-helix bundle. Domain swapped endonucleases can be engineered by exchanging protein sequences somewhere within the second dodecapeptide motif, or directly prior to that motif where a linker region must be present.

The invention also contemplates the use of such hybrid meganuclease essentially as recognition domain. In this case, the endonculease catalytic activity of the hybrid meganuclease can be abolished by some mutation, for example the acidic residues D/E which are necessary for the catalytic activity.

In one particular embodiment, the invention concerns a chimeric protein comprising one domain derived from a dodecapeptide meganuclease, a linker and an helix comprising the dodecapeptide motif. Optionally, said linker is a loop from a di-dodecapeptide meganuclease. Optionally, said chimeric protein further comprises an additional domain. Said additional domain is preferably a DNA binding domain, a transcription activator or repressor domain, a nuclear localization signal, or a DNA cleavage domain Single-Chain Meganucleases In the present invention, we disclose a Single-chain meganuclease derived from "mono-dodecapeptide" meganucleases. The "mono-dodecapeptide" meganucleases are active as homodimer. Each monomer mainly dimerizes through their dodecapeptide motifs. This single-chain meganuclease covalently binds two monomers of a "mono-dodecapeptide" meganuclease modified such as to introduce a covalent link between the two sub-units of this enzyme. Preferably, the covalent link is introduced by creating a peptide bond between the two monomers. However, others convenient covalent link are also contemplated by the present invention. The invention concerns a single-chain meganuclease comprising a first and a second domain in the orientation N-terminal toward C-terminal, wherein said first and second domains are derived from the same mono-dodecapeptide meganuclease and wherein said single-chain meganuclease is capable of causing DNA cleavage. The single-chain meganuclease can comprise two sub-units from the same meganuclease such as single-chain I-Cre and single-chain I-Ceu I. The single-chain I-Ceu II is also contemplated by the invention. See example 2 for the single-chain I-Cre I. The invention concerns a single chain meganuclease of I-Cre comprising the sequence of SEQ ID No. 6. A single-chain meganuclease has multiple advantages. For example, a single-chain meganuclease is easier to manipulate. The single-chain meganuclease is thermodynamically favored, for example for the recognition of the target sequence, compared to a dimer formation. The single-chain meganuclease allows the control of the oligomerisation. Same principles of hybrid meganucleases apply to the single chain meganuclease. More particularly, see hybrid meganuclease comprising a first domain derived from the domain of a mono-dodecapeptide meganuclease (A) and a second domain derived from the domain of the same or another mono-dodecapeptide meganuclease (B).

The invention also relates to variants of the hybrid or single chain meganuclease according to the present invention. Preferably, the variants of hybrid or single chain meganuclease comprise a core of the meganuclease consisting of the two domains and the linker having at least 70% of identity with the initial hybrid or single chain meganuclease, more preferably at least 80, 90, 95 or 99% of identity. The variant may be 1) one in which one or more of the amino acid residues are substituted with a conserved or non-conserved amino acid residue and such substituted amino acid residue may or may not be one encoded by the genetic code, or 2) one in which one or more of the amino acid residues includes a substituent group, or 3) one in which the hybrid or single chain meganuclease is fused with another compound, such as a compound to increase the half-life of the polypeptide (for example, polyethylene glycol), or 4) one in which the additional amino acids are fused to the hybrid meganuclease, such as a leader or secretory sequence or a sequence which is employed for purification of the hybrid meganuclease. Such variants are deemed to be within the scope of those skilled in the art. In the case of an amino acid substitution in the amino acid sequence of a hybrid or single chain meganuclease according to the invention, one or several amino acids can be replaced by "equivalent" amino acids. The expression "equivalent" amino acid is used herein to designate any amino acid that may be substituted for one of the amino acids having similar properties, such that one skilled in the art of peptide chemistry would expect the secondary structure and hydropathic nature of the polypeptide to be substantially unchanged. Generally, the following groups of amino acids represent equivalent changes: (1) Ala, Pro, Gly, Glu, Asp, Gln, Asn, Ser, Thr; (2) Cys, Ser, Tyr, Thr; (3) Val, Ile, Leu, Met, Ala, Phe; (4) Lys, Arg, His; (5) Phe, Tyr, Trp, His. A modifed hyrbid or single chain meganuclease is a peptide molecule which is resistant to proteolysis, a peptide in which the-CONH-peptide bond is modified and replaced by a (CH2NH) reduced bond, a (NHCO) retro inverso bond, a (CH2-O) methylene-oxy bond, a (CH2-S) thiomethylene bond, a (CH2CH2) carba bond, a (CO—CH2) cetomethylene bond, a (CHOH—CH2) hydroxyethylene bond), a (N—N) bound, a E-alcene bond or also a—CH═CH— bond. The invention also encompasses a hyrbid or single chain meganuclease in which at least one peptide bound has been modified as described above.

The present invention concerns any cell or non-human animal comprising a hybrid or single chain meganuclease according to the present invention. The present invention also comprises any pharmaceutical composition comprising a hybrid or single chain meganuclease according to the present invention.

Polynucleotides Encoding Hybrid and Single Chain Meganucleases, Vectors, Cells and Animals The present invention concerns a recombinant polynucleotide encoding a hybrid or single chain meganuclease according to the present invention. Among these polynucleotides, the invention concerns a polynucleotide comprising a sequence selected from the group consisting of SEQ ID No. 1, 3 and 5.

The present invention concerns:

a) any vector comprising a polynucleotide sequence encoding a hybrid or single chain meganuclease according to the present invention;

b) any prokaryotic or eukaryotic cell comprising either a polynucleotide sequence encoding a hybrid or single chain meganuclease according to the present invention or said vector comprising said polynucleotide sequence;

c) any non-human animal comprising a polynucleotide sequence encoding a hybrid or single chain meganuclease according to the present invention, a vector comprising said polynucleotide, or a cell comprising either said polynucleotide or a vector comprising said polynucleotide.

The vector comprising a polynucleotide encoding a hybrid or single chain meganuclease contains all or part of the coding sequence for said a hybrid or single chain meganuclease operably linked to one or more expression control sequences whereby the coding sequence is under the control of transcriptional signals to permit production or synthesis of said hybrid or single chain meganuclease. Therefore, said polynucleotide encoding a hybrid or single chain meganuclease is comprised in an expression cassette. More particularly, the vector comprises a replication origin, a promoter operatively linked to said encoding polynucleotide, a ribosome-binding site, an RNA-splicing site (when genomic DNA is used), a polyadenylation site and a transcription termination site. It also can comprise an enhancer. Selection of the promoter will depend upon the desired route for expressing the hybrid or single chain meganuclease.

The invention concerns a method for producing a hybrid or single chain meganuclease comprising introducing an expression vector into a cell compatible with the element of said expression vector.

The polynucleotide sequence encoding the hybrid or single chain meganuclease can be prepared by any method known.

For example, the polynucleotide sequence encoding the hybrid or single chain meganuclease can be prepared from the polynucleotide sequences encoding the initial meganucleases by usual molecular biology technologies.

Preferably the polynucleotide sequence encoding the hybrid or single chain meganuclease is preferably generated by well-known back or reverse-translation methods. Number of back-translation softs are available, for example in the GCG sequence analysis package (University of Wisconsin, Madison, Wis).; in DNA strider, in EMBOSS (European Molecular Biology Open Software Suite: http://www.hgmp.mrc.ac.uk/Software/EMBOSS/Apps/backtranseq.html); etc . . . ). The obtained polynucleotide sequence can be synthetized through any method well known by the man skilled in the art.

Hybrid Recognition and Cleavage Sites

The hybrid meganucleases according to the present invention recognize and cleave a hybrid site or target comprising the half sites recognized by each domains comprised in the hybrid meganuclease.

The recognition sites of the meganucleases are not palyndromic. For a di-dodecapeptide meganuclease A, the N-terminal and C-terminal domains recognize two different half recognition sites; herein called "Site $L_A$" and "Site $R_A$". The indicated sequences for the initial half sites generally correspond to the sequence of the strand + of the genome. "L" refers to the left part of the site and "R" to the right part. Therefore, the site of the meganuclease A can be described as Site $L_A$-Site $R_A$. By "RC Site" is intended in the present invention the reverse complementary sequence of the half site on the + strand of the genomic target site.

The orientation of the parental molecules onto their respective recognition and cleavage site is not always well defined or known. Thus, preferably, several half-site combinations have to be synthesized and subjected to cleavage. For example, for an hybrid meganuclease comprising a first domain derived from a domain of a di-dodecapeptide meganuclease A and a second domain derived from a domain of a di-dodecapeptide meganuclease B, the following target sites will be preferably used;

Site $L_A$-Site $R_B$
RC Site Rhd A-Site $R_B$
Site $L_A$-RC Site $L_B$
RC Site $R_A$-RC Site $L_B$.

When the orientation is known, the hybrid site can be easily defined without any combination. The determination of the orientation can be determined by the generation of hybrid meganuclease and the study of their specificity on the several targets of the above mentioned combination. See example 3 (I-Dmo 1/I-Cre I) for a way of determination of the respective orientation of the meganuclease and the recognition site.

In order to test the endonuclease activity and specificity, synthetic target site corresponding to the fusion of parental half sites or a combination thereof is synthesized and cloned into a vector or use as such.

The invention concerns an isolated or recombinant polynucleotide comprising a hybrid target site according to the present invention. This hybrid target site comprises two half sites from the initial meganucleases, one per meganuclease. The invention also concerns a vector comprising a hybrid target site according to the present invention. The invention further concerns a cell comprising a recombinant polynucleotide or a vector comprising a hybrid target site according to the present invention. The invention further concerns a non-human animal comprising a recombinant polynucleotide or a vector comprising a hybrid target site according to the present invention. The invention further concerns a plant comprising a recombinant polynucleotide or a vector comprising a hybrid target site according to the present invention.

When nothing is known about the recognition and cleavage site, the following method could be applied in order to define this site.

Homing intron-encoded meganuclease of the dodecapeptide family, recognize and cleave normally a sequence present in a gene without intron, said intron comprising the encoding sequence for the meganuclease. In fact, the target sequence for the meganuclease is represented by the junction of upstream and downstream exon, naturally present in the gene without intron. The double strand break, for this class of meganuclease, occurs inside the recognition site.

In the absence of data on the extension of the recognition site, the length of the recognition site should be 30 nucleotides on the left part (upstream exon) and 30 nucleotides on the right side (downstream exon) meaning 60 nucleotides to test the binding and/or the cleavage of the protein. The recognition sequence should be centered around the position of the intron insertion point in the gene without intron.

In the particular case of inteins (PI), the canonical target should be represented by the junction, at the DNA level, of the sequence encoding the two extein and should be of equivalent size of the previous site (about 30+30=60 nucleotides total). In the absence of data on the recognition site, one difference with the determination of the site of intron-encoded meganucleases, could be the presence of a cystein codon (observed in a large number of cases) in the middle of the recognition sequence (TGT or TGC).

In the case of hybrid-meganucleases, the canonical target sequence, should be represented by the junction between the two half-site of each original meganuclease.

In Vitro Cleavage Assay

The recognition and cleavage of a specific DNA sequence by the hybrid and/or single chain meganucleases according to the present invention can be assayed by any method known by the man skilled in the art. One way to test the activity of the hybrid and/or single-chain meganuclease is to use an in vitro cleavage assay on a polynucleotide subtrat comprising the recognition and cleavage site corresponding to the assayed meganuclease. Said polynucleotide substrat is a synthetic target site corresponding to the fusion of parental half sites which is synthesized and cloned into a vector. This vector, once linearized by a restriction enzyme, and then incubated with the hybrid. Said polynucleotide substrat can be linear or circular and comprises preferably only one cleavage site. The assayed meganuclease is incubated with the polynucleotide substrat in appropriate conditions. The resulting polynucleotides are analyzed by any known method, for example by electrophoresis on agarose or by chromatography. The meganuclease activity is detected by the apparition of two bands (products) and the disappearance of the initial full-length substrate band. Preferably, said assayed meganuclease is digested by poteinase K, for example, before the analysis of the resulting polynucleotides. In one embodiment, the target product is prepared with the introduction of a polynucleotide comprising the recognition and cleavage sequence in a plasmid by TA or restriction enzyme cloning, optionnally following by the linearization of the plamid. Preferably, such linearization is not done in the surrounding of the target site. See Wang et al, 1997, Nucleic Acid Research, 25, 3767-3776; In materials & Methods "I-CreI endonuclease activity assays" section, the disclosure of which is incorporated herein by reference) and the characterization papers of the considering meganucleases.

The orientation of the initial meganuclease onto their respective recognition and cleavage site is not always known (for example, does Nterm I-DmoI bind the left or right half part of its site?). Thus, several half-site combinations have to be synthesized and subjected to cleavage.

In Vivo Cleavage Assay

The recognition and cleavage of a specific DNA sequence by the hybrid and/or single-chain meganucleases according to the present invention can be assayed by any method known by the man skilled in the art. One way to test the activity of the hybrid and/or single-chain meganuclease is to use an in vivo a Single-strand annealing recombination test (SSA). This kind of test is known by the man skilled in the art and disclosed for example in Rudin et al (*Genetics* 1989, 122, 519-534); Fishman-Lobell & Haber (*Science* 1992, 258, 480-4); Lin et al (*Mol. Cell. Biol.*, 1984, 4, 1020-1034) and Rouet et al (*Proc. Natl. Acad. Sci. USA,* 1994, 91, 6064-6068); the disclosure of which is incorporated herein by reference. This test could be applied for assaying any endonuclease, preferably rare-cutting endonuclease.

To test the hybrid and/or single-chain meganucleases according to the present invention, we developed an in vivo assay based on SSA in an eukaryotic cell, namely a yeast cell or a higher eukaryotic cell such as mammalian cells. In one preferred embodiment of the in vivo assay, the method uses a yeast cell. This organism has the advantage recombine naturally its DNA via homologous recombination with a high frequency.

This in vivo test is based on the reparation by SSA of a reporter marker induced by site-specific double-stand break generated by the assayed meganuclease at its recognition and cleavage site. The target consists of a modified reporter gene with an internal duplication separated by a intervening sequence comprising the recognition and cleavage site of the assayed meganuclease. The internal duplication should contain at least 50 bp, preferably at least 200 bp, more preferably at least 300 or 400 bp. The efficiency of the SSA test will be increased by the size of the internal duplication. The intervening sequences at and preferably less than 2 kb. Preferably, the size of the intervening sequence, which comprises least the recognition and cleavage site, is between few bp to 1 kb, more preferably among 500 bp. The intervening sequence can optionally comprise a selection marker (for example, neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase for eukaryotic cell culture; TRP1 or URA3 for *S. cerevisiae*; tetracycline, rifampicin or ampicillin resistance in *E. coli*; etc . . . ). By reporter gene is intended any nucleic acid encoding a product easily assayed, for example β-galactosidase, luciferase, alkaline phosphatase, green fluorescent protein, tyrosinase, DsRed proteins. The reporter gene is preferably operably linked to a constitutive promoter relating to the cell used in the assay (for example CMV promoter). According to the present assay method, the reporter will be detected only if a SSA event occurs following the double-strand break introduced by the assayed meganuclease.

The assayed meganuclease is introduced in an expression cassette. Preferably this expression cassette is on a separate construct. The meganculease encoding sequence can be operably linked to an inducible promoter or to a constitutive promoter. Of course, the promoter needs to be compatible with the cell used in the assay. In a prefered embodiment, the construct is comprised by a plasmid.

Optionally, each construct can comprise a selectable marker to ensure the presence of the plasmid in the cell. The presence of this selectable marker is required for the asssay proceeded in yeast cell. For example, for yeast, the first construct comprising the target gene can comprise a Leu2 selectable marker allowing transformed yeast to grow on a synthetic medium that does not contain any Leucine and the second construct can comprise the Trp1 selectable marker allowing transformed yeast to grow on a synthetic medium that does not contain any tryptophane.

The two constructs are used to transform simultaneously an appropriate cell. If the meganuclease is expressed and recognizes its cleavage site on the reporter construct, it can promote double-stand break and site-specific recombination between the target sequences by a mechanism known as Single-Strand Annealing. The resulting reporter gene should then express fully active reporter protein. Control experiments can be done with construct that does not express any meganuclease gene and reporter construct with no recognition and cleavage site.

The example 4 disclosed the use of a target consisting of a modified beta-galactosidase gene with a 900 pb internal duplication separated by the Ura3 selectable marker and a cleavage site for the assayed meganuclease (single-chain I-Cre I).

The recognition and cleavage by the hybrid and/or single-chain meganucleases according to the present invention can be also assayed with a gene convertion assay. For example, the reporter construct comprises a first modified reporter gene with a deletion and an insertion of an intervening sequence at the place of the deletion. This intervening sequence comprises the recognition and cleavage site of the assayed meganuclease. The reporter construct further comprises the fragment of the reporter gene which has been deleted flanked at each side by the reporter gene sequences bordering the deletion. The bordering sequences comprises at least 100 bp of homology with the reporter gene at each side, preferably at least 300 pb. The induction of a site-specific double-stand break generated by the assayed meganuclease at its recognition and cleavage site will trigger to a gene convertion event resulting in a functional reporter gene. This kind of assay are documented in the following articles: Rudin et al (*Genetics* 1989, 122, 519-534), Fishman-Lobell & Haber (*Science* 1992, 258, 480-4), Paques & Haber (*Mol. Cell. Biol.,* 1997, 17, 6765-6771), the disclosures of which are incorporated herein by reference.

Otherwise, the recognition and cleavage by the hybrid and/or single-chain meganucleases according to the present invention can be assayed through a recombination assay on chromosomic target. The recombination can be based on SSA or gene convertion mechanisms. For example, a mutated non-functional reporter gene comprising a recognition and cleavage site for the assayed meganuclease is introduced into the chromosome of the cell. Said cleavage site has to be in the vicinity of the mutation, preferably at less than 1 kb from the mutation, more preferably at less than 500 bp, 200 bp, or 100 pb surrounding the mutation. By transfecting the cell with a fragment of the functional reporter gene corresponding to the mutation and an expression construct allowing the production of the assayed meganuclease in the cell, the repair by homologous recombination of the double-strand break generated by the assayed meganuclease will lead to a functional reporter gene, said reporter gene expression being detected. This kind of assay is documented in the following articles: Rouet et al (*Mol. Cell. Biol.,* 1994, 14, 8096-8106); Choulika et al (*Mol. Cell. Biol.,* 1995, 15, 1968-1973); Donoho et al (*Mol. Cell. Biol.,* 1998, 18, 4070-4078); the disclosures of which are incoporated herein by reference.

Search of Hybrid Meganuclease for a Target Gene or Virus

The present invention discloses new methods to discover novel targets for natural or hybrids of meganucleases in a targeted locus of a virus genome and other genomes of interest, more particularly in a gene thereof. Indeed, from the large number of LAGLIDADG meganuclease, the hybrid meganucleases allow to generate a high diversity of target sites. These new target sites are rare in the genome of interest, preferably almost unique, and are useful for several applications further detailed below.

A database comprising all known meganucleases target sites is prepared. Preferably, such database comprises the target sites that have been experimentally shown to be cleaved by a meganuclease. A second database is designed comprising all possible targets for hybrid meganucleases. Such targets for hybrid meganucleases can be designed as disclosed above.

From these databases, an alignment is done to find homologous sequences without gaps, said homologous sequences having an identity of at least 70%, preferably 80%, more preferably 90%, still more preferably 95%. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default settings.

Use of Meganucleases

The hybrid meganuclease according to the present invention can be used for molecular biology and for genetic engineering and gene therapy, more particularly according to the methods described in WO 96/14408, U.S. Pat. No. 5,830,729, WO 00/46385, WO 00/46386 and provisional application filed on Oct. 26, 2001 60/330639 and on Sep. 14, 2001 60/318818; the disclosure of these documents being incorporated by reference.

A very interesting use of the hybrid meganuclease is for targeting a particular genomic locus of interest. Indeed, the induction of a double stranded break at a site of interest in chromosomal DNA of the cell is accompanied by the introduction of a targeting DNA homologous to the region surrounding the cleavage site with a high efficient. The hybrid meganuclease can be used for targeting a particular genomic locus comprising the hybrid target site. Hybrid meganucleases according to the present invention can be used in methods involving the induction in cells of double stranded DNA cleavage at a specific site in chromosomal DNA. For more detailed, see WO 96/14408, U.S. Pat. No. 5,830,729, WO 00/46386. The hybrid meganuclease can be used in a method of genetic engineering comprising the following steps: 1) introducing a double-stranded break at the genomic locus comprising the hybrid target site with the corresponding hybrid meganuclease; 2) providing a targeting DNA construct comprising the sequence to introduce flanked by homologous sequence to the targeting locus. Indeed, the homologous DNA is at the left and right arms of the targeting DNA construct and the DNA which modifies the sequence of interest is located between the two arms. Said hybrid meganuclease can be provided to the cell either through an expression vector comprising the polynucleotide sequence encoding said hybrid meganuclease and suitable for its expression in the used cell or the hybrid meganuclease itself.

The hybrid or single chain meganucleases according to the present invention can be used for the deletion of a viral genome or a part thereof. Indeed, a cut in the viral genome induces a recombination that can lead to the deletion of a part or the whole viral genome deletion. This method is generally called virus pop-out. Therefore, the hybrid meganucleases allow the targeting of the viral genome. See WO 96/14408 example 5. Therefore, the invention concerns a method of deleting a viral genome or a part thereof, wherein a double-strand break in the viral genome is induced by a meganuclease according to the present invention and said double-strand break induces a recombination event leading to the deletion of the viral genome or a part thereof.

For the determination of the relevant hybrid meganuclease in order to introduce a double-strand cleavage at a target locus or a target viral genome, see section the immediate previous section.

In another use, the hybrid and single chain meganucleases can be for in vivo excision of a polynucleotide fragment flanked by at least one, preferably two, hybrid target site. Hybrid meganucleases according to the present invention can be used in methods involving the excision of targeting DNA or polynucleotide fragment from a vector within cells which have taken up the vector. Such methods involve the use of a vector comprising said polynucleotide fragment flanked by at least one, preferably two, hybrid target site and either an expression vector comprising a polynucleotide encoding the hybrid and single chain meganuclease corresponding to the hybrid target site suitable for the expression in the used cell, or said hybrid and single chain meganuclease. Said excised polynucleotide fragment can be used for transgenesis as described in detail in provisional application filed on Oct. 26, 2001 60/330639 and on Sep. 14, 2001 60/318818. Said excised targeting DNA comprises homologous DNA at the left and right arms of the targeting DNA and the DNA which modifies the sequence of interest is located between the two arms. For more detail, see WO 00/46385. Said method of excision of targeting DNA from a vector within the cell can be used for repairing a specific sequence of interest in chromosomal DNA, for modifying a specific sequence or a gene in chromosomal DNA, for attenuating an endogeneous gene of interest, for introducing a mutation in a target site, or for treating or prohylaxis of a genetic disease in an individual.

The present invention also relates to the resulting cells and to their uses, such as for production of proteins or other gene products or for treatment or prophylaxis of a condition or disorder in an individual (e. g. a human or other mammal or vertebrate) arising as a result of a genetic defect (mutation). For example, cells can be produced (e. g., ex vivo) by the methods described herein and then introduced into an individual using known methods. Alternatively, cells can be modified in the individual (without being removed from the individual).

The invention also relates to the generation of animal models of disease in which hybrid meganuclease sites are introduced at the site of the disease gene for evaluation of optimal delivery techniques.

EXAMPLES

Example 1

I-Dom I/I-Cre I Hybrid Meganuclease

I-Dmo I/I-Cre I Hybrid Meganuclease Design

I-DmoI is a thermostable endonuclease encoded by an intron in the 23S rRNA gene of the hyperthermophilic archaeon *Desulfurococcus mobilis* (Dalgaard et al., 1993, *Proc Natl Acad Sci USA*, 90, 5414-5417). I-DmoI belongs to the LAGLIDADG family of meganucleases. Its structure, solved by X-ray crystallography (pdb code 1b24) (Silva et al., 1999, *J Mol Biol*, 286, 1123-1136), consists of two similar α/β domains (αββαββα) related by pseudo two-fold symmetry. A dodecapeptide motif is located at the C-terminal end of the first α-helix in each domain. These helices form a two-helix bundle at the interface between the domains and are perpendicular to a saddle-shaped DNA binding surface formed by two four-stranded antiparallel β-sheets (FIG. 1).

I-CreI is another LAGLIDADG meganuclease, encoded by an open reading frame contained within a self-splicing intron in the *Chlamydomonas reinhardtii* chloroplast 23S rRNA gene (Durrenberger and Rochaix, 1991, *Embo J*, 10, 3495-3501). However, unlike most members of this protein family, I-CreI contains a single copy of the dodecapeptide motif, and functions in a dimeric form. I-CreI dimers display the overall architecture of single chain LAGLIDADG proteins (FIG. 2) (Chevalier et al., 2001, *Nat Struct Biol*, 8, 312-316; Heath et al., 1997, *Nat Struct Biol*, 4, 468-476; Jurica et al., 1998, *Mol Cell*, 2, 469-476). Each monomer corresponds to a single domain, providing one of the two four-stranded antiparallel β-sheets for DNA-binding, and the dodecapeptide motifs are within α-helices at the inter-domain interface.

As they display similar overall topology, the structures of I-DmoI and I-CreI can be superimposed to low (local) root mean square deviation (RMSD), each monomer from I-CreI finely matching one of the two domains from I-DmoI. An optimal structural match (RMSD=0.66 Å, FIG. 3) was obtained superimposing the following atoms (residue numeration corresponds to either pdb structures, and for I-CreI, residues in the second monomer are shifted by 200 with respect to those in the first monomer):

| Source residues | Target residues | Atoms superimposed |
|---|---|---|
| I-DmoI, 14-22 | I-CreI, 13-21 | N, Cα, C, O |
| I-DmoI, 110-118 | I-CreI, 213-221 | N, Cα, C, O |
| I-DmoI, Tyr13 | I-CreI, Tyr12 | N, Cα, C, O, Cβ, Cγ |
| I-DmoI, Phe109 | I-CreI, Tyr212 | N, Cα, C, O, Cβ, Cγ |

The low RMSD is a strong indication of the similarity of the two dodecapeptide inter-domain packing interfaces. The dodecapeptide motifs and corresponding α-helices aligned sequences are:

| Motifs | Sequences |
|---|---|
| I-DmoI, 1$^{st}$ dodecapeptide α-helix | SGISAY$_{13}$LLGLIIGDG |
| I-DmoI, 2nd dodecapeptide α-helix | EQIAF$_{109}$IKGLYVAEG |
| I-CreI, dodecapeptide α-helix (1$^{st}$ monomer) | NKEFLLY$_{12}$LAGFVDGDG |
| I-CreI, dodecapeptide α-helix (2$^{nd}$ monomer) | NKEFLLY$_{212}$LAGFVDGDG |

Visual inspection of the superimposition indicated that a hybrid of both proteins may be formed, by replacing the second I-DmoI domain with the corresponding I-CreI monomer. The I-DmoI sequence, starting from some point (the swap point) within the loop that connects both DNA binding domains or within the second dodecapeptide α-helix that follows, should be replaced by that of I-CreI starting at a corresponding point. We chose to swap the domains at the beginning of the second dodecapeptide motif. The resulting hybrid protein sequence was the protein sequence of I-DmoI up to Phe109 (included) and the protein sequence of I-CreI from Leu213 (included). Residues from I-CreI that precede Leu213 were thus removed. See FIG. 6A for the amino acid (SEQ ID No. 2) and polynucleotide sequences (SEQ ID No. 1) of such hybrid.

In a modeled structure, the novel inter-domain packing interface presented only little defects, e.g. no amino acid side chain has steric clashes that should not easily relax, except perhaps for Ile107 (I-DmoI) that has overlaps with Phe294 (I-CreI). In order to suppress the resulting potentially unfavorable repulsion, the isoleucine residue is replaced by a leucine amino acid (the aligned amino acid residue in I-CreI). Eventually, the inter-domain linker sequence is as follows:

| I-DmoI | Linker (I-DmoI) | I-CreI |
|---|---|---|
| (N-term) . . . YYFA | NMLERIRLFNMREQLAF SEQ ID N° 7 | LAGF . . . (C-term) |

Furthermore, Leu47, His51 and Leu55 (I-DmoI) are too close to Lys296 (I-CreI). This is uncertain, however, as distortion of the protein main chain structure (the I-DmoI region where residues 47, 51 and 55 are located) may indicate the structure is not fully reliable. Nevertheless, a second version of the hybrid protein is designed, which includes three additional mutations: L47A, H51A and L55D. Choices of alanine amino acids were made to stabilize the α-helical conformation of the corresponding residues. The third mutation (acid aspartic) should lead to the formation of an inter-domain salt-bridge to Lys296, thereby providing added stabilization. See FIG. 6B for the amino acid (SEQ ID No. 4) and polynucleotide sequences (SEQ ID No. 3) of such hybrid.

Hybrid I-Dmo I/I-Cre I Meganuclease Production

Solutions

Sonication solution: 25 mM HEPES (pH 7.5), 5% (v/v) glycerol, 0,1% (v/v) anti-proteases solution;

Solution A: 25 mM HEPES (pH 7.5), 5% (v/v) glycerol,

Storage solution: 25 mM HEPES (pH 7.5), 20% (v/v) glycerol

Standard reaction solution: 12,5 mM HEPES (pH 7.5), 2,5% (v/v) glycerol, 5-10 mM MgCl$_2$;

Standard stop solution (10×): 0.1 M Tris-HCl pH 7.5, 0.25 M EDTA, 5% (w/v) SDS, 0.5 mg/ml proteinase K.

Plasmids

An expression plasmid (pET 24 d(+) Novagen) was engineered to produce I-DmoI/I-CreI hybrid meganuclease with or without an histidin tag. Briefly, a fragment containing the ORF sequence and flanked by NcoI and EagI or XhoI restriction sites was prepared using the polymerase chain reaction (PCR) and specific oligonucleotides. Firstly, the half I-DmoI and I-CreI sequences were prepared by PCR then I-DmoI/I-CreI hybrid sequence was completed by another PCR.

Expression and Purification of I-DmoI/I-CreI Hybrid Meganuclease

*Escherichia coli* strain BL21(DE3) RIL was used for the purification of I-DmoI/I-CreI. Clones transformed with the I-DmoI/I-CreI plasmid (pET 24 d(+) Novagen) were grown in 250 ml of Luria Broth containing 30 mg/ml kanamycin at 37° C. with shaking.

When the culture reached an A$_{600}$ of 0.8-1.2, expression was induced by adding IPTG to a final concentration of 1 mM, and after 5 h to 15 h at 25° C., the cells were harvested by centrifugation.

The following procedures were performed at 4° C. unless stated otherwise. The harvested cells were resuspended in 25 ml of ice-cold sonication solution, and then sonicated for 5 minutes. The lysate was centrifuged at 105 000 g for 30 min. The supernatant recovered, and then subjected to a second ultracentrifugation at 105 000 g for 30 min. This supernatant, which contained 90% of the protein, was called the 'soluble' fraction.

The soluble fraction was applied to a 5 ml Hi-Trap chelating column (Amersham, Uppsala, Sweden) load with cobalt at a flow rate of 2,5 ml/min (Amersham—Pharmacia FPLC Akta purifier 10). After washing the column with 25 ml of solution A, bound proteins were eluted with a 0-0.25 M linear immidazole gradient made up in solution A following by an elution step at 0,5M immidazole-0,5M NaCl. Fractions were collected, and the amounts of protein and I-DmoI/I-CreI activity (see below) were determined. The column fractions were also analyzed by SDS-PAGE. The fractions containing most of the I-DmoI/I-CreI activity were pooled and concentrated using a 10 kDa cut-off centriprep Amicon system. This concentrated fraction was purified was applied to a Superdex75 PG Hi-Load 26-60 column (Amersham, Uppsala, Sweden) at a flow rate of 1 ml/min (Amersham—Pharmacia FPLC Akta purifier 10) of solution A. Fractions were collected, and the amounts of protein and I-DmoI/I-CreI activity (see below) were determined. The column fractions were also analyzed by SDS-PAGE. The fractions containing most of the I-DmoI/I-CreI activity were pooled and concentrated using a 10 kDa cut-off centriprep Amicon system. Then dialysed against storage solution over-night, and stored in aliquots in liquid nitrogen.

SDS-polyacrylanide Gel Electrophoresis

Figure 8A:
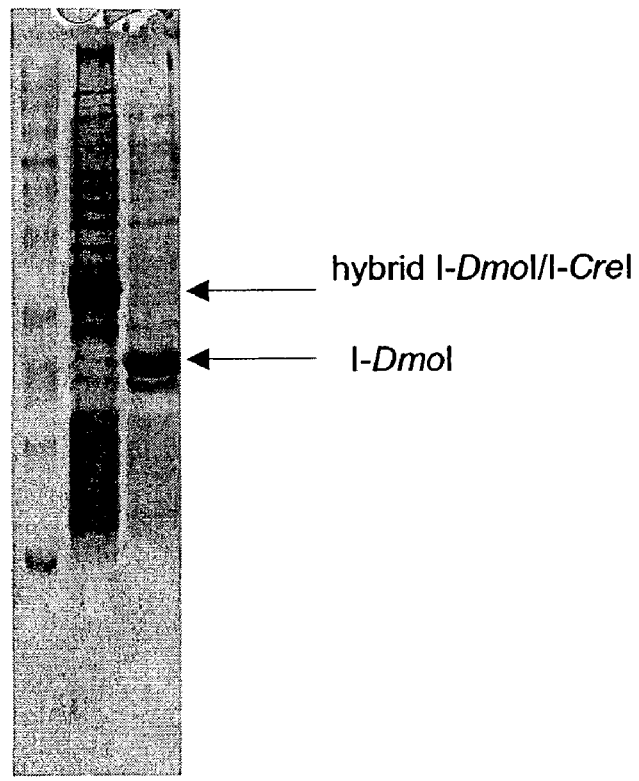
FIG. 8A: Line A: molecular weight markers; Line B: Hybrid meganuclease I-Dmo I/I-Cre I; Line C: Wild type meganuclease I-Dmo I.

SDS-polyacrylamide gel electrophoresis (SDS-PAGE) was performed as described by Laemmli using 15% acrylamide gels. Gels were stained with coomassie brilliant blue. FIG. 8A shows that the hybrid meganuclease I-DmoI/I-CreI is well expressed and that this hybrid is obtained in the supernatant and therefore is soluble.

Size of I-DmoHI-CreI Hybrid Meganuclease

The molecular weight of I-DmoI/I-CreI in solution was estimated by size-exclusion chromatography of the purified protein. The column fractions were analyzed by SDS-PAGE, and the 31,2 kDa band eluted primarily, which corresponded to a molecular mass of 30 kDa. Thus, this analysis indicated that I-DmoI/I-CreI is mainly a momomer.

Example 2

Single-Chain I-Cre I Meganuclease

Single Chain I-Cre I Megcanuclease Design

Figure 2:
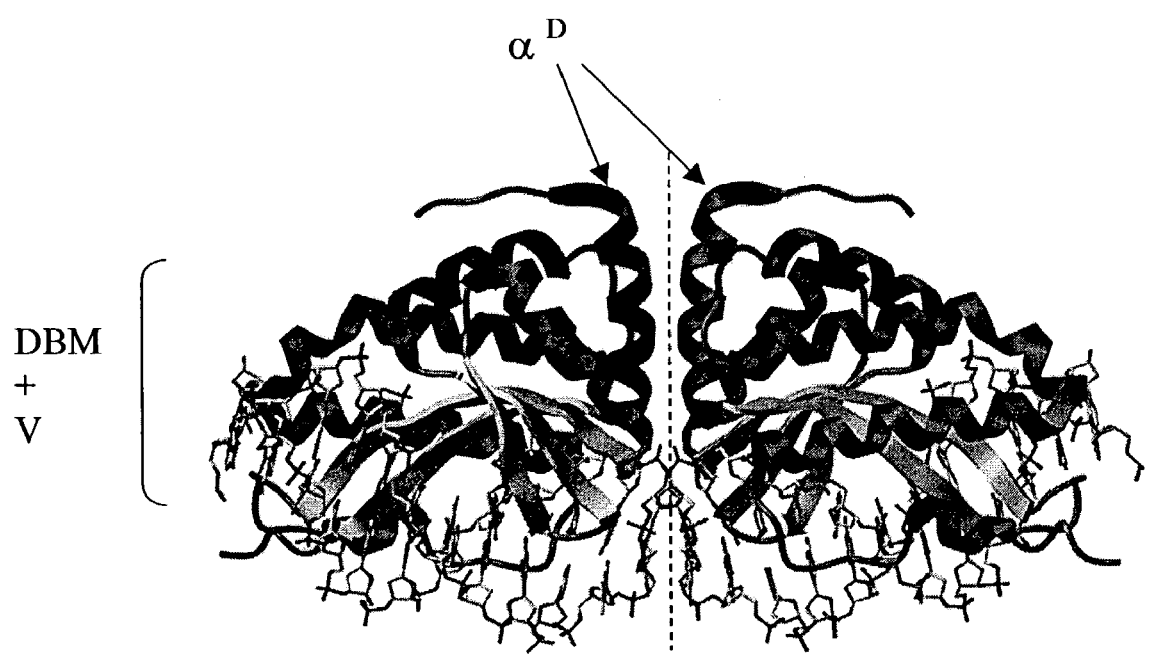
FIG. 2 is a ribbon representation of dimeric I-CreI with bound DNA in stick representation (pdb code 1g9y). The discontinuous line represents the two-fold symmetry axis between the two domains or monomers. The bound DNA lies perpendicular to the symmetry axis below the two β-sheets (arrows). $\alpha^D$ refers to helix comprising the dodecapeptide motif, DBM to DNA binding moiety, and V to variable sequence.
Figure 4:
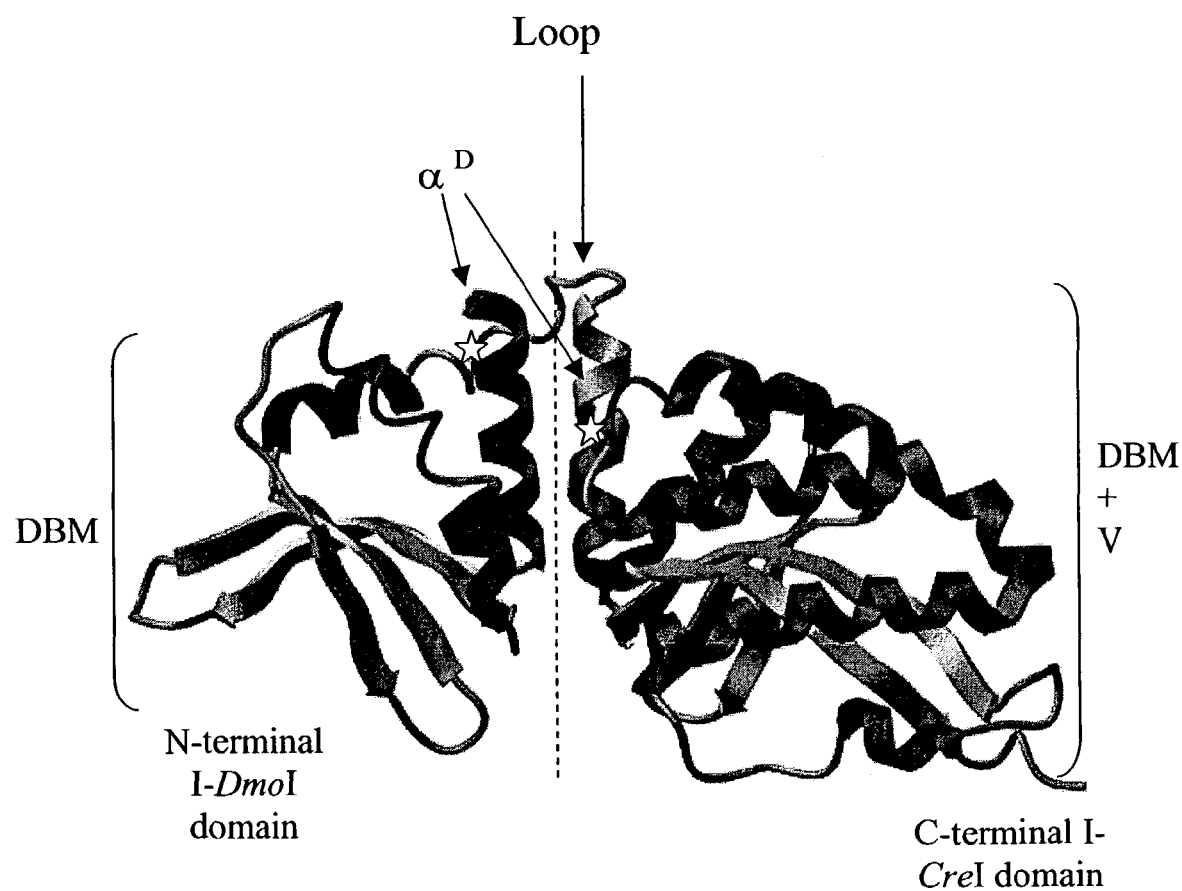
FIG. 4 is a ribbon representation of the I-DmoI/I-CreI hybrid protein (model structure built by juxtaposition of the two domains taken from their respective X-ray structures). The linker joining both domains, which is the end of the I-DmoI part, is between the two stars. The discontinuous line represents the two-fold symmetry axis between the two protein domains. The N-term domain of I-DmoI is left and the I-CreI domain right of the axis. $\alpha^D$ and $\alpha'^D$ refer to helices comprising the dodecapeptide motif, DBM to DNA binding moiety, and V to variable sequence.

I-CreI is a single LAGLIDADG protein domain that dimerizes (FIG. 2). For the domain swapping strategy, we planned to connect an I-CreI domain to any other LAGLIDADG domain. Engineering a single chain I-CreI protein, by placing a connecting link between the two monomers, was complementary to the example I. This did not provide a protein with novel DNA binding specificity. Instead, the resulting artificial protein illustrated that natural single LAGLIDADG proteins can be effectively thought of as the two halves of a larger double LAGLIDADG protein. If a fusion of the two domains was functional, swapping the domains from different single LAGLIDADG, between such proteins or with domains from double LAGLIDADG proteins, should be straightforward.

Each I-CreI domain comprises a C-terminal sub-domain made of three α-helices, which may be present in the C-terminal domain of double LAGLIDADG proteins, but cannot be part of the N-terminal domain. The N-terminal domain of these proteins is indeed shorter, as the loop or linker connecting the two domains stands in place of the three α-helices. The three helices terminate at opposite sides of the dimer structure, far away from the N-terminal helices of the dodecapeptide motifs. The length of a flexible linker connecting the C-terminal residue of one domain to the N-terminal residue of the other domain (end-to-end fusion) would be considerable. Besides, engineering such linker would be difficult due to the necessity to go across a large part of the protein surface. Therefore, it is uncertain that proper domain packing be obtained.

The structural superimposition of I-DmoI and I-CreI discussed in the previous example, allowed to design a simple linker solution. The loop region from I-DmoI itself, residues 96 to 103 (sequence ERIRLFNM), may replace the C-terminal fragment of one I-CreI domain and lead to the N-terminal region of the second domain (as it does in the I-DmoI/I-CreI hybrid protein, except that the residues at the beginning of the I-CreI α-helix need not and should not be replaced). On both side of the loop, residues from I-DmoI and I-CreI can be well aligned and superimposed. These residues are:

| Source residues | Sequence | Target residues | Sequence | Atoms superimposed |
|---|---|---|---|---|
| I-DmoI, 93-95 | N<u>M</u>L | I-CreI, 93-95 | P<u>F</u>L | N, Cα, C, O |
| I-DmoI, 104-106 | REQ | I-CreI, 207-209 | KEF | N, Cα, C, O |

The link between the I-CreI domains should thus be chosen to replace the C-terminal residues of the first domain and the N-terminal residues of the second, respectively from either Pro93, Phe94 or Leu95 and up to Lys207, Glu208 or Phe209. Actually, amino acids at two of the superimposed positions are identical (Leu95 in both proteins and Glu105 from I-DmoI with Glu208 from I-CreI; underlined residues), and at a third position they are sufficiently similar to be equivalent (Arg104 and Lys207 from I-DmoI and I-CreI, respectively; underlined residues).

The lysine 98 of the first domain I-CreI has been removed despite of the disclosure of Jurica et al (1998, *Mol. Cell.*, 2, 469-476) saying that Lysine 98 in I-CreI which is a well-conserved residue and is close to the active (cleavage) site could have a functional role.

Proline 93 is not an optimal residue for the α-helical conformation of the main chain at that residue position. The corresponding asparagine in I-DmoI is only slightly better; particular hydrogen bonding properties of the amino acid establish a pronounced tendency to promote a N-terminal break in α-helices. At that position, an alanine residue is eventually preferred (glutamic acid would be another suitable amino acid, which has good intrinsic propensity to adopt a α-helical conformation and could form a stabilizing salt-bridge with Arg97 in the following linker region).

Figure 5A:
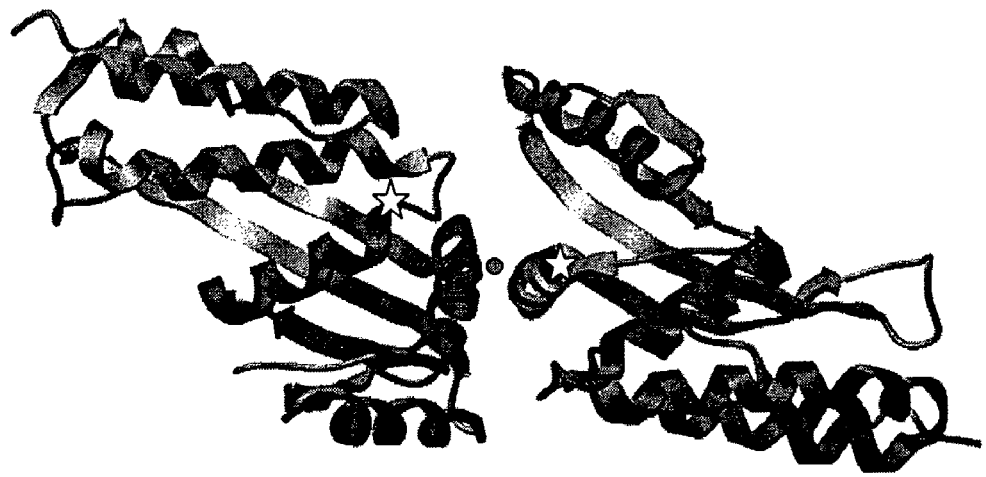
FIGS. 5A and 5B respectively are ribbon representations of the I-CreI dimer (1g9y) and the single chain I-CreI (modelled structure).
Figure 5B:
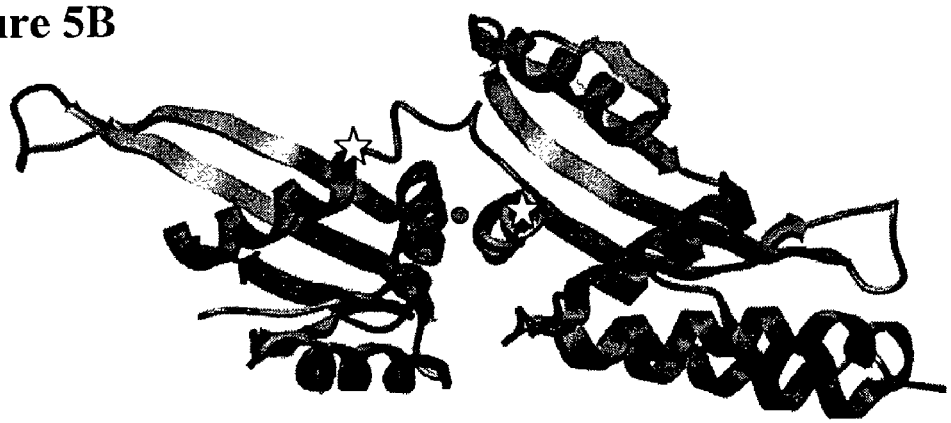

A single chain version of I-CreI was thus engineered so as to introduce the I-DmoI bridge, starting with Met94 and up to Glu105, between a shortened version of the natural I-CreI domain (truncation after the Pro93Ala mutation) and a nearly complete copy of that domain (truncation before Phe209) (FIG. 5 and FIG. 7 for the amino acid (SEQ ID No. 6) and polynucleotide sequences(SEQ ID No. 5)). Met94 replaced a bulkier phenylalanine amino acid that is buried into the I-CreI protein dimer. Both amino acids appear to fit equally well, and could be tried alternatively at that sequence position. Another non-polar amino acid, isoleucine at position 98 (I-DmoI numeration) packs into the original dimer structure without creating any atomic overlaps. Residue 101, an aromatic phenylalanine, is equally fine but could be replaced by another aromatic amino acid, tyrosine, which could then form a stabilizing hydrogen bond to the main chain carbonyl group of residue 94. The following sequences are thus alternative solutions to provide a linker region between two I-CreI domains:

| I-CreI | Linker | I-CreI |
|---|---|---|
| (N-term)...TQLQ | AMLERIRLFNMR (SEQ ID N° 8) | EFLL...(C-term) |
| (N-term)...TQLQ | AFLERIRLFNMR (SEQ ID N° 9) | EFLL...(C-term) |
| (N-term)...TQLQ | AMLERIRLYNMR (SEQ ID N° 10) | EFLL...(C-term) |
| (N-term)...TQLQ | AFLERIRLYNMR (SEQ ID N° 11) | EFLL...(C-term) |

Figure 9A:
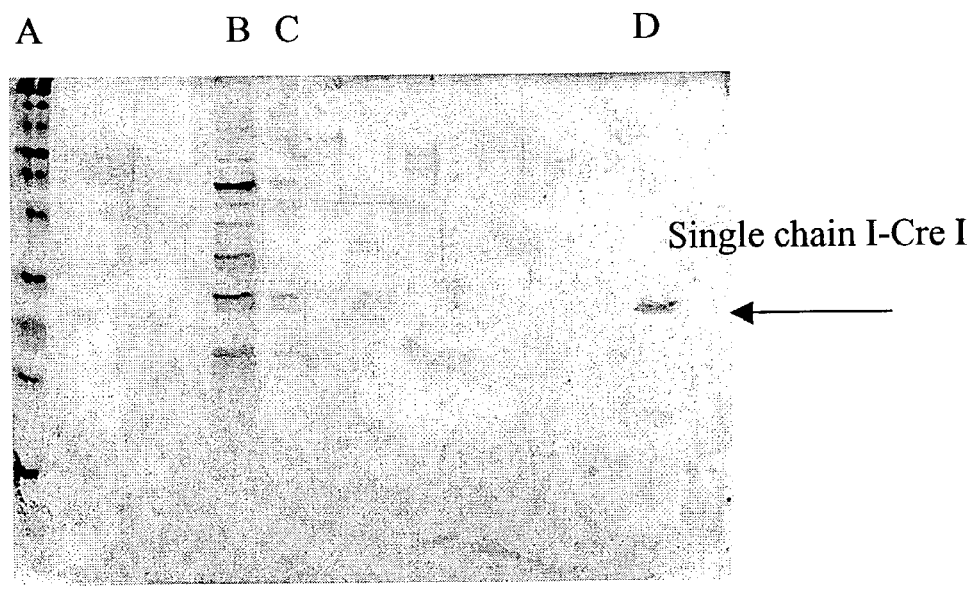
FIG. 9A: Line A: molecular weight markers; Lines B and C: dead colume of gel filtration. Line D: single chain meganuclease I-Cre I.

Single Chain I-Cre I Meganuclease Production
Solutions
Sonication solution: 25 mM HEPES (pH 7.5), 5% (v/v) glycerol, 0,1% (v/v) anti-proteases solution;
Solution A: 25 mM HEPES (pH 7.5), 5% (v/v) glycerol,
Storage solution: 25 mM HEPES (pH 7.5), 20% (v/v) glycerol
Standard reaction solution: 12,5 mM HEPES (pH 7.5), 2,5% (v/v) glycerol, 5-10 mM $MgCl_2$;
Standard stop solution (10×): 0.1 M Tris-HCl pH 7.5, 0.25 M EDTA, 5% (w/v) SDS, 0.5 mg/ml proteinase K.
Plasmids
An expression plasmid (pET 24 d(+) Novagen) was engineered to produce Single chain I-CreI (Sc I-CreI) with or without an histidine tag. Briefly, a fragment containing the ORF sequence and flanked by NcoI and EagI or XhoI restriction sites was prepared using the polymerase chain reaction (PCR) and specific oligonucleotides. Firstly, the two half modified I-CreI sequences were prepared by PCR then the single chain I-CreI hybrid sequence was completed by another PCR.
Expression and Purification of Sc I-CreI (Sc=Single Chain)
*Escherichia coli* strain BL21(DE3) RIL was used for the production and the purification of Sc I-CreI polypeptide. Clones transformed with the Sc I-CreI plasmid (pET 24 d(+) Novagen) were grown in 250 ml of Luria Broth containing 30 mg/ml kanamycin at 37° C. with shaking.
When the culture reached an $A_{600}$ of 0.8-1.2, expression was induced by adding IPTG to a final concentration of 1 mM, and after 5 h to 15 h at 20° C., the cells were harvested by centrifugation.
The following procedures were performed at 4° C. unless stated otherwise. The harvested cells were resuspended in 25 ml of ice-cold sonication solution, and then sonicated for 5 minutes. The lysate was centrifuged at 105 000 g for 30 min. The supernatant recovered, and then subjected to a second ultracentrifugation at 105 000 g for 30 min. This supernatant, which contained 90% of the protein, was called the 'soluble' fraction.
The soluble fraction was applied to a 5 ml Hi-Trap chelating column (Amersham, Uppsala, Sweden) load with cobalt at a flow rate of 2,5 ml/min (Amersham—Pharmacia FPLC Akta purifier 10). After washing the column with 25 ml of solution A, bound proteins were eluted with a 0-0.25 M linear immidazole gradient made up in solution A following by an elution step at 0,5M immidazole-0,5M NaCl. Fractions were collected, and the amounts of protein and Sc I-CreI activity (see below) were determined. The column fractions were also analyzed by SDS-PAGE. The fractions containing most of the Sc I-CreI activity were pooled and concentrated using a 10 kDa cut-off centriprep Amicon system. This concentrated fraction was purified was applied to a Superdex75 PG Hi-Load 26-60 column (Amersham, Uppsala, Sweden) at a flow rate of 1 ml/min (Amersham—Pharmacia FPLC Akta purifier 10) of solution A. Fractions were collected, and the amounts of protein and Sc I-CreI activity (see below) were determined. The column fractions were also analyzed by SDS-PAGE. The fractions containing most of the Sc I-CreI activity were pooled and concentrated using a 10 kDa cut-off centriprep Amicon system. Then dialysed against storage solution overnight, and stored in aliquots in liquid nitrogen.
SDS-polyacrylamide Gel Electrophoresis
SDS-polyacrylamide gel electrophoresis (SDS-PAGE) was performed as described by Laemmli using 15% acrylamide gels. Gels were stained with coomassie brilliant blue. (FIG. 9A)
Size of Sc I-CreI Meganuclease
The molecular weight of Sc I-CreI in solution was estimated by size-exclusion chromatography of the purified protein. The results of the sizing column are summarized in FIG. 2A. The column fractions were analyzed by SDS-PAGE, and the 31,4 kDa band eluted primarily, which corresponded to a molecular mass of 30 kDa. Thus, this analysis indicated that Sc I-CreI is mainly a momomer.

Example 3

Cleavage Assay

In Vitro Cleavage Assay
Endonuclease Activity Assays of Hybrid I-Dmo I/I-Cre I Meganuclease
Plasmid pGEMtarget (3.9 kb), was constructed by TA or restriction enzyme cloning of the target product, obtained by PCR or single strain hybridation. The target products comprise the following recognition and cleavage sites:

|  |  |
|---|---|
| | SEQ ID N° 12 |
| wild type I-Cre I | CAAAACGTCGT GAGACAGTTTGGTCCA |
| | SEQ ID N° 13 |
| wild type I-Dmo I | CCTTGCCGGGT AAGTTCCGGCGCGCAT |
| | SEQ ID N° 14 |
| $L_{(I\text{-}Dmo\ I)}/R_{(I\text{-}Cre\ I)}$ target | CCTTGCCGGGT GAGACAGTTTGGTCCA |
| | SEQ ID N° 15 |
| $L_{(I\text{-}cre\ I)}/R_{(I\text{-}Dmo\ I)}$ target | CAAAACGTCGT AAGTTCCGGCGCGCAT |

Figure 8B:
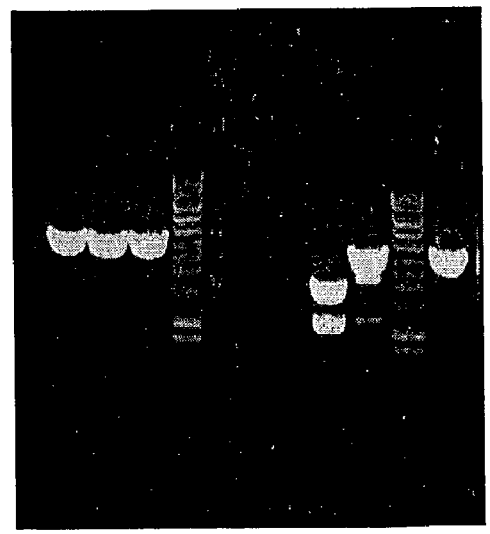
FIG. 8B: Agarose gel activity of hybrid I-Dmo I/I-Cre I; lines A, B, C, D: target I-Dmo I/I-Cre I; lines E, F, G, H: target I-Cre I/I-Dmo I; lines D, G: size markers; lines C, H: linear plasmid; lines B, F: assay at 37° C.; lines A, E: assay at 65° C.

This plasmid was used for the cleavage assays. It was isolated with the Quiagen Maxipreps DNA Purification System (Qiagen). For most experiments, it was linearized with XmnI prior to the assay. Standard I-DmoI/I-CreI assays were performed at 37° C. in the standard reaction solution (solution A 0.5×, add $MgCl_2$ 5 to 10 mM), stopped with 0.1 vol of 10× standard stop solution, and the products separated by electrophoresis in 1% agarose/ethidium bromide gels at room temperature. The fluorescence was captured with camera using a transilluminator.
One unit of endonuclease activity (U) was defined as the amount of I-DmoI/I-CreI necessary to cleave 200 ng of target DNA in 60 min at 37° C. in the same assay condition than I-CreI wild-type. Activity assays were also performed at 65° C. as I-DmoI optimal temperature for DNA cleavage.
The I-DmoI/I-CreI hybrid meganuclease specifically cleaves the target I-CreI/I-DmoI and does not cleave the wild type targets of I-Dmo I, I-Cre I, and I-Sce I meganucleases and the target I-DmoI/I-Cre I. These results are shown in FIG. 8B. Thus, the I-DmoI/I-CreI hybrid meganuclease shows a high specificity for its new target sequence. The I-DmoI/I-CreI hybrid meganuclease cleaves the target I-CreI/I-DmoI at 37 and 65° C., but the cleavage is more rapid at 65° C. The new specificity of the I-DmoI/I-CreI hybrid meganuclease for the target I-CreI/I-DmoI allows the determination of the relative orientation of the wild type meganuclease I-Dmo I and its recognition and cleavage site. Indeed, the N-terminal domain of I-Dmo I meganuclease recognizes the second half domain of the target I-CreI/I-DmoI. Therefore, the N-terminal domain of I-Dmo I meganuclease recognize the right half site (R) and its C-terminal domain the left one (L).

Endonuclease Activity Assays of Single Chain I-Cre I Meganuclease

Plasmid pGEMtarget (3.9 kb), was constructed by TA or restriction enzyme cloning of the target product, obtained by PCR or single strain hybridation. The target product comprises the recognition and cleavage site

| | SEQ ID N° 12 |
|---|---|
| wild type I-Cre I | CAAAACGTCGT GAGACAGTTTGGTCCA |
| | SEQ ID N° 16 |
| wild type I-Sce I | TAGGGAT AACAGGGTAAT |

This plasmid was used for the cleavage assays. It was isolated with the Quiagen Maxipreps DNA Purification System (Qiagen). For most experiments, it was linearized with XmnI prior to the assay. Standard Sc I-CreI assays were performed at 37° C. in the standard reaction solution (solution A 0.5×, add $MgCl_2$ 5 to 10 mM), stopped with 0.1 vol of 10× standard stop solution, and the products separated by electrophoresis in 1% agarose/ethidium bromide gels at room temperature. The fluorescence was captured with camera using a transilluminator.

One unit of endonuclease activity (U) was defined as the amount of Sc I-CreI necessary to cleave 200 ng of target DNA in 60 min at 37° C. in the same assay condition than I-CreI wild-type. Activity assays were also performed at 65° C. to compare with the wild type I-CreI about effect of temperature on DNA cleavage.

Figure 9B:
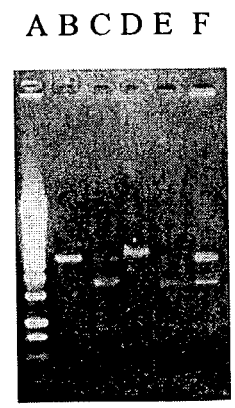
FIG. 9B: Agarose gel activity of single chain meganuclease; Line A: markers; Line B target site of wild type I-Cre I meganuclease; Line C: target site of wild type I-Cre I+wild type I Cre I meganuclease (positive control); Line D: target site of wild type I-Sce I+single chain I-Cre I meganuclease (negative control); Lines E and F: target site of wild type I-Cre I+single chain I-Cre I meganuclease, respectively, at 37 and 65° C. for lines E and F during 1 h.

The single chain meganuclease kept its specificty as this meganuclease did not cleave the I-Sce I target site and cleaved the wild type I-Cre I target site. These results are shown in FIG. 9B.

In Vivo Cleavage Assay in Yeast

Endonuclease Activity Assays of Single Chain I-Cre I Meganuclease

To test the meganucleases, we developed an in vivo assay the yeast *Saccharomyces cerevisiae*. This organism has the advantage to recombine naturally its DNA via homologous recombination.

This test was based on the reparation of a colorimetric marker induced by site-specific double-stand break by the meganuclease of interest.

Figure 10A:
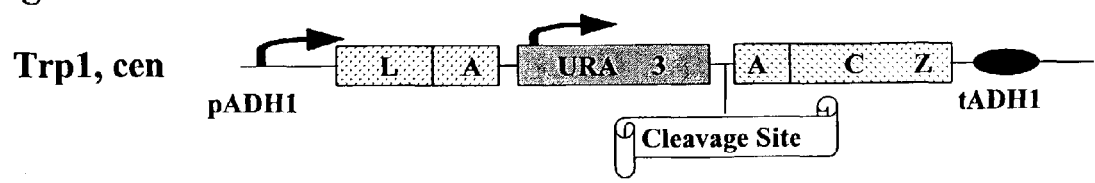
FIG. 10A is a schematic representation of the LACURAZ reporter contruct. LACZ represents the elements of the Lac Z gene. The sections A of each side of the intervening sequence comprise the internal duplication of the Lac Z gene. pADH1 is a yeast constitutive promoter. tADH1 is a yeast terminator. Ura3 represents the Ura3 gene. The arrows represent the transcription beginning. The tag "Cleavage site" refers to the recognition and cleavage site of the assayed meganuclease. "Trp1" refers to a Trp1 selectable marker and <<cen>> to an ARS-CEN origin of replication.

The target consisted of a modified beta-galactosidase gene with a 900 pb internal duplication separated by the Ura3 selectable marker and a cleavage site for the meganuclease to be studied (the resulting construct has been called LACURAZ) (FIG. 10A).

Figure 10B:
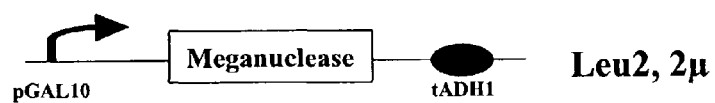
FIG. 10B is a schematic representation of the meganuclease inducible expression vector. pGAL10 is a yeast promoter which is inducible in presence of galactose. tADH1 is a yeast terminator. "Leu2" and "2µ" respectively refer to a Leu2 selectable marker and a 2µ origin of replication. The arrow represents the transcription beginning.

The meganuclease was expressed under the control of a galactose-inducible promoter from a nuclear expression plasmid which carried the Leu2 selectable marker allowing transformed yeast to grow on a media that do not contain any Leucine, and a 2μ origin of replication (FIG. 10B). The expression of the reporter gene (LACURAZ) was controled by a constitutive promoter and was carried by another shuttle vector with the Trp1 selectable marker allowing transformed yeast to grow on a media that did not contain any tryptophane and an ARS-CEN origin of replication (FIG. 10A).

Figure 11:
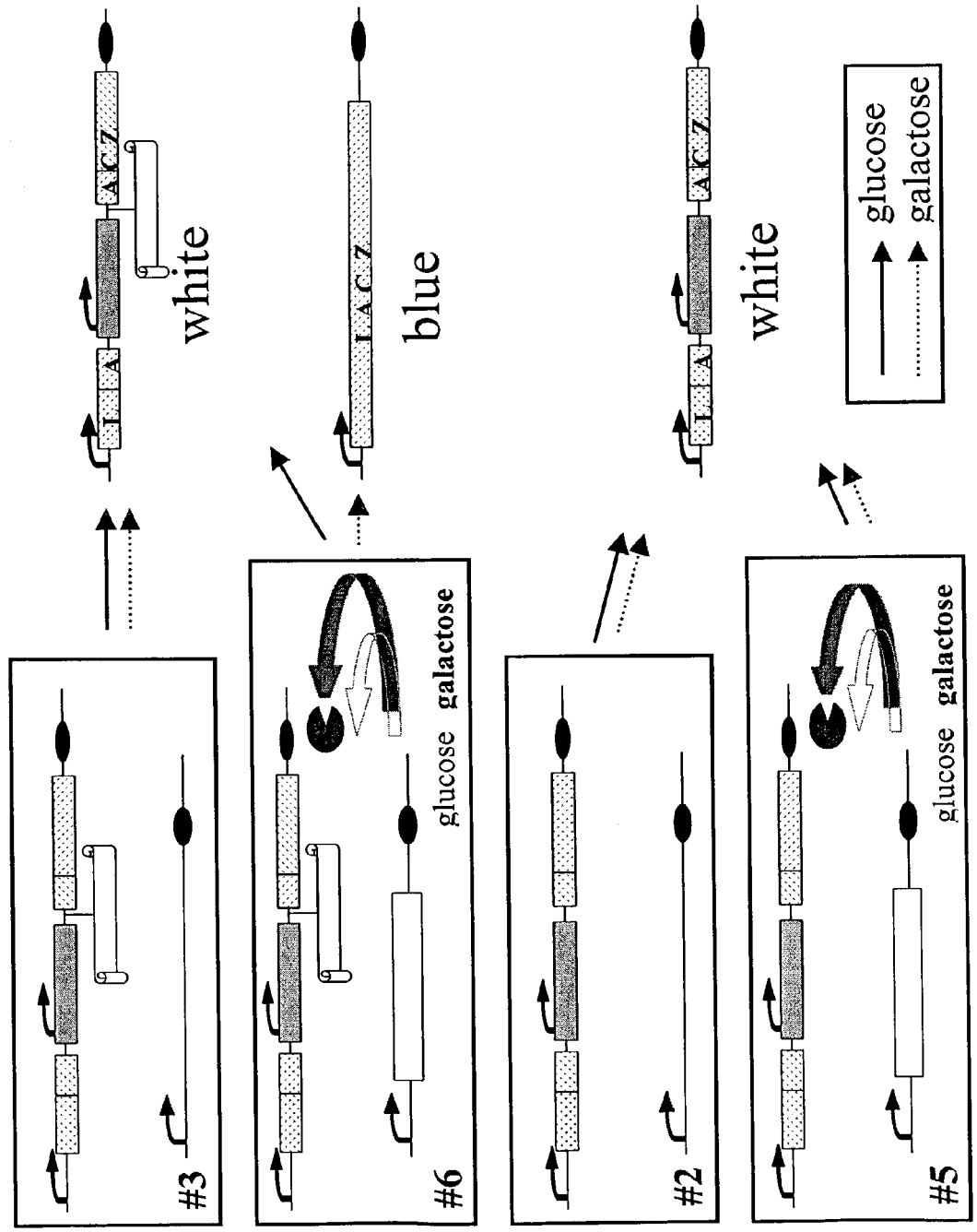
FIG. 11 shows the combinations of co-transformations and subsequent modifications of the reporter gene. <<#X>> refers to the combination disclosed in Table A. The light grey boxes refer to Ura3 gene. The dark grey boxes refer to the Lac Z gene. The white boxes refer to the gene encoding the meganuclease. The white tags refer to the recognition and cleavage site of the assayed meganuclease.

The two constructs were used to transform simultaneously an appropriate yeast strain. If the meganuclease is expressed (or overexpressed after induction on a galactose media) and recognizes its cleavage site on the reporter construct, it can promote double-stand break and site-specific recombination between the target sequences by a Single-Strand Annealing mechanism. The resulting reporter gene should then express fully active beta-galatosidase. We also prepared all the control experiments with plasmids that do not express any meganuclease gene and reporter construct with no cleavage site (all the possible event are described in FIG. 11).

The assay is performed as follow:

The yeast was co-transfected with the expression plasmid and the reporter plasmid. The co-transformants were selected, and the presence of the two plasmids was achieved by selection on a synthetic media containing no Leucine nor Tryptophane (Table A). In addition, two sets of media were used allowing the overexpression of the meganuclease gene or not (i.e. on selective media with different carbone source: galactose to induce the expression of the meganuclease or glucose). When colonies were big enough, an overlay assay revealed the presence or absence of the beta-galactosidase activity.

Theorically, beta-galactosidase activity should only be detected when a meganuclease and its own recongnition site are present in the same yeast cell (except the natural background of autonomous recombination of the reporter construct) (see FIG. 10).

Following this schema, we subcloned the I-CreI Singlechain gene into our galactose inducible plasmid as well as the I-CreI recognition site in our reporter construct and co-transfected both plasmids into our yeast strain. (As a control we use an I-CreI gene on the same reporter construct).

TABLE A

Number of tranformation per assay

| Reporter Construct/ Expression Vector | Empty plasmid | LACURAZ control with no cleavage site | LACURAZ + cleavage site |
|---|---|---|---|
| Empty plamid | #1 | #2 | #3 |
| Meganuclease's gene | #4 | #5 | #6 |

Each transformation is plated on glucose and galactose media.

Methods:
Yeast Cell Transformation

1. Inoculate 2-5 mls of liquid YPGlu or 10 ml minimum media and incubate with shaking overnight at 30° C.
2. Count on culture and inoculate 50 ml of warm YPGlu to a cell density of $5 \times 10^6$ cells/ml culture.
3. Incubate the culture at 30° C. on a shaker at 200 rpm until its equivalent to $2 \times 10^7$ cells/ml. This takes 3 to 5 hours. This culture gives sufficient cells for 10 transformations.
4. Harvest the culture in a sterile 50 ml centrifuge tube at 3000 g (5000 rpm) for 5 min.
5. Pour off the medium, resuspend the cells in 25 ml of sterile water and centrifuge again.
6. Pour off the water, resuspend the cells in 1 ml 100 mM LiAc (lithium acetate) and transfer the suspension to a 1.5 ml microfuge tube.
7. Pellet the cells at top speed for 15 sec and remove the LiAc with a micropipette.
8. Resuspend the cells to a final volume of 500 μl ($2 \times 10^9$ cells/ml) (about 400 μl of 100 mM LiAc).
9. Boil a 1 ml sample of Salmon Sperm-DNA for 5 min. and quickly chill in ice water.

10. Vortex the cell suspension and pipette 50 μl samples into labelled microfuge tubes. Pellet the cells and remove the LiAc with a micropipette.

11. The basic "transformation mix" consists of:
240 μl PEG (50% w/v)
36 μl 1.0 M. LiAc
50 μl SS-DNA (2.0 mg/ml)
X μl Plasmid DNA (0.1-10 μg)
34-X μl Sterile ddH2O
360 μl TOTAL Carefully add these ingredients in the order listed.

(One can also premix the ingredients except for the plasmid DNA then add 355 μl of "transformation mix" ontop of the cell pellet. Then add the 5 μl of plasmid DNA and mix. Take care to deliver the correct volume as the "transformation mix" is viscous).

12. Vortex each tube vigorously until the cell pellet has been completely mixed.

13. Incubate at 30° C. for 30 min.

14. Heat shock in a water bath at 42° C. for 30 min.

15. Microfuge at 6-8000 rpm for 15 sec and remove the transformation mix with a micropipette.

16. Pipette 1 ml of sterile YPGlu and let the cells at 30° C. for 1 to 2 hours. This allows you to have the same number of transformants growing on you glucose and galactose plates.

17. Microfuge at 6-8000 rpm for 15 sec and remove the supernatant.

18. Pipette 200 μl ml of sterile YPGlu 50% into each tube and resuspend the pellet by pipetting it up and down gently.

17. Plate 100 μl of the transformation onto selective plates.

18. Incubate the plates for 2-4 days to recover transformants.

X-Gal Agarose Overlay Assay

The following solution is given for 2 plates:
1. Microwave 5 ml of 1% agarose in water
2. Prepare the X-Gal mix with
5 ml of Sodium Phosphate buffer 1M
600 μl of Dimethyl Formamide (DMF)
100 μl of SDS 10%
3. Combine the agarose and the Mix and let cool down to 55° C. with agitation
4. When the above solution is ready, add 20 μl of X-Gal 10% in DMF
5. Using a plastic pipette, cover the surface of each plate of cells with 5 ml of the warm solution. 6. After the agar cools and solidifies, the plates may be incubated at either 25° C., 30° C. or 37° C. The blue color develops in a few hours, depending on the strength of the inducer.
7. Colonies may be picked through the top agar even 5 days later. Just take a sterile Pasteur pipette and poke it through the agar into the desired colony or patch. Then use the tip of the Pasteur pipette to streak a fresh plate and, despite the permeabilization, the cells will grow up.

Results:

| 1 - Control experiment with I-CreI: | | | |
|---|---|---|---|
| Reporter Construct/ Expression Vector | Empty plasmid | LACURAZ control with no cleavage site | LACURAZ + I-CreI cleavage site |
| Empty plamid | Glucose: white Galactose: white | Glucose: white Galactose: white | Glucose: white Galactose: white |
| I-CreI gene | Glucose: white Galactose: white | Glucose: white Galactose: white | Glucose: light blue Galactose: dark blue |

| 2 - Experiment with single-chain I-CreI | | | |
|---|---|---|---|
| Reporter Construct/ Expression Vector | Empty plasmid | LACURAZ control with no cleavage site | LACURAZ + I-CreI cleavage site |
| Empty plamid | Glucose: white Galactose: white | Glucose: white Galactose: white | Glucose: white Galactose: white |
| Single-chain I-CreI gene | Glucose: white Galactose: white | Glucose: white Galactose: white | Glucose: light blue Galactose: dark blue |

These results indicate that the Single-chain I-CreI gene allows the expression of an active meganuclease that behaves like the natural I-CreI molecule by recognizing and cutting its own cleavage site inducing homologous recombinaison of the reporter sequence. The light blue color is due to a very small expression of the meganuclease which is very stable in the cell. This small amount of protein allows the reporter construct to recombine leading to the production of a detectable β-galactosidase activity. On every "white" plate, some blue colonies appear at an average rate of $10^{-2}$. This background is due to the high spontaneous recombination in yeast.

In Vivo Cleavage Assay in Mammalian Cells

Endonuclease Activity of Single-Chain I-CreI Meganuclease

We also developed an assay in mammalian cells, based on the detection of homologous recombination induced by targeted double-strand break. As in the yeast system described above, we monitor the restoration of a functional LacZ marker resulting from the cleavage activity of the meganuclease of interest.

We first transferred the yeast reporter system in a mammalian expression plasmid. The LACZ repeat, together with the intervening sequence, including an I-CreI cleavage site, was cloned into pcDNA3 (Invitrogene). Thus, any functional LACZ gene resulting from recombination would be under the control of the CMV promoter of pcDNA3, and display also functional termination sequences. We also cloned the I-CreI and single-chain I-CreI open reading frames in pCLS3.1, a home-made expression vector for mammalian cells.

Using the Effectene (Qiagen) transfection kit, 0.5 μg of the reporter plasmid was cotransfected into simian COS cells, with 0.5 μg of pCLS3.1, 0.5 μg of the I-CreI expressing plasmid, or 0.5 μg of the single-chain I-CreI expressing plasmid. The beta-galactosidase activity was monitored 72 hours after transfection by an assay described below. In a control experiment, 0.5 μg of a reporter plasmid without any cleavage site was cotransfected with 0.5 μg of pCLS3.1, 0.5 μg of the I-CreI expressing plasmid, or 0.5 μg of the single-chain I-CreI expressing plasmid.

This assay is based on the detection of tandem repeat recombination, which often occurs by a process referred to as SSA (Single-strand Annealing). Therefore, we also designed an assay based on the detection of recombination between inverted repeats. Recombination between inverted repeats mostly occurs by gene conversion, another kind of recombination event.

A complete LacZ ORF, interrupted by an I-CreI cleavage site (and thus not functional) is introduced into pcDNA3, between the CMV promoter and the termination sequence. A truncated non functional copy of the gene is cloned in an inverted orientation, to provide an homologous donor template for gene conversion. It is not flanked by promoter and terminator sequences. It encompasses 2.5 Kb of the inner part of the LacZ ORF, overlapping the region where the I-CreI cleavage site is found in the other copy.

0.5 µg of the reporter plasmid was cotransfected into COS cells, with 0.5 µg of pCLS3.1, 0.5 µg of the I-CreI expressing plasmid, or 0.5 µg of the single-chain I-CreI expressing plasmid. In a control experiment, 0.5 µg of a reporter plasmid without any homologous donor template was cotransfected with 0.5 µg of pCLS3.1, 0.5 µg of the I-CreI expressing plasmid, or 0.5 µg of the single-chain I-CreI expressing plasmid.

The assay is performed as follow:

COS cells were transfected with Effectene transfection reagent accordingly to the supplier (Qiagen) protocol. 72 hours after transfection, cells were rinsed twice with PBS1× and incubated in lysis buffer (Tris-HCl 10 mM pH7.5, NaCl 150 mM, Triton X100 0,1%, BSA 0.1 mg/ml, protease inhibitors). Lysate was centrifuged and the supernatant used for protein concentration determination and β-galactosidase liquid assay. Typically, 30 µl of extract were combined with 3 µl Mg 100× buffer (MgCl$_2$ 100 mM, β-mercaptoethanol 35%), 33 µl ONPG 8 mg/ml and 234 µl sodium phosphate 0.1M pH7.5. After incubation at 37° C., the reaction was stopped with 500 µl of 1M Na$_2$CO$_3$ and OD was measured at 415 nm. The relative β-galactosidase activity is determined as a function of this OD, normalized by the reaction time, and the total protein quantity.

Results

| 1. Tandem repeat recombination: | | | | | | | | | | | | |
|---|---|---|---|---|---|---|---|---|---|---|---|---|
| Experiment | #1 | #2 | #3 | #4 | #5 | #6 | #7 | #8 | #9 | #10 | #11 | #12 |
| Reporter vector (with I-CreI cleavage site) | + | + | + | + | + | + | | | | | | |
| Reporter vector (without I-CreI cleavage site) | | | | | | | + | + | + | + | + | + |
| PCLS3.1 | + | + | | | | | + | + | | | | |
| PCLS3.1-I-CreI | | | + | + | | | | | + | + | | |
| PCLS3.1-single-chain-I-CreI | | | | | + | + | | | | | + | + |
| Beta-gal activity (units/mg prot) × 2 10$^{11}$ | 44 | 45 | 111 | 110 | 87 | 83 | 41 | 40 | 35 | 32 | 54 | 53 |

| 2. Inverted repeat recombination | | | | | | | | | | | | |
|---|---|---|---|---|---|---|---|---|---|---|---|---|
| Experiment | #1 | #2 | #3 | #4 | #5 | #6 | #7 | #8 | #9 | #10 | #11 | #12 |
| Reporter vector (with homologous template) | + | + | + | + | + | + | | | | | | |
| Reporter vector (without homologous template) | | | | | | | + | + | + | + | + | + |
| PCLS3.1 | + | + | | | | | ++ | | | | | |
| PCLS3.1-I-CreI | | | + | + | | | | | + | + | | |
| PCLS3.1-single-chain-I-CreI | | | | | + | + | | | | | + | + |
| Beta-gal activity (units/mg prot) × 2 10$^{11}$ | 8 | 9 | 29 | 32 | 24 | 21 | 4 | 4 | 4 | 5 | 4 | 4 |

These results indicates that the single-chain I-CreI stimulates can induce enough cleavage of an I-CreI cleavage site to stimulate homologous recombination between direct repeats as well as between inverted repeats.

With direct repeats, similar levels of induced recombination were observed with either the single-chain I-CreI (#5-6) or I-CreI (#3-4). This level of recombination represents a 2 to 2.5-fold increase compared to the background level of recombination of the reporter plasmid (#1-2). In addition, no such increase in the recombination level was observed with a reporter plasmid lacking an I-CreI cleavage site (#7-12).

With inverted repeats, the single-chain I-CreI (#5-6) and the I-CreI meganuclease (#3-4) induced a similar stimulation of gene conversion; with a 2.5 to 4-fold increase compared with background level (#1-2). As expected from a bona fide homologous recombination event, no stimulation was observed with a reporter plasmid lacking a homologous donor template (#7-12).

All references indicated or referred to herein are incorporated in their entirety herein by reference.

| Protein | Synonym | Organism | Species | Size (kD) | Motif | Acces N° (mega) | Access N° (gene) | Acces N° (genome) | Year | Reference |
|---|---|---|---|---|---|---|---|---|---|---|
| F-SceI | Endo.SceI | Saccharomyces | cerevisiae | 476 | DD | M63839 | | | 1991 | Nakagawa et al. J. Biol. Chem. 266:1977-1984 |
| F-SceII | HO | Saccharomyces | cerevisiae | 586 | DD | M14678 | | | 1983 | Kostriken et al. Cell 35:167-174 |
| I-AcaI | Aca1931m | Acanthamoeba | castellanii | 142 | D | AAA20591 | U03732 | NC_001637 | 1994 | Lonergan et al. J. Mol. Biol. 239(4), 476-499 |
| I-AcaII | Aca1951m | Acanthamoeba | castellanii | 168 | D | AAA20592 | U03732 | NC_001637 | 1994 | Lonergan et al. J. Mol. Biol. 239(4), 476-499 |
| I-AcaIII | Aca2593m | Acanthamoeba | castellanii | 164 | D | AAA20593 | U03732 | NC_001637 | 1994 | Lonergan et al. J. Mol. Biol. 239(4), 476-499 |
| I-AstI | | Ankistrodesmus | stipitatus | 244 | D | L42984 | | | | |
| I-CagI | Cag2593c | Chlamydomonas | agloeformis | 246 | D | L43351 | | | 2001 | Lucas et al. NAR Feb 15; 29(4):960-9 |
| I-CbrI | Cbr1931c | Chlorosarcina | brevispinosa | 153 | D | L49150 | | | 2001 | Lucas et al. NAR Feb 15; 29(4):960-9 |
| I-CbrII | Cbr1951c | Chlorosarcina | brevispinosa | 163 | D | L49150 | | | 2001 | Lucas et al. NAR Feb 15; 29(4):960-9 |
| I-CcaI | | Chlamydomonas | echinozigotum | | D? | | | | | |
| I-CecI | | Chlorococcum | elongatum | 213 | D | L44123 | | | | |
| I-CeuI | | Chlorogonium | eugametos | 229 | D | L42860 | | | 1991 | Gauthier et al. Curt Genet 19:43-7 |
| I-CeuII | I-CeuAII I-CeuAIIP | Chlamydomonas | eugametos | 218 | D | S14133 | Z17234 AF008237 | | 1998 | Denovan-Wright, et al. Plant Mol. Biol. 36:285-95 |
| I-CfrI | Cfr1931c | Chlamydomonas | frankii | 283 | D | L43352 | | | 2001 | Lucas et al. NAR Feb 15; 29(4):960-9 |
| I-CgeI | Cge1931c | Chlamydomonas | geitleri | 154 | D | L43353 | | | 2001 | Lucas et al. NAR Feb 15; 29(4):960-9 |
| I-ChuI | Chu1931c | Chlamydomonas | humicola | 177 | dd | L06107 | | | 1993 | Coté, et al. Gene 129:69-76 |
| I-CiyI | Ciy2593c | Chlamydomonas | iyengarii | 218 | D | L43354 | | | 2001 | Lucas et al. NAR Feb 15; 29(4):960-9 |
| I-CkoI | | Chlamydomonas | | 212 | D? | | | | | |
| I-CluI | Clu2593c | Carteria | luzensis | 225 | D | L42986 | | | | |
| I-CluII | Clu2593c | Carteria | luzensis | 171 | D | L42986 | | | 2001 | Lucas et al. NAR Feb 15; 29(4):960-9 |
| I-CmeI | Cme1931c | Chlamydomonas | mexicana | 140 | D | L49148 | | | 2001 | Lucas et al. NAR Feb 15; 29(4):960-9 |
| I-CmoI | | Chlamydomonas | monadina | 216 | D | L49149 | | | | |
| I-CmuI | | Chlamydomonas | mutabilis | 219 | D | L42859 | | | | |
| I-CmoeI | | Carteria | olivieri | 182 | D | L43500 | | | 2001 | Lucas et al. NAR Feb 15; 29(4):960-9 |
| I-CpaI | Col2593c | Chlamydomonas | pallidostigmatica | 152 | D | L36830 | | | 1995 | Turmel et al. Mol. Biol. Evol. 12:533-45 |
| I-CpaIII | | Chlamydomonas | pallidostigmatica | 214 | D | L43503 | | | | |
| I-CreI | | Chlamydomonas | reinhardtii | 163 | D | X01977 | | | 1985 | Rochaix et al. NAR 13:975-84 |
| I-CsmI | | Chlamydomonas | smithii | 237 | dd | X55305 | | | 1990 | Colleaux et al. Mol Gen Genet 223:288-296 |
| I-CvuI | I-CvuIP | Chlorella | vulgaris | 161 | D | L43357 | | | 1998 | Watanabe, et al. Gene 213:1-7 |
| I-CvuII | Cvu1931m | Chlorella | vulgaris | 144 | D | | AY008337 | | 2001 | Lucas et al. NAR Feb 15; 29(4):960-9 |
| I-CvuIII | Cvu1951m | Chlorella | vulgaris | 166 | D | | AY008338 | | 2001 | Lucas et al. NAR Feb 15; 29(4):960-9 |
| I-DmoI | | Desulfurococcus | mobilis | 194 | DD | P21505 | | | 1985 | Kjems, et al. Nature 318:675-77 |
| I-HlaI | Hla2593c | Haematococcus | lacustris | 166 | D | L49151 | | | 2001 | Lucas et al. NAR Feb 15; 29(4):960-9 |
| I-Mso | Mso1931m | Monomastix | species | 138 | D | L49154 | | | 1995 | |
| I-Mso | Mso1951m | Monomastix | species | 202 | D | | AY008339 | | 1995 | |
| I-MsoI | Mso1951c | Monomastix | species | 161 | D | L49154 | | | 1995 | |
| I-Msp | Msp1931m | Monomastix | species | 170 | D | L49154 | | | 1995 | |
| I-Msp | Msp1931m | Monomastix | species | 140 | D | L44124 | | | 1995 | |
| I-Msp | Msp1951c | Monomastix | species | 150 | D | L44124 | | | 1995 | |
| I-Msp | Msp2593c | Monomastix | species | 165 | D | | AY008340 | | 1995 | |
| I-MviI | Mvi2593m | Mesostigma | viride | 167 | D | L44124 | | | | |
| I-NcrIII | | Neurospora | crassa | 162 | D | AF323369 | | | 2001 | Lucas et al. NAR Feb 15; 29(4):960-9 |
| I-NolI | Nol1931m | Nephroselmis | olivacea | 425 | DD | S10841 | | | | |
| I-NolII | Nol2593m | Nephroselmis | olivacea | 157 | D | AF110138 | | | | |
| I-PakI | | Pseudendoclonium | akinetum | 164 168 | D D | AF110138 AAL34378 | L44125 | | 2001 | Lucas et al. NAR Feb 15; 29(4):960-9 |

| Protein | Synonym | Organism | Species | Size (kD) | Motif | Acces N° (mega) | Access N° (gene) | Acces N° (genome) | Year | Reference |
|---|---|---|---|---|---|---|---|---|---|---|
| I-PanI | | Podospora | anserina | 243 | dd | X55026 | | | 1985 | Cummings, et al. |
| I-PcrI | Pcr1931c | Pteroserpma | cristatum | 141 | D | L43359 | | | 2001 | Lucas et al. NAR Feb 15; 29(4):960-9 |
| I-PtuI | Ptu1931c | Pedinomonas | tuberculata | 145 | DD | L43541 | | | 2001 | Lucas et al. NAR Feb 15; 29(4):960-9 |
| I-ScaI | | Saccharomyces | capensis | 243 | dd | X95974 | | | 2000 | Monteilhet, et al. J Mol Biol 185:659-80 |
| I-SceI | | Saccharomyces | cerevisiae | 235 | DD | V00684 | | | 1985 | Jacquier & Dujon Nucleic Acids Res. 28:1245-1251 |
| I-SceII | | Saccharomyces | cerevisiae | 316 315 | DD | P03878 | | | 1980 | Bonitz et al. J Biol Chem 255:11927-41 |
| I-SceIII | | Saccharomyces | cerevisiae | 335 | DD | P03877 | | | 1980 | Bonitz et al. J Biol Chem 255:11927-41 |
| I-SceIV | | Saccharomyces | cerevisiae | 307 | dd | S78650 | | | 1992 | Séraphin et al. Gene 113:1-8 |
| I-SduI | Sdu2593c | Scherffelia | dubia | 167 | D | L44126 | | | 2001 | Lucas et al. NAR Feb 15; 29(4):960-9 |
| I-SexI | | Saccharomyces (Candida holmii) | exiguus | | | | | | 2000 | http://rebase.neb.com/rebase/rebase.homing.html |
| I-SneI | I-SneIP, Sne1931b | Simkania | negevensis | 143 | D | AAD38228 | U68460 | | 1997 | Everett, et al.Int. J. Syst. Bacteriol. 47(2), 461-473 |
| I-SobI | | Scenedesmus | obliquus | 221 | D | L43360 | | | 2001 | Lucas et al. NAR Feb 15; 29(4):960-9 |
| I-SobII | Sob2593c | Scenedesmus | obliquus | 167 | D | L43360 | | | 2001 | Lucas et al. NAR Feb 15; 29(4):960-9 |
| I-TmuI | Tmu2593c | Trichosarcina | mucosa | 168 | D | AAG61152 | AY008341 | | 2001 | Lucas et al. NAR Feb 15; 29(4):960-9 |
| PI-AaeI | ORF168 | Aquifex | aeolicus | 347 | D | | | AE000657 | 1998 | Deckert, G. et al. Nature 392 (6674), 353-358 |
| PI-ApeI | Ape hyp3 | Aeropyrum | pernix | 468 | DD | B72665 | | | 1999 | Kawarabayasi, Y. et al DNA Res. 6(2), 83-101 |
| PI-BspI | Bsp RIR1 | Bacteriophage | prophage A | 385 | DD | | | | 2001 | http://bioinformatics.weizmann.ac.il/~pietro/inteins |
| PI-CeuI | Ceu clpP | Chlamydomonas | eugametos | 457 | DD | | | | 2001 | http://bioinformatics.weizmann.ac.il/~pietro/inteins |
| PI-CirI | CIV RIR1 | Virus | | 339 | DD | | | | 2001 | http://bioinformatics.weizmann.ac.il/~pietro/inteins |
| PI-CtrI | PI-VDEII, Ctr VMA, PI-SceII | Candida | tropicalis | 471 | DD | M64984 | | NC_003038 | 1993 | Gu, et al. J Biol Chem 268:7272-81 |
| PI-DraI | Dra RIR1 | Deinococcus | radiodurans | 367 | DD | | | | 2001 | http://bioinformatics.weizmann.ac.il/~pietro/inteins |
| PI-DraII | Dra snf2 | Deinococcus | radiodurans | 343 | DD | | | | 2001 | http://bioinformatics.weizmann.ac.il/~pietro/inteins |
| PI-MavI | Mav dnaB | Mycobacterium | avium | 337 | DD | | | | 2001 | http://bioinformatics.weizmann.ac.il/~pietro/inteins |
| PI-MchI | Mch recA | Mycobacterium | chitae | 365 | DD | | | | 2001 | http://bioinformatics.weizmann.ac.il/~pietro/inteins |
| PI-MfaI | Mfa recA | Mycobacterium | fallax | 364 | DD | | | | 2001 | http://bioinformatics.weizmann.ac.il/~pietro/inteins |
| PI-MfII | Mfl gyrA | Mycobacterium | flavescens | 421 | DD | | | | 2001 | http://bioinformatics.weizmann.ac.il/~pietro/inteins |
| PI-MfIII | Mfl recA | Mycobacterium | flavescens | 364 | DD | | | | 2001 | http://bioinformatics.weizmann.ac.il/~pietro/inteins |
| PI-MfIII 144 | Mfl recA 14474 | Mycobacterium | flavescens | 365 | DD | | | | 2001 | http://bioinformatics.weizmann.ac.il/~pietro/inteins |
| PI-MgaI | Mga gyrA | Mycobacterium | gastri | 420 | DD | | | | 2001 | http://bioinformatics.weizmann.ac.il/~pietro/inteins |
| PI-MgaII | Mga ppsI | Mycobacterium | gastri | 378 | DD | | | | 2001 | http://bioinformatics.weizmann.ac.il/~pietro/inteins |
| PI-MgaIII | Mga recA | Mycobacterium | gastri | 369 | DD | | | | 2001 | http://bioinformatics.weizmann.ac.il/~pietro/inteins |
| PI-MgoI | Mgo gyrA | Mycobacterium | gordonae | 420 | DD | | | | 2001 | http://bioinformatics.weizmann.ac.il/~pietro/inteins |
| PI-MinI | Min dnaB | Mycobacterium | intracellulare | 335 | DD | | | | 2001 | http://bioinformatics.weizmann.ac.il/~pietro/inteins |
| PI-MjaI | Mja GF6P | Methanococcus | jannaschii | 500 | DD | | | | 2001 | http://bioinformatics.weizmann.ac.il/~pietro/inteins |
| PI-MjaII | Mja helicase | Methanococcus | jannaschii | 502 | DD | | | | 2001 | http://bioinformatics.weizmann.ac.il/~pietro/inteins |
| PI-MjaIII | Mja hyp1 | Methanococcus | jannaschii | 393 | DD | | | | 2001 | http://bioinformatics.weizmann.ac.il/~pietro/inteins |
| PI-MjaIV | MjaIF2 | Methanococcus | jannaschii | 547 | DD | | | | 2001 | http://bioinformatics.weizmann.ac.il/~pietro/inteins |
| PI-MjaIX | Mja r-gyr | Methanococcus | jannaschii | 494 | DD | | | | 2001 | http://bioinformatics.weizmann.ac.il/~pietro/inteins |
| PI-Mja VI | Mja PEPSyn | Methanococcus | jannaschii | 413 | DD | | | | 2001 | http://bioinformatics.weizmann.ac.il/~pietro/inteins |
| PI-Mja VII | Mja pol-1 | Methanococcus | jannaschii | 365 | DD | | | | 2001 | http://bioinformatics.weizmann.ac.il/~pietro/inteins |
| PI-Mja VIII | Mja pol-2 | Methanococcus | jannaschii | 476 | DD | | | | 2001 | http://bioinformatics.weizmann.ac.il/~pietro/inteins |
| PI-Mja X | Mja RFC-1 | Methanococcus | jannaschii | 549 | DD | | | | 2001 | http://bioinformatics.weizmann.ac.il/~pietro/inteins |
| PI-Mja XI | Mja RFC-2 | Methanococcus | jannaschii | 437 | DD | | | | 2001 | http://bioinformatics.weizmann.ac.il/~pietro/inteins |
| PI-Mja XII | Mja RFC-3 | Methanococcus | jannaschii | 544 | DD | | | | 2001 | http://bioinformatics.weizmann.ac.il/~pietro/inteins |
| PI-Mja XIII | Mja RNR-1 | Methanococcus | jannaschii | 454 | DD | | | | 2001 | http://bioinformatics.weizmann.ac.il/~pietro/inteins |
| PI-Mja XIV | Mja RNR-2 | Methanococcus | jannaschii | 534 | DD | | | | 2001 | http://bioinformatics.weizmann.ac.il/~pietro/inteins |

| Protein | Synonym | Organism | Species | Size (kD) | Motif | Acces N° (mega) | Access N° (gene) | Acces N° (genome) | Year | Reference |
|---|---|---|---|---|---|---|---|---|---|---|
| PI-MjaXIX | Mja UDPGD | Methanococcus | jannaschii | 455 | DD | | | | 2001 | http://bioinformatics.weizmann.ac.il/~pietro/inteins |
| PI-MjaXV | Mja RpolA* | Methanococcus | jannaschii | 472 | DD | | | | 2001 | http://bioinformatics.weizmann.ac.il/~pietro/inteins |
| PI-MjaXVI | Mja RpolA* | Methanococcus | jannaschii | 453 | DD | | | | 2001 | http://bioinformatics.weizmann.ac.il/~pietro/inteins |
| PI-MjaXVII | Mja rtcB4 | Methanococcus | jannaschii | 489 | DD | | | | 2001 | http://bioinformatics.weizmann.ac.il/~pietro/inteins |
| PI-MjaXVIII | Mja TFIIB | Methanococcus | jannaschii | 336 | DD | | | | 2001 | http://bioinformatics.weizmann.ac.il/~pietro/inteins |
| PI-MkaI | Mka gyrA | Mycobacterium | kansasii | 420 | DD | | | | 2001 | http://bioinformatics.weizmann.ac.il/~pietro/inteins |
| PI-MleI | Mle recA | Mycobacterium | leprae | 365 (366) | DD | X73822 | | | 1994 | Davis et al. EMBO J. Feb 1; 13(3):699-703. |
| PI-MleIII | Mle gyrA | Mycobacterium | leprae | 420 | DD | | | | 2001 | http://bioinformatics.weizmann.ac.il/~pietro/inteins |
| PI-MleIV | Mle pps1 | Mycobacterium | leprae | 387 | DD | | | | 2001 | http://bioinformatics.weizmann.ac.il/~pietro/inteins |
| PI-MmaI | Mma gyrA | Mycobacterium | malmoense | 420 | DD | | | | 2001 | http://bioinformatics.weizmann.ac.il/~pietro/inteins |
| PI-MshI | Msh I | Mycobacterium | shimoidei | 365 | DD | | | | 2001 | http://bioinformatics.weizmann.ac.il/~pietro/inteins |
| PI-MsmII | Msm dnaB-2 | Mycobacterium | smegmatis | 426 | DD | | | | 2001 | http://bioinformatics.weizmann.ac.il/~pietro/inteins |
| PI-MthI | Mth recA | Mycobacterium | thermoresistibile | 366 | DD | | | | 2001 | http://bioinformatics.weizmann.ac.il/~pietro/inteins |
| PI-MtuHI | PI-MtuHIP, Mtu dnaB | Mycobacterium | tuberculosis | 415 | DD | | | | 2000 | http://bioinformatics.weizmann.ac.il/~pietro/inteins |
| PI-MtuHIII | PI-MtuHIIIP, Mtu pps1 | Mycobacterium | tuberculosis | 360 | DD | | | | 2001 | http://bioinformatics.weizmann.ac.il/~pietro/inteins |
| PI-MtuI | Mtu recA | Mycobacterium | tuberculosis | 439 (441) | DD | X58485 | | | 1992 | Davis et al. Cell Oct 16; 71(2):201-10 |
| PI-PabIII | Pab RIRI-1 | Pyrococcus | abyssi | 399 | DD | | | | 2001 | http://bioinformatics.weizmann.ac.il/~pietro/inteins |
| PI-PabIX | Pab RFC-2 | Pyrococcus | abyssi | 608 | DD | | | | 2001 | http://bioinformatics.weizmann.ac.il/~pietro/inteins |
| PI-PabIon | PabIon | Pyrococcus | abyssi | 333 | DD | | | | 2001 | http://bioinformatics.weizmann.ac.il/~pietro/inteins |
| PI-PabV | Pab moaA | Pyrococcus | abyssi | 437 | DD | | | | 2001 | http://bioinformatics.weizmann.ac.il/~pietro/inteins |
| PI-PabIF2 | PabIF2 | Pyrococcus | abyssi | 394 | DD | | | | 2001 | http://bioinformatics.weizmann.ac.il/~pietro/inteins |
| PI-PabVIII | Pab RFC-1 | Pyrococcus | abyssi | 499 | DD | | | | 2001 | http://bioinformatics.weizmann.ac.il/~pietro/inteins |
| PI-PabXI | Pab RIR1-2 | Pyrococcus | abyssi | 438 | DD | | | | 2001 | http://bioinformatics.weizmann.ac.il/~pietro/inteins |
| PI-PabXII | Pab RIR1-3 | Pyrococcus | abyssi | 382 | DD | | | | 2001 | http://bioinformatics.weizmann.ac.il/~pietro/inteins |
| PI-PabXIII | Pab rtcB4 | Pyrococcus | abyssi | 437 | DD | | | | 2001 | http://bioinformatics.weizmann.ac.il/~pietro/inteins |
| PI-PabXIV | Pab VMA | Pyrococcus | abyssi | 429 | DD | | | | 2001 | http://bioinformatics.weizmann.ac.il/~pietro/inteins |
| PI-PfuI | Pfu klbA | Pyrococcus | furiosus | 522 (525) | DD | | | | 1999 | Komori, et al. NAR 27:4167-74 |
| PI-PfuII | Pfu RIR1-2 | Pyrococcus | furiosus | 383 | DD | | | | 1999 | Komori, et al. NAR 27:4167-74 |
| PI-PfuIII | Pfu RtcB, Pfu rtcB4 Pfu Hyp-2) | Pyrococcus | furiosus | 481 | DD | | | | | |
| PI-PfuIV | Pfu RIR1-1 | Pyrococcus | furiosus | 455 | DD | | | | | |
| PI-PfuIX | Pfu RFC | Pyrococcus | furiosus | 525 | DD | | | | | |
| PI-PfuV | Pfu IF2 | Pyrococcus | furiosus | 387 | DD | | | | | |
| PI-PfuVI | PfuIon | Pyrococcus | furiosus | 401 | DD | | | | | |
| PI-PfuVII | Pfu CDC21 | Pyrococcus | furiosus | 367 | DD | | | | | |
| PI-PfuVIII | Pfu VMA | Pyrococcus | furiosus | 424 | DD | | | | | |
| PI-PfuX | Pfu topA | Pyrococcus | furiosus | 373 | DD | | | | | |
| PI-PhoI | Pho VMA | Pyrococcus | horikoshii | 377 | DD | | | | | |
| PI-PhoIII | Pho pol | Pyrococcus | horikoshii | 460 | DD | | | | 2001 | http://bioinformatics.weizmann.ac.il/~pietro/inteins |
| PI-PhoIX | Pho RIR1 | Pyrococcus | horikoshii | 385 | DD | | | | | |
| PI-PhoV | Pho 1F2 | Pyrococcus | horikoshii | 445 | DD | | | | | |
| PI-PhoVI | Pho klbA | Pyrococcus | horikoshii | 521 | DD | | | | | |
| PI-PhoVII | Pho LHR | Pyrococcus | horikoshii | 476 | DD | | | | | |
| PI-PhoVIII | Pho RFC | Pyrococcus | horikoshii | 526 | DD | | | | | |
| PI-PhoX | Pho r-gyr | Pyrococcus | horikoshii | 410 | DD | | | | | |

-continued

| Protein | Synonym | Organism | Species | Size (kD) | Motif | Acces N° (mega) | Access N° (gene) | Acces N° (genome) | Year | Reference |
|---|---|---|---|---|---|---|---|---|---|---|
| PI-Pho XIII | PhoIon | Pyrococcus | horikoshii | 475 | DD | | | | 1997 | Takagi et al. Appl. Environ. Microbiol. 63:4504-10 |
| PI-Pho XIV | Pho RtcB, rtcB4 (Pho Hyp-2) | Pyrococcus | horikoshii | 390 | DD | | | | 1997 | Takagi et al. Appl. Environ. Microbiol. 63:4504-10 |
| PI-PkoI | Psp-KOD Pol-1 Pko pol-1 | Pyrococcus | kodakaraensis | 360 | DD | | | | | |
| PI-PkoII | Pko Pol-2 (PSP-KOD Pol-2) | Pyrococcus | kodakaraensis | 537 | DD | | | | | |
| PI-PkoIII | Psp pol-3 | Pyrococcus | kodakaraensis | 537 | DD | | | | 1993 | Xu, et al. Cell 75:1371-77 |
| PI-PspI | PSP-GBD Pol, Psp pol-1 | Pyrococcus | species | 537 | DD | | | | | |
| PI-RmaI | PI-Rma43812IP, Rma dnaB | Rhodothermus | marinus | 428 | DD | | | | 1997 | Liu, et al. PNAS 94:7851-56 |
| PI-SceI | PI-VDEI | Saccharomyces | cerevisiae | 454 | DD | M21609 | | | 1990 | Hirata, R. et al. J Biol Chem 265:6726-6733 |
| PI-SPβI | PI-SPBetaIP | Bacteriophage | SPβ | 385 | DD | | | | 1998 | Lazarevic, et al. PNAS 95:1692-97 |
| PI-SPβII | | Bacteriophage | SPβ | 385 | DD | | | | | |
| PI-SspI | Spb RIR1 | Synechocystis | species | 429 | DD | | | | 2001 | http://bioinformatics.weizmann.ac.il/~pietro/inteins |
| PI-TagI | Ssp dnaB | Thermococcus (Pyrococcus) | aggregans | 360 | DD | | | BA000022 | 2001 | http://bioinformatics.weizmann.ac.il/~pietro/inteins |
| PI-TagII | | Thermococcus (Pyrococcus) | aggregans | 538 | DD | | | | 2001 | http://bioinformatics.weizmann.ac.il/~pietro/inteins |
| PI-TfuI | Tfu pol-1 | Thermococcus (Pyrococcus) | fumicolans | 360 | DD | Z69882 | | | 2000 | Saves, et al. JBC 275:2335-41 |
| PI-TfuII | Tfu pol-2 | Thermococcus (Pyrococcus) | fumicolans | 389 | DD | Z69882 | | | 2000 | Saves, et al. JBC 275:2335-41 |
| PI-ThyI | Thy pol-1 | Thermococcus (Pyrococcus) | hydrothermalis | 538 | DD | | | | | |
| PI-ThyII | Thy pol-2 | Thermococcus (Pyrococcus) | hydrothermalis | 390 | DD | | | | 2001 | http://bioinformatics.weizmann.ac.il/~pietro/inteins |
| PI-TliI | Tli pol-2, pl-TliR | Thermococcus (Pyrococcus) | litoralis | 390 | DD | M74198 | | | 1992 | Perler et al. PNAS 89:5577-5581 |
| PI-TliII | Tli pol-1 | Thermococcus (Pyrococcus) | litoralis | 541 | DD | M74198 | | | 1993 | Lambowitz, et al. Annu Rev Biochem 62:587-622 |
| PI-TspI | Tsp-TY Pol-1 | Thermococcus (Pyrococcus) | species | | DD | | | | | |
| PI-TspII | Tsp-TY Pol-2 | Thermococcus (Pyrococcus) | species | 536 | DD | | | | 2001 | http://bioinformatics.weizmann.ac.il/~pietro/inteins |
| PI-TspIII | Tsp-TY Pol-3 | Thermococcus (Pyrococcus) | species | 390 | DD | | | | 2001 | http://bioinformatics.weizmann.ac.il/~pietro/inteins |
| PI-TspIV | TspGE8 pol-1 | Thermococcus (Pyrococcus) | species | 536 | DD | | | | | |
| PI-Tsp V | TspGE8 pol-2 | Thermococcus (Pyrococcus) | species | 390 | DD | | | | | |

What is claimed:

1. An isolated hybrid meganuclease comprising two domains,
   wherein the N-terminal domain is derived from the first domain of the I-DmoI LAGLIDADG endonuclease and the C-terminal domain is derived from the I-Cre I LAGLIDADG endonuclease,
   wherein each of said N-terminal and C-terminal domain comprises a αββαββα fold, wherein the two ββ hairpins connected by an α helix (second helix) that are folded in a four-stranded antiparallel beta-sheet and the downstream α helix (third helix) form the DNA binding moiety of said domain, and wherein the first α helix comprises a dodecapeptide motif,
   wherein the αββαββα fold of the N-terminal domain corresponds to the amino acid sequence from positions 8 to 92 of the I-DmoI sequence SEQ ID NO: 18 and comprises the dodecapeptide motif SEQ ID NO: 20 (LLGLIIGDG),
   wherein the αββαββα fold of the C-terminal domain corresponds to the amino acid sequence from anyone of position 8 to 13 to position 94 of the I-CreI sequence SEQ ID NO: 19 and comprises the dodecapeptide motif SEQ ID NO: 21 (LAGFVDGDG),
   wherein said N-terminal and C-terminal domains are joined by a polypeptide linker, and
   wherein said hybrid meganuclease comprises an amino acid sequence which is at least 80% identical to SEQ ID NO: 2, and has endonuclease activity.

2. The hybrid meganuclease according to claim 1, wherein the αββαββα fold of the C-terminal domain corresponds to the amino acid sequence from positions 105 to 109 of the I-DmoI sequence SEQ ID NO: 18 fused at its C-terminal residue directly to the N-terminal residue of the sequence from positions 13 to 94 of the I-CreI sequence SEQ ID NO: 19.

3. The hybrid meganuclease according to claim 1, which comprises a N-terminal domain comprising the sequence from positions 8 to 92 of the I-DmoI sequence SEQ ID NO: 18, joined by a polypeptide linker to a C-terminal domain comprising the sequence from positions 105 to 109 of the I-DmoI sequence SEQ ID NO: 18 fused at its C-terminal residue directly to the N-terminal residue of the sequence from positions 13 to 94 of the I-CreI sequence SEQ ID NO: 19.

4. The hybrid meganuclease according to claim 1, which comprises a N-terminal domain comprising the sequence from positions 8 to 92 of the I-DmoI sequence SEQ ID NO: 18, joined by a polypeptide linker to a C-terminal domain comprising the sequence from positions 8 to 94 of the I-CreI sequence SEQ ID NO: 19.

5. The hybrid meganuclease according to claim 1, wherein said polypeptide linker comprises the sequence from positions 96 to 103 of the I-DmoI sequence SEQ ID NO: 18.

6. The hybrid meganuclease according to claim 1, wherein said polypeptide linker comprises the sequence from positions 93 to 104 of the I-DmoI sequence SEQ ID NO: 18.

7. The hybrid meganuclease according to claim 1, which comprises the sequence from positions 1 to 109 of the I-DmoI sequence SEQ ID NO: 18 fused at its C-terminal residue directly to the N-terminal residue of the sequence from positions 13 to 163 of the I-CreI sequence SEQ ID NO: 19.

8. The hybrid meganuclease according to claim 1, which comprises an amino acid sequence that is at least 90% identical to SEQ ID NO: 2.

9. The hybrid meganuclease according to claim 1, which comprises an amino acid sequence that is at least 95% identical to SEQ ID NO: 2.

10. The hybrid meganuclease according to claim 1, which comprises an amino acid sequence that is at least 99% identical to SEQ ID NO: 2.

11. The hybrid meganuclease according to claim 1, which comprises at least one mutation in SEQ ID NO: 2 that avoids the steric hindrance between amino acid side chains and/or increases the stability of the hybrid meganuclease.

12. The hybrid meganuclease of claim 1, which comprises the substitution of at least one amino acid residue in the sequence SEQ ID NO: 2 that is selected from the group consisting of: L48, H52, L56 and I108.

13. The hybrid meganuclease of claim 1, which comprises at least one amino acid substitution in the sequence SEQ ID NO: 2 that is selected from the group consisting of: L48A, H52A, L56D and I108L.

14. The hybrid meganuclease of claim 1, which comprises the amino acid sequence of SEQ ID NO: 4.

15. The hybrid meganuclease of claim 1, which comprises the amino acid sequence of SEQ ID NO: 2.

\* \* \* \* \*

SEQUENCE LISTING

<160> NUMBER OF SEQ ID NOS: 21

<210> SEQ ID NO 1
<211> LENGTH: 795
<212> TYPE: DNA
<213> ORGANISM: Artificial sequence
<220> FEATURE:
<223> OTHER INFORMATION: Description of artificial sequence: I-Dmo I-I-Cre I
<220> FEATURE:
<221> NAME/KEY: CDS
<222> LOCATION: (1)..(792)
<223> OTHER INFORMATION: I-Dmo I-I-Cre I

<400> SEQUENCE: 1

```
atg gcc cat aac aat gag aac gtt tct ggt atc tcc gct tac ctg ctg       48
Met Ala His Asn Asn Glu Asn Val Ser Gly Ile Ser Ala Tyr Leu Leu
1               5                   10                  15 ggc ctg att atc ggt gat ggt ggc ctg tac aag ctg aaa tat aaa ggt       96
Gly Leu Ile Ile Gly Asp Gly Gly Leu Tyr Lys Leu Lys Tyr Lys Gly
                20                  25                  30 aac cgt agc gaa tat cgt gtt gtg atc acc cag aag tct gaa aac ctg      144
Asn Arg Ser Glu Tyr Arg Val Val Ile Thr Gln Lys Ser Glu Asn Leu
            35                  40                  45 att aaa caa cac atc gca ccg ctg atg cag ttt ctg att gat gaa ctg      192
Ile Lys Gln His Ile Ala Pro Leu Met Gln Phe Leu Ile Asp Glu Leu
        50                  55                  60 aat gtg aaa tct aaa atc cag atc gtt aag ggt gat acc cgc tat gag      240
Asn Val Lys Ser Lys Ile Gln Ile Val Lys Gly Asp Thr Arg Tyr Glu
65                  70                  75                  80 ctg cgt gtg agc tct aag aaa ctg tac tat tac ttc gct aac atg ctg      288
Leu Arg Val Ser Ser Lys Lys Leu Tyr Tyr Tyr Phe Ala Asn Met Leu
                85                  90                  95 gag cgt atc cgc ctg ttc aac atg cgt gag cag ctg gcg ttc ctg gcc      336
Glu Arg Ile Arg Leu Phe Asn Met Arg Glu Gln Leu Ala Phe Leu Ala
                100                 105                 110 ggc ttt gtg gac ggt gac ggt agc atc atc gct cag att aaa cca aac      384
Gly Phe Val Asp Gly Asp Gly Ser Ile Ile Ala Gln Ile Lys Pro Asn
            115                 120                 125 cag tct tat aaa ttc aag cat cag ctg tcc ctg acc ttt cag gtg act      432
Gln Ser Tyr Lys Phe Lys His Gln Leu Ser Leu Thr Phe Gln Val Thr
        130                 135                 140 caa aag acc cag cgc cgt tgg ttt ctg gac aaa ctg gtg gat gaa att      480
Gln Lys Thr Gln Arg Arg Trp Phe Leu Asp Lys Leu Val Asp Glu Ile
145                 150                 155                 160 ggc gtt ggt tac gta cgt gat cgc ggt agc gtt tcc gat tac att ctg      528
Gly Val Gly Tyr Val Arg Asp Arg Gly Ser Val Ser Asp Tyr Ile Leu
                165                 170                 175 agc gaa atc aag ccg ctg cac aac ttc ctg act caa ctg caa ccg ttt      576
Ser Glu Ile Lys Pro Leu His Asn Phe Leu Thr Gln Leu Gln Pro Phe
                180                 185                 190 ctg aaa ctg aaa cag aaa cag gca aac ctg gtt ctg aaa att atc gaa      624
Leu Lys Leu Lys Gln Lys Gln Ala Asn Leu Val Leu Lys Ile Ile Glu
            195                 200                 205 cag ctg ccg tct gca aaa gaa tcc ccg gac aaa ttc ctg gaa gtt tgt      672
Gln Leu Pro Ser Ala Lys Glu Ser Pro Asp Lys Phe Leu Glu Val Cys
        210                 215                 220 acc tgg gtg gat cag att gca gct ctg aac gat tct aag acg cgt aaa      720
Thr Trp Val Asp Gln Ile Ala Ala Leu Asn Asp Ser Lys Thr Arg Lys
225                 230                 235                 240 acc act tct gaa acc gtt cgt gct gtg ctg gac agc ctg agc gag aag      768
Thr Thr Ser Glu Thr Val Arg Ala Val Leu Asp Ser Leu Ser Glu Lys
```

```
Thr Thr Ser Glu Thr Val Arg Ala Val Leu Asp Ser Leu Ser Glu Lys
                245                 250                 255 aag aaa tcc tcc ccg gcg gcc gac tag                               795
Lys Lys Ser Ser Pro Ala Ala Asp
            260

<210> SEQ ID NO 2
<211> LENGTH: 264
<212> TYPE: PRT
<213> ORGANISM: Artificial sequence
<220> FEATURE:
<223> OTHER INFORMATION: Description of artificial sequence: I-Dmo
      I-I-Cre I

<400> SEQUENCE: 2

Met Ala His Asn Asn Glu Asn Val Ser Gly Ile Ser Ala Tyr Leu Leu
1               5                   10                  15

Gly Leu Ile Ile Gly Asp Gly Gly Leu Tyr Lys Leu Lys Tyr Lys Gly
            20                  25                  30

Asn Arg Ser Glu Tyr Arg Val Val Ile Thr Gln Lys Ser Glu Asn Leu
        35                  40                  45

Ile Lys Gln His Ile Ala Pro Leu Met Gln Phe Leu Ile Asp Glu Leu
    50                  55                  60

Asn Val Lys Ser Lys Ile Gln Ile Val Lys Gly Asp Thr Arg Tyr Glu
65                  70                  75                  80

Leu Arg Val Ser Ser Lys Lys Leu Tyr Tyr Tyr Phe Ala Asn Met Leu
                85                  90                  95

Glu Arg Ile Arg Leu Phe Asn Met Arg Glu Gln Leu Ala Phe Leu Ala
            100                 105                 110

Gly Phe Val Asp Gly Asp Gly Ser Ile Ile Ala Gln Ile Lys Pro Asn
        115                 120                 125

Gln Ser Tyr Lys Phe Lys His Gln Leu Ser Leu Thr Phe Gln Val Thr
    130                 135                 140

Gln Lys Thr Gln Arg Arg Trp Phe Leu Asp Lys Leu Val Asp Glu Ile
145                 150                 155                 160

Gly Val Gly Tyr Val Arg Asp Arg Gly Ser Val Ser Asp Tyr Ile Leu
                165                 170                 175

Ser Glu Ile Lys Pro Leu His Asn Phe Leu Thr Gln Leu Gln Pro Phe
            180                 185                 190

Leu Lys Leu Lys Gln Lys Gln Ala Asn Leu Val Leu Lys Ile Ile Glu
        195                 200                 205

Gln Leu Pro Ser Ala Lys Glu Ser Pro Asp Lys Phe Leu Glu Val Cys
    210                 215                 220

Thr Trp Val Asp Gln Ile Ala Ala Leu Asn Asp Ser Lys Thr Arg Lys
225                 230                 235                 240

Thr Thr Ser Glu Thr Val Arg Ala Val Leu Asp Ser Leu Ser Glu Lys
                245                 250                 255

Lys Lys Ser Ser Pro Ala Ala Asp
            260

<210> SEQ ID NO 3
<211> LENGTH: 795
<212> TYPE: DNA
<213> ORGANISM: Artificial sequence
<220> FEATURE:
<223> OTHER INFORMATION: Description of artificial sequence: Fig 6B
      hybrid
<220> FEATURE:
<221> NAME/KEY: CDS
<222> LOCATION: (1)..(792)
```

<223> OTHER INFORMATION: FIg 6B hybrid

<400> SEQUENCE: 3

| | | | | | | | | | | | | | | | | |
|---|---|---|---|---|---|---|---|---|---|---|---|---|---|---|---|---|
| atg | gcc | cac | aac | aat | gag | aat | gtg | tct | ggc | atc | tct | gcc | tac | ctg | ctg | 48 |
| Met | Ala | His | Asn | Asn | Glu | Asn | Val | Ser | Gly | Ile | Ser | Ala | Tyr | Leu | Leu | |
| 1 | | | | 5 | | | | | 10 | | | | | 15 | | |

| ggc | ctc | atc | att | gga | gat | gga | ggt | ctg | tac | aaa | ctt | aag | tac | aaa | ggc | 96 |
|---|---|---|---|---|---|---|---|---|---|---|---|---|---|---|---|---|
| Gly | Leu | Ile | Ile | Gly | Asp | Gly | Gly | Leu | Tyr | Lys | Leu | Lys | Tyr | Lys | Gly | |
| | | | 20 | | | | | 25 | | | | | 30 | | | |

| aac | agg | tct | gag | tac | aga | gtg | gtc | atc | acc | cag | aag | tct | gaa | aat | gct | 144 |
|---|---|---|---|---|---|---|---|---|---|---|---|---|---|---|---|---|
| Asn | Arg | Ser | Glu | Tyr | Arg | Val | Val | Ile | Thr | Gln | Lys | Ser | Glu | Asn | Ala | |
| | | 35 | | | | | 40 | | | | | 45 | | | | |

| atc | aag | caa | gct | att | gct | cca | gat | atg | cag | ttc | ctg | att | gat | gaa | ctc | 192 |
|---|---|---|---|---|---|---|---|---|---|---|---|---|---|---|---|---|
| Ile | Lys | Gln | Ala | Ile | Ala | Pro | Asp | Met | Gln | Phe | Leu | Ile | Asp | Glu | Leu | |
| 50 | | | | | 55 | | | | | 60 | | | | | | |

| aat | gtc | aag | agc | aag | atc | cag | att | gtc | aaa | ggt | gac | act | aga | tat | gag | 240 |
|---|---|---|---|---|---|---|---|---|---|---|---|---|---|---|---|---|
| Asn | Val | Lys | Ser | Lys | Ile | Gln | Ile | Val | Lys | Gly | Asp | Thr | Arg | Tyr | Glu | |
| 65 | | | | 70 | | | | | 75 | | | | | 80 | | |

| ctg | aga | gtt | tcc | tcc | aag | aaa | ctt | tac | tat | tac | ttt | gcc | aac | atg | ttg | 288 |
|---|---|---|---|---|---|---|---|---|---|---|---|---|---|---|---|---|
| Leu | Arg | Val | Ser | Ser | Lys | Lys | Leu | Tyr | Tyr | Tyr | Phe | Ala | Asn | Met | Leu | |
| | | | | 85 | | | | | 90 | | | | | 95 | | |

| gag | agg | atc | agg | ctg | ttc | aat | atg | agg | gag | caa | ctg | gcc | ttc | ctt | gct | 336 |
|---|---|---|---|---|---|---|---|---|---|---|---|---|---|---|---|---|
| Glu | Arg | Ile | Arg | Leu | Phe | Asn | Met | Arg | Glu | Gln | Leu | Ala | Phe | Leu | Ala | |
| | | | 100 | | | | | 105 | | | | | 110 | | | |

| gga | ttt | gtg | gat | ggt | gat | ggc | tcc | atc | att | gct | cag | ata | aaa | cca | aat | 384 |
|---|---|---|---|---|---|---|---|---|---|---|---|---|---|---|---|---|
| Gly | Phe | Val | Asp | Gly | Asp | Gly | Ser | Ile | Ile | Ala | Gln | Ile | Lys | Pro | Asn | |
| | | 115 | | | | | 120 | | | | | 125 | | | | |

| caa | tct | tac | aag | ttc | aaa | cac | cag | ctc | tcc | ttg | acc | ttt | caa | gtc | act | 432 |
|---|---|---|---|---|---|---|---|---|---|---|---|---|---|---|---|---|
| Gln | Ser | Tyr | Lys | Phe | Lys | His | Gln | Leu | Ser | Leu | Thr | Phe | Gln | Val | Thr | |
| | 130 | | | | | 135 | | | | | 140 | | | | | |

| cag | aag | aca | caa | aga | agg | tgg | ttc | ttg | gac | aaa | ttg | gtt | gat | gag | att | 480 |
|---|---|---|---|---|---|---|---|---|---|---|---|---|---|---|---|---|
| Gln | Lys | Thr | Gln | Arg | Arg | Trp | Phe | Leu | Asp | Lys | Leu | Val | Asp | Glu | Ile | |
| 145 | | | | | 150 | | | | | 155 | | | | | 160 | |

| ggt | gtg | ggc | tat | gtc | aga | gac | aga | ggc | tct | gtg | tca | gac | tac | atc | ctg | 528 |
|---|---|---|---|---|---|---|---|---|---|---|---|---|---|---|---|---|
| Gly | Val | Gly | Tyr | Val | Arg | Asp | Arg | Gly | Ser | Val | Ser | Asp | Tyr | Ile | Leu | |
| | | | | 165 | | | | | 170 | | | | | 175 | | |

| tct | gaa | att | aag | cct | ctt | cat | aac | ttt | ctc | acc | caa | ctg | caa | ccc | ttc | 576 |
|---|---|---|---|---|---|---|---|---|---|---|---|---|---|---|---|---|
| Ser | Glu | Ile | Lys | Pro | Leu | His | Asn | Phe | Leu | Thr | Gln | Leu | Gln | Pro | Phe | |
| | | | 180 | | | | | 185 | | | | | 190 | | | |

| ttg | aag | ctc | aaa | cag | aag | caa | gca | aat | ctg | gtt | ttg | aaa | atc | att | gaa | 624 |
|---|---|---|---|---|---|---|---|---|---|---|---|---|---|---|---|---|
| Leu | Lys | Leu | Lys | Gln | Lys | Gln | Ala | Asn | Leu | Val | Leu | Lys | Ile | Ile | Glu | |
| | | | | 195 | | | | | 200 | | | | | 205 | | |

| cag | ctg | cca | tct | gcc | aag | gag | tcc | cct | gac | aag | ttt | ctt | gaa | gtg | tgt | 672 |
|---|---|---|---|---|---|---|---|---|---|---|---|---|---|---|---|---|
| Gln | Leu | Pro | Ser | Ala | Lys | Glu | Ser | Pro | Asp | Lys | Phe | Leu | Glu | Val | Cys | |
| 210 | | | | | 215 | | | | | 220 | | | | | | |

| act | tgg | gtg | gat | cag | att | gct | gcc | ttg | aat | gac | tcc | aag | acc | aga | aaa | 720 |
|---|---|---|---|---|---|---|---|---|---|---|---|---|---|---|---|---|
| Thr | Trp | Val | Asp | Gln | Ile | Ala | Ala | Leu | Asn | Asp | Ser | Lys | Thr | Arg | Lys | |
| 225 | | | | 230 | | | | | 235 | | | | | 240 | | |

| acc | acc | tct | gag | act | gtg | agg | gca | gtt | ctg | gat | agc | ctc | tct | gag | aag | 768 |
|---|---|---|---|---|---|---|---|---|---|---|---|---|---|---|---|---|
| Thr | Thr | Ser | Glu | Thr | Val | Arg | Ala | Val | Leu | Asp | Ser | Leu | Ser | Glu | Lys | |
| | | | 245 | | | | | 250 | | | | | 255 | | | |

| aaa | aag | tcc | tct | cct | gcg | gcc | gac | tag | | | | | | | | 795 |
|---|---|---|---|---|---|---|---|---|---|---|---|---|---|---|---|---|
| Lys | Lys | Ser | Ser | Pro | Ala | Ala | Asp | | | | | | | | | |
| | | | 260 | | | | | | | | | | | | | |

<210> SEQ ID NO 4
<211> LENGTH: 264
<212> TYPE: PRT
<213> ORGANISM: Artificial sequence
<220> FEATURE:
<223> OTHER INFORMATION: Description of artificial sequence: Fig 6B hybrid

```
<400> SEQUENCE: 4

Met Ala His Asn Asn Glu Asn Val Ser Gly Ile Ser Ala Tyr Leu Leu
1               5                   10                  15

Gly Leu Ile Ile Gly Asp Gly Gly Leu Tyr Lys Leu Tyr Lys Gly
            20                  25                  30

Asn Arg Ser Glu Tyr Arg Val Val Ile Thr Gln Lys Ser Glu Asn Ala
            35                  40                  45

Ile Lys Gln Ala Ile Ala Pro Asp Met Gln Phe Leu Ile Asp Glu Leu
50                  55                  60

Asn Val Lys Ser Lys Ile Gln Ile Val Lys Gly Asp Thr Arg Tyr Glu
65                  70                  75                  80

Leu Arg Val Ser Ser Lys Lys Leu Tyr Tyr Tyr Phe Ala Asn Met Leu
                85                  90                  95

Glu Arg Ile Arg Leu Phe Asn Met Arg Glu Gln Leu Ala Phe Leu Ala
            100                 105                 110

Gly Phe Val Asp Gly Asp Gly Ser Ile Ile Ala Gln Ile Lys Pro Asn
            115                 120                 125

Gln Ser Tyr Lys Phe Lys His Gln Leu Ser Leu Thr Phe Gln Val Thr
130                 135                 140

Gln Lys Thr Gln Arg Arg Trp Phe Leu Asp Lys Leu Val Asp Glu Ile
145                 150                 155                 160

Gly Val Gly Tyr Val Arg Asp Arg Gly Ser Val Ser Asp Tyr Ile Leu
                165                 170                 175

Ser Glu Ile Lys Pro Leu His Asn Phe Leu Thr Gln Leu Gln Pro Phe
            180                 185                 190

Leu Lys Leu Lys Gln Lys Gln Ala Asn Leu Val Leu Lys Ile Ile Glu
            195                 200                 205

Gln Leu Pro Ser Ala Lys Glu Ser Pro Asp Lys Phe Leu Glu Val Cys
210                 215                 220

Thr Trp Val Asp Gln Ile Ala Ala Leu Asn Asp Ser Lys Thr Arg Lys
225                 230                 235                 240

Thr Thr Ser Glu Thr Val Arg Ala Val Leu Asp Ser Leu Ser Glu Lys
                245                 250                 255

Lys Lys Ser Ser Pro Ala Ala Asp
            260

<210> SEQ ID NO 5
<211> LENGTH: 795
<212> TYPE: DNA
<213> ORGANISM: Artificial sequence
<220> FEATURE:
<223> OTHER INFORMATION: Description of artificial sequence: Fig 5
      and 7 sequence
<220> FEATURE:
<221> NAME/KEY: CDS
<222> LOCATION: (1)..(792)
<223> OTHER INFORMATION: Fig 5 and 7 sequence

<400> SEQUENCE: 5 atg gcc aac act aag tac aat aaa gaa ttt ctc ctg tat ctg gca ggt    48
Met Ala Asn Thr Lys Tyr Asn Lys Glu Phe Leu Leu Tyr Leu Ala Gly
1               5                   10                  15 ttc gtc gac ggc gat ggc tcc att atc gca cag atc aag ccg aat cag    96
Phe Val Asp Gly Asp Gly Ser Ile Ile Ala Gln Ile Lys Pro Asn Gln
            20                  25                  30 agc tac aag ttt aaa cac caa ctg tct ctc act ttc cag gtt acc cag   144
Ser Tyr Lys Phe Lys His Gln Leu Ser Leu Thr Phe Gln Val Thr Gln
            35                  40                  45
```

```
aaa act caa cgt cgc tgg ttc ctg gat aag ctg gta gat gag atc ggt      192
Lys Thr Gln Arg Arg Trp Phe Leu Asp Lys Leu Val Asp Glu Ile Gly
 50                  55                  60 gtg ggc tat gta cgc gac cgt ggc tct gtg agc gac tat atc ctg tct      240
Val Gly Tyr Val Arg Asp Arg Gly Ser Val Ser Asp Tyr Ile Leu Ser
 65                  70                  75                  80 gag att aaa cca ctg cat aat ttt ctg acc cag ctg cag gct atg ctg      288
Glu Ile Lys Pro Leu His Asn Phe Leu Thr Gln Leu Gln Ala Met Leu
                 85                  90                  95 gag cgt atc cgt ctg ttc aac atg cgt gag ttc ctg ctg tac ctg gcc      336
Glu Arg Ile Arg Leu Phe Asn Met Arg Glu Phe Leu Leu Tyr Leu Ala
            100                 105                 110 ggc ttt gtg gac ggt gac ggt agc atc atc gct cag att aaa cca aac      384
Gly Phe Val Asp Gly Asp Gly Ser Ile Ile Ala Gln Ile Lys Pro Asn
        115                 120                 125 cag tct tat aaa ttc aag cat cag ctg tcc ctg acc ttt cag gtg act      432
Gln Ser Tyr Lys Phe Lys His Gln Leu Ser Leu Thr Phe Gln Val Thr
    130                 135                 140 caa aag acc cag cgc cgt tgg ttt ctg gac aaa ctg gtg gat gaa att      480
Gln Lys Thr Gln Arg Arg Trp Phe Leu Asp Lys Leu Val Asp Glu Ile
145                 150                 155                 160 ggc gtt ggt tac gta cgt gat cgc ggt agc gtt tcc gat tac att ctg      528
Gly Val Gly Tyr Val Arg Asp Arg Gly Ser Val Ser Asp Tyr Ile Leu
                165                 170                 175 agc gaa atc aag ccg ctg cac aac ttc ctg act caa ctg caa ccg ttt      576
Ser Glu Ile Lys Pro Leu His Asn Phe Leu Thr Gln Leu Gln Pro Phe
            180                 185                 190 ctg aaa ctg aaa cag aaa cag gca aac ctg gtt ctg aaa att atc gaa      624
Leu Lys Leu Lys Gln Lys Gln Ala Asn Leu Val Leu Lys Ile Ile Glu
        195                 200                 205 cag ctg ccg tct gca aaa gaa tcc ccg gac aaa ttc ctg gaa gtt tgt      672
Gln Leu Pro Ser Ala Lys Glu Ser Pro Asp Lys Phe Leu Glu Val Cys
    210                 215                 220 acc tgg gtg gat cag att gca gct ctg aac gat tct aag acg cgt aaa      720
Thr Trp Val Asp Gln Ile Ala Ala Leu Asn Asp Ser Lys Thr Arg Lys
225                 230                 235                 240 acc act tct gaa acc gtt cgt gct gtg ctg gac agc ctg agc gag aag      768
Thr Thr Ser Glu Thr Val Arg Ala Val Leu Asp Ser Leu Ser Glu Lys
                245                 250                 255 aag aaa tcc tcc ccg gcg gcc gac tag                                  795
Lys Lys Ser Ser Pro Ala Ala Asp
            260
```

<210> SEQ ID NO 6
<211> LENGTH: 264
<212> TYPE: PRT
<213> ORGANISM: Artificial sequence
<220> FEATURE:
<223> OTHER INFORMATION: Description of artificial sequence: Fig
      5 and 7 sequence

<400> SEQUENCE: 6

```
Met Ala Asn Thr Lys Tyr Asn Lys Glu Phe Leu Leu Tyr Leu Ala Gly
  1               5                  10                  15

Phe Val Asp Gly Asp Gly Ser Ile Ile Ala Gln Ile Lys Pro Asn Gln
                 20                  25                  30

Ser Tyr Lys Phe Lys His Gln Leu Ser Leu Thr Phe Gln Val Thr Gln
             35                  40                  45

Lys Thr Gln Arg Arg Trp Phe Leu Asp Lys Leu Val Asp Glu Ile Gly
         50                  55                  60
```

-continued

```
Val Gly Tyr Val Arg Asp Arg Gly Ser Val Ser Asp Tyr Ile Leu Ser
 65                  70                  75                  80

Glu Ile Lys Pro Leu His Asn Phe Leu Thr Gln Leu Gln Ala Met Leu
                 85                  90                  95

Glu Arg Ile Arg Leu Phe Asn Met Arg Glu Phe Leu Leu Tyr Leu Ala
            100                 105                 110

Gly Phe Val Asp Gly Asp Gly Ser Ile Ile Ala Gln Ile Lys Pro Asn
        115                 120                 125

Gln Ser Tyr Lys Phe Lys His Gln Leu Ser Leu Thr Phe Gln Val Thr
    130                 135                 140

Gln Lys Thr Gln Arg Arg Trp Phe Leu Asp Lys Leu Val Asp Glu Ile
145                 150                 155                 160

Gly Val Gly Tyr Val Arg Asp Arg Gly Ser Val Ser Asp Tyr Ile Leu
                165                 170                 175

Ser Glu Ile Lys Pro Leu His Asn Phe Leu Thr Gln Leu Gln Pro Phe
            180                 185                 190

Leu Lys Leu Lys Gln Lys Gln Ala Asn Leu Val Leu Lys Ile Ile Glu
        195                 200                 205

Gln Leu Pro Ser Ala Lys Glu Ser Pro Asp Lys Phe Leu Glu Val Cys
    210                 215                 220

Thr Trp Val Asp Gln Ile Ala Ala Leu Asn Asp Ser Lys Thr Arg Lys
225                 230                 235                 240

Thr Thr Ser Glu Thr Val Arg Ala Val Leu Asp Ser Leu Ser Glu Lys
                245                 250                 255

Lys Lys Ser Ser Pro Ala Ala Asp
            260

<210> SEQ ID NO 7
<211> LENGTH: 17
<212> TYPE: PRT
<213> ORGANISM: Artificial sequence
<220> FEATURE:
<223> OTHER INFORMATION: Description of artificial sequence: linker

<400> SEQUENCE: 7

Asn Met Leu Glu Arg Ile Arg Leu Phe Asn Met Arg Glu Gln Leu Ala
1               5                   10                  15

Phe

<210> SEQ ID NO 8
<211> LENGTH: 12
<212> TYPE: PRT
<213> ORGANISM: Artificial sequence
<220> FEATURE:
<223> OTHER INFORMATION: Description of artificial sequence: linker

<400> SEQUENCE: 8

Ala Met Leu Glu Arg Ile Arg Leu Phe Asn Met Arg
1               5                   10

<210> SEQ ID NO 9
<211> LENGTH: 12
<212> TYPE: PRT
<213> ORGANISM: Artificial sequence
<220> FEATURE:
<223> OTHER INFORMATION: Description of artificial sequence: linker

<400> SEQUENCE: 9

Ala Phe Leu Glu Arg Ile Arg Leu Phe Asn Met Arg
1               5                   10
```

-continued

```
<210> SEQ ID NO 10
<211> LENGTH: 12
<212> TYPE: PRT
<213> ORGANISM: Artificial sequence
<220> FEATURE:
<223> OTHER INFORMATION: Description of artificial sequence: linker

<400> SEQUENCE: 10

Ala Met Leu Glu Arg Ile Arg Leu Tyr Asn Met Arg
1               5                   10

<210> SEQ ID NO 11
<211> LENGTH: 12
<212> TYPE: PRT
<213> ORGANISM: Artificial sequence
<220> FEATURE:
<223> OTHER INFORMATION: Description of artificial sequence: linker

<400> SEQUENCE: 11

Ala Phe Leu Glu Arg Ile Arg Leu Tyr Asn Met Arg
1               5                   10

<210> SEQ ID NO 12
<211> LENGTH: 27
<212> TYPE: DNA
<213> ORGANISM: Artificial sequence
<220> FEATURE:
<223> OTHER INFORMATION: Description of artificial sequence: wild type
      I-Cre I

<400> SEQUENCE: 12
caaaacgtcg tgagacagtt tggtcca                                        27

<210> SEQ ID NO 13
<211> LENGTH: 27
<212> TYPE: DNA
<213> ORGANISM: Artificial sequence
<220> FEATURE:
<223> OTHER INFORMATION: Description of artificial sequence: wild type
      I-Dmo I

<400> SEQUENCE: 13
ccttgccggg taagttccgg cgcgcat                                        27

<210> SEQ ID NO 14
<211> LENGTH: 27
<212> TYPE: DNA
<213> ORGANISM: Artificial sequence
<220> FEATURE:
<223> OTHER INFORMATION: Description of artificial sequence: L/C target

<400> SEQUENCE: 14
ccttgccggg tgagacagtt tggtcca                                        27

<210> SEQ ID NO 15
<211> LENGTH: 27
<212> TYPE: DNA
<213> ORGANISM: Artificial sequence
<220> FEATURE:
<223> OTHER INFORMATION: Description of artificial sequence: L/C target

<400> SEQUENCE: 15
caaaacgtcg taagttccgg cgcgcat                                        27

<210> SEQ ID NO 16
<211> LENGTH: 18
<212> TYPE: DNA
```

```
<213> ORGANISM: Artificial sequence
<220> FEATURE:
<223> OTHER INFORMATION: Description of artificial sequence: wild type
      I-Sce I

<400> SEQUENCE: 16
tagggataac agggtaat                                                     18

<210> SEQ ID NO 17
<211> LENGTH: 9
<212> TYPE: PRT
<213> ORGANISM: artificial sequence
<220> FEATURE:
<223> OTHER INFORMATION: protein motif

<400> SEQUENCE: 17

Leu Ala Gly Leu Ile Asp Ala Asp Gly
1               5

<210> SEQ ID NO 18
<211> LENGTH: 109
<212> TYPE: PRT
<213> ORGANISM: Desulfurococcus mobilis

<400> SEQUENCE: 18

Met His Asn Asn Glu Asn Val Ser Gly Ile Ser Ala Tyr Leu Leu Gly
1               5                   10                  15

Leu Ile Ile Gly Asp Gly Gly Leu Tyr Lys Leu Lys Tyr Lys Gly Asn
                20                  25                  30

Arg Ser Glu Tyr Arg Val Val Ile Thr Gln Lys Ser Glu Asn Leu Ile
            35                  40                  45

Lys Gln His Ile Ala Pro Leu Met Gln Phe Leu Ile Asp Glu Leu Asn
        50                  55                  60

Val Lys Ser Lys Ile Gln Ile Val Lys Gly Asp Thr Arg Tyr Glu Leu
65                  70                  75                  80

Arg Val Ser Ser Lys Lys Leu Tyr Tyr Tyr Phe Ala Asn Met Leu Glu
                85                  90                  95

Arg Ile Arg Leu Phe Asn Met Arg Glu Gln Ile Ala Phe
            100                 105

<210> SEQ ID NO 19
<211> LENGTH: 163
<212> TYPE: PRT
<213> ORGANISM: Chlamydomonas reinhardtii

<400> SEQUENCE: 19

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
                20                  25                  30

Tyr Lys Phe Lys His Gln Leu Ser Leu Thr Phe Gln Val Thr Gln Lys
            35                  40                  45

Thr Gln Arg Arg Trp Phe Leu Asp Lys Leu Val Asp Glu Ile Gly Val
        50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110
```

```
Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro

<210> SEQ ID NO 20
<211> LENGTH: 9
<212> TYPE: PRT
<213> ORGANISM: artificial sequence
<220> FEATURE:
<223> OTHER INFORMATION: Description of artificial sequence:
      dodecapeptide motif

<400> SEQUENCE: 20

Leu Leu Gly Leu Ile Ile Gly Asp Gly
1               5

<210> SEQ ID NO 21
<211> LENGTH: 9
<212> TYPE: PRT
<213> ORGANISM: artificial sequence
<220> FEATURE:
<223> OTHER INFORMATION: Description of artificial sequence:
      dodecapeptide motif

<400> SEQUENCE: 21

Leu Ala Gly Phe Val Asp Gly Asp Gly
1               5
```